United States Patent
Wang et al.

(10) Patent No.: US 10,351,831 B2
(45) Date of Patent: *Jul. 16, 2019

(54) FUSION POLYMERASES

(71) Applicant: Bio-Rad Laboratories, Inc., Hercules, CA (US)

(72) Inventors: Yan Wang, San Francisco, CA (US); Man Cheng, Danville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/801,114

(22) Filed: Nov. 1, 2017

(65) Prior Publication Data

US 2018/0127732 A1    May 10, 2018

Related U.S. Application Data

(63) Continuation of application No. 14/562,396, filed on Dec. 5, 2014, now Pat. No. 9,840,697.

(60) Provisional application No. 61/912,981, filed on Dec. 6, 2013, provisional application No. 62/006,409, filed on Jun. 2, 2014.

(51) Int. Cl.
*C12N 9/12* (2006.01)
*C12Q 1/686* (2018.01)
*C12N 9/22* (2006.01)

(52) U.S. Cl.
CPC .............. *C12N 9/1252* (2013.01); *C12N 9/22* (2013.01); *C12Q 1/686* (2013.01); *C07K 2319/80* (2013.01)

(58) Field of Classification Search
None
See application file for complete search history.

(56) References Cited

U.S. PATENT DOCUMENTS

| | | | |
|---|---|---|---|
| 7,122,364 B1 * | 10/2006 | Lyamichev | C12N 9/22 435/199 |
| 7,244,602 B2 | 7/2007 | Frey et al. | |
| 2002/0119461 A1 | 8/2002 | Chatterjee | |
| 2003/0138805 A1 | 7/2003 | Loffert et al. | |
| 2004/0058362 A1 | 3/2004 | Frey et al. | |
| 2008/0227159 A1 | 9/2008 | Hogrefe et al. | |
| 2012/0258460 A1 | 10/2012 | Cheng et al. | |
| 2012/0329126 A1 | 12/2012 | Wang et al. | |

FOREIGN PATENT DOCUMENTS

| | | |
|---|---|---|
| WO | 0118213 | 3/2001 |
| WO | 0161015 | 8/2001 |

OTHER PUBLICATIONS

International Search Report and Written Opinion from International Appl. No. PCT/US2014/068887, dated Mar. 30, 2015.
European Patent Application No. EP14867322.1 , "Extended European Search Report", dated Sep. 26, 2016, 8 pages.
Holland et al., "Detection of specific polymerase chain reaction product by utilizing the 5'-3' exonuclease activity of thermos aquaticus DNA polymerase", Biochemistry, Proceeding of the National Academy of Sciences, USA, Washington D.C., USA, vol. 88, No. 16, Aug. 1991, pp. 7276-7280.
Kaiser et al.; "A comparison of eubacterial and archaeal structure-specific 5'-exonucleases"; *J. Biol. Chem.*; 274:21387-21394 (1999).
Matsukawa, H. et al.; "A useful strategy to construct DNA polymerases with different properties by using genetic resources from environmental DNA"; *Genes Genet. Syst.*; No. 84; 2009; pp. 3-13.
Ngo, et al.; "The Protein Folding Problem and Tertiary Structure Prediction"; 1994; Merz et al. (ed.); Birkhauser, Boston, MA; pp. 433 and 492-495.
Rao et al.; "*Methanococcus jannaschii* flap endonuclease: expression, purification, and substrate requirements";*J. Bacteriol.*; 180:5406-5412 (1998).
Wang et al., "A novel strategy to engineer DNA polymerases for enhanced processivity and improved performance in vitro", Nucleic Acids Research, vol. 32, No. 3, Jan. 1, 2004, pp. 1197-1207.

* cited by examiner

*Primary Examiner* — Richard G Hutson

(74) *Attorney, Agent, or Firm* — Kilpatrick Townsend and Stockton LLP

(57) ABSTRACT

Fusion polypeptides having a heterologous 5'-3' exonuclease domain linked to a polymerase that does not naturally have 5'-3' exonuclease activity, as well as methods of their use are provided. Other aspects are also disclosed.

18 Claims, 4 Drawing Sheets

Specification includes a Sequence Listing.

iQ Multiplex Powermix – Taq DNA polymerase based qPCR mix

Negative control – *pfu* based DNA polymerase

Fusion protein #1 – *pfu* based DNA polymerase fused with *pfu* flap endonuclease Fusion protein #2 – fragment of *pfu* based DNA polymerase (USD minus) fused with *pfu* flap endonuclease Fusion protein #3 – *pfu* based DNA polymerase fused with *Da* flap endonuclease Fusion protein #4 – fragment of *pfu* based DNA polymerase (USD minus) fused with *Da* flap endonuclease

```
SEQUENCE LISTING

<160> NUMBER OF SEQ ID NOS: 41

<210> SEQ ID NO 1
<211> LENGTH: 1195
<212> TYPE: PRT
<213> ORGANISM: Artificial Sequence
<220> FEATURE:
<223> OTHER INFORMATION: synthetic full length Pfu FEN1-polymerase-Sso7d
      fusion DNA polymerase, fusion protein #1, Archaeon
      Pyrococcus furiosus flap endonuclease (Pfu FEN1)
      fused to Sulfolobus solfataricus Sso7d

<400> SEQUENCE: 1

Met Gly Val Pro Ile Gly Glu Ile Ile Pro Arg Lys Glu Ile Glu Leu
  1               5                  10                  15

Glu Asn Leu Tyr Gly Lys Lys Ile Ala Ile Asp Ala Leu Asn Ala Ile
                 20                  25                  30

Tyr Gln Phe Leu Ser Thr Ile Arg Gln Lys Asp Gly Thr Pro Leu Met
             35                  40                  45

Asp Ser Lys Gly Arg Ile Thr Ser His Leu Ser Gly Leu Phe Tyr Arg
         50                  55                  60

Thr Ile Asn Leu Met Glu Ala Gly Ile Lys Pro Val Tyr Val Phe Asp
 65                  70                  75                  80

Gly Glu Pro Pro Glu Phe Lys Lys Lys Glu Leu Lys Arg Arg Glu
                 85                  90                  95

Ala Arg Glu Glu Ala Glu Lys Trp Arg Glu Ala Leu Glu Lys Gly
            100                 105                 110

Glu Ile Glu Glu Ala Arg Lys Tyr Ala Gln Arg Ala Thr Arg Val Asn
        115                 120                 125

Glu Met Leu Ile Glu Asp Ala Lys Lys Leu Leu Glu Leu Met Gly Ile
    130                 135                 140

Pro Ile Val Gln Ala Pro Ser Glu Gly Glu Ala Gln Ala Ala Tyr Met
145                 150                 155                 160
```

-continued

```
Ala Ala Lys Gly Ser Val Tyr Ala Ser Ala Ser Gln Asp Tyr Asp Ser
            165                 170                 175

Leu Leu Phe Gly Ala Pro Arg Leu Val Arg Asn Leu Thr Ile Thr Gly
        180                 185                 190

Lys Arg Lys Leu Pro Gly Lys Asn Val Tyr Val Glu Ile Lys Pro Glu
    195                 200                 205

Leu Ile Ile Leu Glu Glu Val Leu Lys Glu Leu Lys Leu Thr Arg Glu
210                 215                 220

Lys Leu Ile Glu Leu Ala Ile Leu Val Gly Thr Asp Tyr Asn Pro Gly
225                 230                 235                 240

Gly Ile Lys Gly Ile Gly Leu Lys Lys Ala Leu Glu Ile Val Arg His
            245                 250                 255

Ser Lys Asp Pro Leu Ala Lys Phe Gln Lys Gln Ser Asp Val Asp Leu
        260                 265                 270

Tyr Ala Ile Lys Glu Phe Phe Leu Asn Pro Pro Val Thr Asp Asn Tyr
    275                 280                 285

Asn Leu Val Trp Arg Asp Pro Asp Glu Glu Gly Ile Leu Lys Phe Leu
290                 295                 300

Cys Asp Glu His Asp Phe Ser Glu Glu Arg Val Lys Asn Gly Leu Glu
305                 310                 315                 320

Arg Leu Lys Lys Ala Ile Lys Ser Gly Gly Ser Gly Gly Gly
            325                 330                 335

Ser Gly Gly Gly Ser Ile Leu Asp Ala Asp Tyr Ile Thr Glu Glu
        340                 345                 350

Gly Lys Pro Val Ile Arg Leu Phe Lys Lys Glu Asn Gly Glu Phe Lys
    355                 360                 365

Ile Glu His Asp Arg Thr Phe Arg Pro Tyr Ile Tyr Ala Leu Leu Lys
370                 375                 380

Asp Asp Ser Lys Ile Glu Glu Val Lys Lys Ile Thr Ala Glu Arg His
385                 390                 395                 400

Gly Lys Ile Val Arg Ile Val Asp Ala Glu Lys Val Glu Lys Lys Phe
            405                 410                 415

Leu Gly Arg Pro Ile Thr Val Trp Arg Leu Tyr Phe Glu His Pro Gln
        420                 425                 430

Asp Val Pro Thr Ile Arg Glu Lys Ile Arg Glu His Ser Ala Val Val
    435                 440                 445

Asp Ile Phe Glu Tyr Asp Ile Pro Phe Ala Lys Arg Tyr Leu Ile Asp
450                 455                 460

Lys Gly Leu Ile Pro Met Glu Gly Asp Glu Glu Leu Lys Leu Leu Ala
465                 470                 475                 480

Phe Ala Ile Ala Thr Leu Tyr His Glu Gly Glu Glu Phe Gly Lys Gly
            485                 490                 495

Pro Ile Ile Met Ile Ser Tyr Ala Asp Glu Glu Glu Ala Lys Val Ile
        500                 505                 510

Thr Trp Lys Lys Ile Asp Leu Pro Tyr Val Glu Val Ser Ser Glu
    515                 520                 525

Arg Glu Met Ile Lys Arg Phe Leu Lys Ile Arg Glu Lys Asp Pro
530                 535                 540

Asp Ile Ile Ile Thr Tyr Asn Gly Asp Ser Phe Asp Leu Pro Tyr Leu
545                 550                 555                 560

Ala Lys Arg Ala Glu Lys Leu Gly Ile Lys Leu Thr Ile Gly Arg Asp
            565                 570                 575
```

```
Gly Ser Glu Pro Lys Met Gln Arg Ile Gly Asp Met Thr Ala Val Glu
            580                 585                 590

Val Lys Gly Arg Ile His Phe Asp Leu Tyr His Val Ile Arg Arg Thr
        595                 600                 605

Ile Asn Leu Pro Thr Tyr Thr Leu Glu Ala Val Tyr Glu Ala Ile Phe
    610                 615                 620

Gly Lys Pro Lys Glu Lys Val Tyr Ala Asp Glu Ile Ala Lys Ala Trp
625                 630                 635                 640

Glu Thr Gly Glu Gly Leu Glu Arg Val Ala Lys Tyr Ser Met Glu Asp
                645                 650                 655

Ala Lys Ala Thr Tyr Glu Leu Gly Lys Glu Phe Phe Pro Met Glu Ala
            660                 665                 670

Gln Leu Ser Arg Leu Val Gly Gln Pro Leu Trp Asp Val Ser Arg Ser
        675                 680                 685

Ser Thr Gly Asn Leu Val Glu Trp Phe Leu Arg Lys Ala Tyr Glu
    690                 695                 700

Arg Asn Glu Leu Ala Pro Asn Lys Pro Asp Glu Arg Glu Tyr Glu Arg
705                 710                 715                 720

Arg Leu Arg Glu Ser Tyr Ala Gly Gly Phe Val Lys Glu Pro Glu Lys
                725                 730                 735

Gly Leu Trp Glu Asn Ile Val Ser Leu Asp Phe Arg Ala Leu Tyr Pro
            740                 745                 750

Ser Ile Ile Ile Thr His Asn Val Ser Pro Asp Thr Leu Asn Arg Glu
        755                 760                 765

Gly Cys Arg Asn Tyr Asp Val Ala Pro Glu Val Gly His Lys Phe Cys
    770                 775                 780

Lys Asp Phe Pro Gly Phe Ile Pro Ser Leu Leu Lys Arg Leu Leu Asp
785                 790                 795                 800

Glu Arg Gln Lys Ile Lys Thr Lys Met Lys Ala Ser Gln Asp Pro Ile
                805                 810                 815

Glu Lys Ile Met Leu Asp Tyr Arg Gln Arg Ala Ile Lys Ile Leu Ala
            820                 825                 830

Asn Ser Tyr Tyr Gly Tyr Tyr Gly Tyr Ala Lys Ala Arg Trp Tyr Cys
        835                 840                 845

Lys Glu Cys Ala Glu Ser Val Thr Ala Trp Gly Arg Glu Tyr Ile Glu
850                 855                 860

Phe Val Trp Lys Glu Leu Glu Glu Lys Phe Gly Phe Lys Val Leu Tyr
865                 870                 875                 880

Ile Asp Thr Asp Gly Leu Tyr Ala Thr Ile Pro Gly Gly Lys Ser Glu
                885                 890                 895

Glu Ile Lys Lys Lys Ala Leu Glu Phe Val Asp Tyr Ile Asn Ala Lys
            900                 905                 910

Leu Pro Gly Leu Leu Glu Leu Glu Tyr Glu Gly Phe Tyr Lys Arg Gly
        915                 920                 925

Phe Phe Val Thr Lys Lys Tyr Ala Leu Ile Asp Glu Glu Gly Lys
    930                 935                 940

Ile Ile Thr Arg Gly Leu Glu Ile Val Arg Arg Asp Trp Ser Glu Ile
945                 950                 955                 960

Ala Lys Glu Thr Gln Ala Arg Val Leu Glu Ala Ile Leu Lys His Gly
                965                 970                 975

Asn Val Glu Glu Ala Val Arg Ile Val Lys Glu Val Thr Gln Lys Leu
            980                 985                 990

Ser Lys Tyr Glu Ile Pro Pro Glu Lys Leu Ala Ile Tyr Glu Gln Ile
```

```
                995                1000               1005
Thr Arg Pro Leu His Glu Tyr Lys Ala Ile Gly Pro His Val Ala Val
           1010               1015               1020
Ala Lys Arg Leu Ala Ala Lys Gly Val Lys Ile Lys Pro Gly Met Val
1025               1030               1035               1040
Ile Gly Tyr Ile Val Leu Arg Gly Asp Gly Pro Ile Ser Asn Arg Ala
               1045               1050               1055
Ile Leu Ala Glu Glu Tyr Asp Pro Arg Lys His Lys Tyr Asp Ala Glu
           1060               1065               1070
Tyr Tyr Ile Glu Asn Gln Val Leu Pro Ala Val Leu Arg Ile Leu Glu
       1075               1080               1085
Gly Phe Gly Tyr Arg Lys Glu Asp Leu Arg Trp Gln Lys Thr Lys Gln
       1090               1095               1100
Thr Gly Leu Thr Ser Trp Leu Asn Ile Lys Lys Ser Gly Thr Gly Gly
1105               1110               1115               1120
Gly Gly Ala Thr Val Lys Phe Lys Tyr Lys Gly Glu Glu Lys Glu Val
               1125               1130               1135
Asp Ile Ser Lys Ile Lys Lys Val Trp Arg Val Gly Pro Met Ile Ser
           1140               1145               1150
Phe Thr Tyr Asp Glu Gly Gly Gly Lys Thr Gly Arg Gly Ala Val Ser
       1155               1160               1165
Glu Lys Asp Ala Pro Lys Glu Leu Leu Gln Met Leu Glu Lys Gln Lys
       1170               1175               1180
Ala Ala Ala Leu Glu His His His His His His
1185               1190               1195

<210> SEQ ID NO 2
<211> LENGTH: 1070
<212> TYPE: PRT
<213> ORGANISM: Artificial Sequence
<220> FEATURE:
<223> OTHER INFORMATION: synthetic full length Da FEN1-polymerase-Sso7d
      fusion DNA polymerase, fusion protein #2, Archaeon
      Desulfurococcus amylolyticus flap endonuclease (Da
      FEN1) fused to Sulfolobus solfataricus Sso7d

<400> SEQUENCE: 2

Met Gly Val Pro Ile Gly Glu Ile Ile Pro Arg Lys Glu Ile Glu Leu
1               5                   10                  15
Glu Asn Leu Tyr Gly Lys Lys Ile Ala Ile Asp Ala Leu Asn Ala Ile
               20                  25                  30
Tyr Gln Phe Leu Ser Thr Ile Arg Gln Lys Asp Gly Thr Pro Leu Met
           35                  40                  45
Asp Ser Lys Gly Arg Ile Thr Ser His Leu Ser Gly Leu Phe Tyr Arg
       50                  55                  60
Thr Ile Asn Leu Met Glu Ala Gly Ile Lys Pro Val Tyr Val Phe Asp
65                  70                  75                  80
Gly Glu Pro Pro Glu Phe Lys Lys Lys Glu Leu Glu Lys Arg Arg Glu
                   85                  90                  95
Ala Arg Glu Glu Ala Glu Glu Lys Trp Arg Glu Ala Leu Glu Lys Gly
               100                 105                 110
Glu Ile Glu Glu Ala Arg Lys Tyr Ala Gln Arg Ala Thr Arg Val Asn
           115                 120                 125
Glu Met Leu Ile Glu Asp Ala Lys Lys Leu Leu Glu Leu Met Gly Ile
       130                 135                 140
Pro Ile Val Gln Ala Pro Ser Glu Gly Glu Ala Gln Ala Ala Tyr Met
```

-continued

```
145                 150                 155                 160
Ala Ala Lys Gly Ser Val Tyr Ala Ser Ala Ser Gln Asp Tyr Asp Ser
                165                 170                 175
Leu Leu Phe Gly Ala Pro Arg Leu Val Arg Asn Leu Thr Ile Thr Gly
                180                 185                 190
Lys Arg Lys Leu Pro Gly Lys Asn Val Tyr Val Glu Ile Lys Pro Glu
                195                 200                 205
Leu Ile Ile Leu Glu Glu Val Leu Lys Glu Leu Lys Leu Thr Arg Glu
210                 215                 220
Lys Leu Ile Glu Leu Ala Ile Leu Val Gly Thr Asp Tyr Asn Pro Gly
225                 230                 235                 240
Gly Ile Lys Gly Ile Gly Leu Lys Lys Ala Leu Glu Ile Val Arg His
                245                 250                 255
Ser Lys Asp Pro Leu Ala Lys Phe Gln Lys Gln Ser Asp Val Asp Leu
                260                 265                 270
Tyr Ala Ile Lys Glu Phe Phe Leu Asn Pro Pro Val Thr Asp Asn Tyr
                275                 280                 285
Asn Leu Val Trp Arg Asp Pro Asp Glu Glu Gly Ile Leu Lys Phe Leu
                290                 295                 300
Cys Asp Glu His Asp Phe Ser Glu Glu Arg Val Lys Asn Gly Leu Glu
305                 310                 315                 320
Arg Leu Lys Lys Ala Ile Lys Ser Gly Gly Ser Gly Gly Gly Gly
                325                 330                 335
Ser Gly Gly Gly Gly Ser Ile Pro Met Glu Gly Asp Glu Glu Leu Lys
                340                 345                 350
Leu Leu Ala Phe Ala Ile Ala Thr Leu Tyr His Glu Gly Glu Glu Phe
                355                 360                 365
Gly Lys Gly Pro Ile Ile Met Ile Ser Tyr Ala Asp Glu Glu Glu Ala
                370                 375                 380
Lys Val Ile Thr Trp Lys Lys Ile Asp Leu Pro Tyr Val Glu Val Val
385                 390                 395                 400
Ser Ser Glu Arg Glu Met Ile Lys Arg Phe Leu Lys Ile Ile Arg Glu
                405                 410                 415
Lys Asp Pro Asp Ile Ile Ile Thr Tyr Asn Gly Asp Ser Phe Asp Leu
                420                 425                 430
Pro Tyr Leu Ala Lys Arg Ala Glu Lys Leu Gly Ile Lys Leu Thr Ile
                435                 440                 445
Gly Arg Asp Gly Ser Glu Pro Lys Met Gln Arg Ile Gly Asp Met Thr
450                 455                 460
Ala Val Glu Val Lys Gly Arg Ile His Phe Asp Leu Tyr His Val Ile
465                 470                 475                 480
Arg Arg Thr Ile Asn Leu Pro Thr Tyr Thr Leu Glu Ala Val Tyr Glu
                485                 490                 495
Ala Ile Phe Gly Lys Pro Lys Glu Lys Val Tyr Ala Asp Glu Ile Ala
                500                 505                 510
Lys Ala Trp Glu Thr Gly Glu Gly Leu Glu Arg Val Ala Lys Tyr Ser
                515                 520                 525
Met Glu Asp Ala Lys Ala Thr Tyr Glu Leu Gly Lys Glu Phe Phe Pro
                530                 535                 540
Met Glu Ala Gln Leu Ser Arg Leu Val Gly Gln Pro Leu Trp Asp Val
545                 550                 555                 560
Ser Arg Ser Ser Thr Gly Asn Leu Val Glu Trp Phe Leu Leu Arg Lys
                565                 570                 575
```

```
Ala Tyr Glu Arg Asn Glu Leu Ala Pro Asn Lys Pro Asp Glu Arg Glu
            580                 585                 590

Tyr Glu Arg Arg Leu Arg Glu Ser Tyr Ala Gly Gly Phe Val Lys Glu
        595                 600                 605

Pro Glu Lys Gly Leu Trp Glu Asn Ile Val Ser Leu Asp Phe Arg Ala
    610                 615                 620

Leu Tyr Pro Ser Ile Ile Ile Thr His Asn Val Ser Pro Asp Thr Leu
625                 630                 635                 640

Asn Arg Glu Gly Cys Arg Asn Tyr Asp Val Ala Pro Glu Val Gly His
                645                 650                 655

Lys Phe Cys Lys Asp Phe Pro Gly Phe Ile Pro Ser Leu Leu Lys Arg
            660                 665                 670

Leu Leu Asp Glu Arg Gln Lys Ile Lys Thr Lys Met Lys Ala Ser Gln
        675                 680                 685

Asp Pro Ile Glu Lys Ile Met Leu Asp Tyr Arg Gln Arg Ala Ile Lys
    690                 695                 700

Ile Leu Ala Asn Ser Tyr Tyr Gly Tyr Tyr Gly Tyr Ala Lys Ala Arg
705                 710                 715                 720

Trp Tyr Cys Lys Glu Cys Ala Glu Ser Val Thr Ala Trp Gly Arg Glu
                725                 730                 735

Tyr Ile Glu Phe Val Trp Lys Glu Leu Glu Glu Lys Phe Gly Phe Lys
            740                 745                 750

Val Leu Tyr Ile Asp Thr Asp Gly Leu Tyr Ala Thr Ile Pro Gly Gly
        755                 760                 765

Lys Ser Glu Glu Ile Lys Lys Lys Ala Leu Glu Phe Val Asp Tyr Ile
    770                 775                 780

Asn Ala Lys Leu Pro Gly Leu Leu Glu Leu Glu Tyr Glu Gly Phe Tyr
785                 790                 795                 800

Lys Arg Gly Phe Phe Val Thr Lys Lys Lys Tyr Ala Leu Ile Asp Glu
                805                 810                 815

Glu Gly Lys Ile Ile Thr Arg Gly Leu Glu Ile Val Arg Arg Asp Trp
            820                 825                 830

Ser Glu Ile Ala Lys Glu Thr Gln Ala Arg Val Leu Glu Ala Ile Leu
        835                 840                 845

Lys His Gly Asn Val Glu Glu Ala Val Arg Ile Val Lys Glu Val Thr
    850                 855                 860

Gln Lys Leu Ser Lys Tyr Glu Ile Pro Pro Glu Lys Leu Ala Ile Tyr
865                 870                 875                 880

Glu Gln Ile Thr Arg Pro Leu His Glu Tyr Lys Ala Ile Gly Pro His
                885                 890                 895

Val Ala Val Ala Lys Arg Leu Ala Ala Lys Gly Val Lys Ile Lys Pro
            900                 905                 910

Gly Met Val Ile Gly Tyr Ile Val Leu Arg Gly Asp Gly Pro Ile Ser
        915                 920                 925

Asn Arg Ala Ile Leu Ala Glu Glu Tyr Asp Pro Arg Lys His Lys Tyr
    930                 935                 940

Asp Ala Glu Tyr Tyr Ile Glu Asn Gln Val Leu Pro Ala Val Leu Arg
945                 950                 955                 960

Ile Leu Glu Gly Phe Gly Tyr Arg Lys Glu Asp Leu Arg Trp Gln Lys
                965                 970                 975

Thr Lys Gln Thr Gly Leu Thr Ser Trp Leu Asn Ile Lys Lys Ser Gly
            980                 985                 990
```

```
Thr Gly Gly Gly Gly Ala Thr Val Lys Phe Lys Tyr Lys Gly Glu Glu
            995                 1000                1005

Lys Glu Val Asp Ile Ser Lys Ile Lys Lys Val Trp Arg Val Gly Pro
    1010                1015                1020

Met Ile Ser Phe Thr Tyr Asp Glu Gly Gly Lys Thr Gly Arg Gly
1025                1030                1035                1040

Ala Val Ser Glu Lys Asp Ala Pro Lys Glu Leu Leu Gln Met Leu Glu
                1045                1050                1055

Lys Gln Lys Ala Ala Leu Glu His His His His His His
            1060                1065                1070
```

<210> SEQ ID NO 3
<211> LENGTH: 1221
<212> TYPE: PRT
<213> ORGANISM: Artificial Sequence
<220> FEATURE:
<223> OTHER INFORMATION: synthetic full length Pfu FEN1-polymerase (USD minus)-Sso7d fusion DNA polymerase, fusion protein #3, Archaeon Pyrococcus furiosus flap endonuclease (Pfu FEN1) without uracil sensing domain (USD) fused to Sulfolobus solfataricus Sso7d

<400> SEQUENCE: 3

```
Met Gly Val Asp Leu Lys Asp Ile Ile Pro Gly Glu Ala Lys Thr Val
1               5                   10                  15

Ile Glu Asp Leu Arg Ile Leu His Gly Lys Ile Ile Val Ile Asp Gly
            20                  25                  30

Tyr Asn Ala Leu Tyr Gln Phe Leu Ala Ala Ile Arg Gln Pro Asp Gly
        35                  40                  45

Thr Pro Leu Met Asp Asn Asn Gly Arg Ile Thr Ser His Leu Ser Gly
50                  55                  60

Leu Phe Tyr Arg Thr Ile Asn Ile Val Glu Ala Gly Ile Lys Pro Val
65                  70                  75                  80

Tyr Val Phe Asp Gly Lys Pro Pro Glu Leu Lys Ala Arg Glu Ile Glu
                85                  90                  95

Arg Arg Lys Ala Val Lys Glu Glu Ala Ala Lys Lys Tyr Glu Glu Ala
            100                 105                 110

Val Gln Ser Gly Asp Leu Glu Leu Ala Arg Arg Tyr Ala Met Met Ser
        115                 120                 125

Ala Lys Leu Thr Glu Glu Met Val Arg Asp Ala Lys Ser Leu Leu Asp
130                 135                 140

Ala Met Gly Ile Pro Trp Val Gln Ala Pro Ala Glu Gly Glu Ala Gln
145                 150                 155                 160

Ala Ala Tyr Ile Val Lys Lys Gly Asp Ala Tyr Ala Ser Ala Ser Gln
                165                 170                 175

Asp Tyr Asp Ser Leu Leu Phe Gly Ser Pro Lys Leu Val Arg Asn Leu
            180                 185                 190

Thr Ile Ser Gly Arg Arg Lys Leu Pro Arg Lys Asn Glu Tyr Val Glu
        195                 200                 205

Val Lys Pro Glu Leu Ile Glu Leu Asp Lys Leu Leu Val Gln Leu Gly
210                 215                 220

Ile Thr Leu Glu Asn Leu Ile Asp Ile Gly Ile Leu Leu Gly Thr Asp
225                 230                 235                 240

Tyr Asn Pro Asp Gly Phe Glu Gly Ile Gly Pro Lys Lys Ala Leu Gln
                245                 250                 255

Leu Val Lys Ala Tyr Gly Gly Ile Glu Lys Ile Pro Lys Pro Ile Leu
            260                 265                 270
```

```
Lys Ser Pro Ile Glu Val Asp Val Ile Ala Ile Lys Lys Tyr Phe Leu
            275                 280                 285

Gln Pro Gln Val Thr Asp Asn Tyr Arg Ile Glu Trp His Thr Pro Asp
        290                 295                 300

Pro Asp Ala Val Lys Arg Ile Leu Val Asp Glu His Asp Phe Ser Ile
305                 310                 315                 320

Asp Arg Val Ser Thr Ala Leu Glu Arg Tyr Val Lys Ala Phe Lys Glu
                325                 330                 335

Asn Ile Arg Gly Glu Gln Lys Gly Leu Ser Lys Trp Phe Ser Lys Pro
            340                 345                 350

Lys Ser Gly Gly Ser Gly Gly Gly Ser Gly Gly Gly Ser
        355                 360                 365

Ile Leu Asp Ala Asp Tyr Ile Thr Glu Glu Gly Lys Pro Val Ile Arg
370                 375                 380

Leu Phe Lys Lys Glu Asn Gly Glu Phe Lys Ile Glu His Asp Arg Thr
385                 390                 395                 400

Phe Arg Pro Tyr Ile Tyr Ala Leu Leu Lys Asp Asp Ser Lys Ile Glu
                405                 410                 415

Glu Val Lys Lys Ile Thr Ala Glu Arg His Gly Lys Ile Val Arg Ile
            420                 425                 430

Val Asp Ala Glu Lys Val Glu Lys Lys Phe Leu Gly Arg Pro Ile Thr
        435                 440                 445

Val Trp Arg Leu Tyr Phe Glu His Pro Gln Asp Val Pro Thr Ile Arg
        450                 455                 460

Glu Lys Ile Arg Glu His Ser Ala Val Val Asp Ile Phe Glu Tyr Asp
465                 470                 475                 480

Ile Pro Phe Ala Lys Arg Tyr Leu Ile Asp Lys Gly Leu Ile Pro Met
                485                 490                 495

Glu Gly Asp Glu Glu Leu Lys Leu Leu Ala Phe Ala Ile Ala Thr Leu
            500                 505                 510

Tyr His Glu Gly Glu Glu Phe Gly Lys Gly Pro Ile Ile Met Ile Ser
        515                 520                 525

Tyr Ala Asp Glu Glu Glu Ala Lys Val Ile Thr Trp Lys Lys Ile Asp
        530                 535                 540

Leu Pro Tyr Val Glu Val Val Ser Ser Glu Arg Glu Met Ile Lys Arg
545                 550                 555                 560

Phe Leu Lys Ile Ile Arg Glu Lys Asp Pro Asp Ile Ile Ile Thr Tyr
                565                 570                 575

Asn Gly Asp Ser Phe Asp Leu Pro Tyr Leu Ala Lys Arg Ala Glu Lys
            580                 585                 590

Leu Gly Ile Lys Leu Thr Ile Gly Arg Asp Gly Ser Glu Pro Lys Met
        595                 600                 605

Gln Arg Ile Gly Asp Met Thr Ala Val Glu Val Lys Gly Arg Ile His
        610                 615                 620

Phe Asp Leu Tyr His Val Ile Arg Arg Thr Ile Asn Leu Pro Thr Tyr
625                 630                 635                 640

Thr Leu Glu Ala Val Tyr Glu Ala Ile Phe Gly Lys Pro Lys Glu Lys
                645                 650                 655

Val Tyr Ala Asp Glu Ile Ala Lys Ala Trp Glu Thr Gly Glu Gly Leu
            660                 665                 670

Glu Arg Val Ala Lys Tyr Ser Met Glu Asp Ala Lys Ala Thr Tyr Glu
        675                 680                 685

Leu Gly Lys Glu Phe Phe Pro Met Glu Ala Gln Leu Ser Arg Leu Val
```

-continued

```
            690             695             700
Gly Gln Pro Leu Trp Asp Val Ser Arg Ser Ser Thr Gly Asn Leu Val
705                 710                 715                 720

Glu Trp Phe Leu Leu Arg Lys Ala Tyr Glu Arg Asn Glu Leu Ala Pro
            725                 730                 735

Asn Lys Pro Asp Glu Arg Glu Tyr Glu Arg Arg Leu Arg Glu Ser Tyr
                740                 745                 750

Ala Gly Gly Phe Val Lys Glu Pro Glu Lys Gly Leu Trp Glu Asn Ile
            755                 760                 765

Val Ser Leu Asp Phe Arg Ala Leu Tyr Pro Ser Ile Ile Ile Thr His
770                 775                 780

Asn Val Ser Pro Asp Thr Leu Asn Arg Glu Gly Cys Arg Asn Tyr Asp
785                 790                 795                 800

Val Ala Pro Glu Val Gly His Lys Phe Cys Lys Asp Phe Pro Gly Phe
                805                 810                 815

Ile Pro Ser Leu Leu Lys Arg Leu Leu Asp Glu Arg Gln Lys Ile Lys
            820                 825                 830

Thr Lys Met Lys Ala Ser Gln Asp Pro Ile Glu Lys Ile Met Leu Asp
                835                 840                 845

Tyr Arg Gln Arg Ala Ile Lys Ile Leu Ala Asn Ser Tyr Tyr Gly Tyr
            850                 855                 860

Tyr Gly Tyr Ala Lys Ala Arg Trp Tyr Cys Lys Glu Cys Ala Glu Ser
865                 870                 875                 880

Val Thr Ala Trp Gly Arg Glu Tyr Ile Glu Phe Val Trp Lys Glu Leu
                885                 890                 895

Glu Glu Lys Phe Gly Phe Lys Val Leu Tyr Ile Asp Thr Asp Gly Leu
            900                 905                 910

Tyr Ala Thr Ile Pro Gly Gly Lys Ser Glu Glu Ile Lys Lys Lys Ala
            915                 920                 925

Leu Glu Phe Val Asp Tyr Ile Asn Ala Lys Leu Pro Gly Leu Leu Glu
            930                 935                 940

Leu Glu Tyr Glu Gly Phe Tyr Lys Arg Gly Phe Phe Val Thr Lys Lys
945                 950                 955                 960

Lys Tyr Ala Leu Ile Asp Glu Glu Gly Lys Ile Ile Thr Arg Gly Leu
                965                 970                 975

Glu Ile Val Arg Arg Asp Trp Ser Glu Ile Ala Lys Glu Thr Gln Ala
                980                 985                 990

Arg Val Leu Glu Ala Ile Leu Lys His Gly Asn Val Glu Glu Ala Val
            995                 1000                1005

Arg Ile Val Lys Glu Val Thr Gln Lys Leu Ser Lys Tyr Glu Ile Pro
    1010                1015                1020

Pro Glu Lys Leu Ala Ile Tyr Glu Gln Ile Thr Arg Pro Leu His Glu
1025                1030                1035                1040

Tyr Lys Ala Ile Gly Pro His Val Ala Val Ala Lys Arg Leu Ala Ala
                1045                1050                1055

Lys Gly Val Lys Ile Lys Pro Gly Met Val Ile Gly Tyr Ile Val Leu
                1060                1065                1070

Arg Gly Asp Gly Pro Ile Ser Asn Arg Ala Ile Leu Ala Glu Glu Tyr
    1075                1080                1085

Asp Pro Arg Lys His Lys Tyr Asp Ala Glu Tyr Tyr Ile Glu Asn Gln
    1090                1095                1100

Val Leu Pro Ala Val Leu Arg Ile Leu Glu Gly Phe Gly Tyr Arg Lys
1105                1110                1115                1120
```

-continued

```
Glu Asp Leu Arg Trp Gln Lys Thr Lys Gln Thr Gly Leu Thr Ser Trp
            1125                1130                1135

Leu Asn Ile Lys Lys Ser Gly Thr Gly Gly Gly Ala Thr Val Lys
            1140                1145                1150

Phe Lys Tyr Lys Gly Glu Glu Lys Glu Val Asp Ile Ser Lys Ile Lys
            1155                1160                1165

Lys Val Trp Arg Val Gly Pro Met Ile Ser Phe Thr Tyr Asp Glu Gly
        1170                1175                1180

Gly Gly Lys Thr Gly Arg Gly Ala Val Ser Glu Lys Asp Ala Pro Lys
1185                1190                1195                1200

Glu Leu Leu Gln Met Leu Glu Lys Gln Lys Ala Ala Ala Leu Glu His
            1205                1210                1215

His His His His His
            1220

<210> SEQ ID NO 4
<211> LENGTH: 1096
<212> TYPE: PRT
<213> ORGANISM: Artificial Sequence
<220> FEATURE:
<223> OTHER INFORMATION: synthetic full length Da FEN1-polymerase (USD
      minus)-Sso7d fusion DNA polymerase, fusion protein #4, Archaeon
      Desulfurococcus amylolyticus flap endonuclease (Pfu FEN1)
      without uracil sensing domain (USD) fused to Sso7d

<400> SEQUENCE: 4

Met Gly Val Asp Leu Lys Asp Ile Ile Pro Gly Glu Ala Lys Thr Val
 1               5                  10                  15

Ile Glu Asp Leu Arg Ile Leu His Gly Lys Ile Ile Val Ile Asp Gly
                20                  25                  30

Tyr Asn Ala Leu Tyr Gln Phe Leu Ala Ala Ile Arg Gln Pro Asp Gly
            35                  40                  45

Thr Pro Leu Met Asp Asn Asn Gly Arg Ile Thr Ser His Leu Ser Gly
        50                  55                  60

Leu Phe Tyr Arg Thr Ile Asn Ile Val Glu Ala Gly Ile Lys Pro Val
65                  70                  75                  80

Tyr Val Phe Asp Gly Lys Pro Pro Glu Leu Lys Ala Arg Glu Ile Glu
                85                  90                  95

Arg Arg Lys Ala Val Lys Glu Glu Ala Ala Lys Lys Tyr Glu Glu Ala
                100                 105                 110

Val Gln Ser Gly Asp Leu Glu Leu Ala Arg Arg Tyr Ala Met Met Ser
            115                 120                 125

Ala Lys Leu Thr Glu Glu Met Val Arg Asp Ala Lys Ser Leu Leu Asp
        130                 135                 140

Ala Met Gly Ile Pro Trp Val Gln Ala Pro Glu Gly Glu Ala Gln
145                 150                 155                 160

Ala Ala Tyr Ile Val Lys Lys Gly Asp Ala Tyr Ala Ser Ala Ser Gln
                165                 170                 175

Asp Tyr Asp Ser Leu Leu Phe Gly Ser Pro Lys Leu Val Arg Asn Leu
            180                 185                 190

Thr Ile Ser Gly Arg Arg Lys Leu Pro Arg Lys Asn Glu Tyr Val Glu
        195                 200                 205

Val Lys Pro Glu Leu Ile Glu Leu Asp Lys Leu Leu Val Gln Leu Gly
    210                 215                 220

Ile Thr Leu Glu Asn Leu Ile Asp Ile Gly Ile Leu Leu Gly Thr Asp
225                 230                 235                 240
```

```
Tyr Asn Pro Asp Gly Phe Glu Gly Ile Gly Pro Lys Ala Leu Gln
            245                 250                 255

Leu Val Lys Ala Tyr Gly Gly Ile Glu Lys Ile Pro Lys Pro Ile Leu
        260                 265                 270

Lys Ser Pro Ile Glu Val Asp Val Ile Ala Ile Lys Lys Tyr Phe Leu
    275                 280                 285

Gln Pro Gln Val Thr Asp Asn Tyr Arg Ile Glu Trp His Thr Pro Asp
290                     295                 300

Pro Asp Ala Val Lys Arg Ile Leu Val Asp Glu His Asp Phe Ser Ile
305             310                  315                     320

Asp Arg Val Ser Thr Ala Leu Glu Arg Tyr Val Lys Ala Phe Lys Glu
                325                 330                 335

Asn Ile Arg Gly Glu Gln Lys Gly Leu Ser Lys Trp Phe Ser Lys Pro
            340                 345                 350

Lys Ser Gly Gly Gly Ser Gly Gly Gly Ser Gly Gly Gly Gly Ser
        355                 360                 365

Ile Pro Met Glu Gly Asp Glu Glu Leu Lys Leu Leu Ala Phe Ala Ile
        370                 375                 380

Ala Thr Leu Tyr His Glu Gly Glu Glu Phe Gly Lys Gly Pro Ile Ile
385                 390                 395                 400

Met Ile Ser Tyr Ala Asp Glu Glu Glu Ala Lys Val Ile Thr Trp Lys
                405                 410                 415

Lys Ile Asp Leu Pro Tyr Val Glu Val Val Ser Ser Glu Arg Glu Met
            420                 425                 430

Ile Lys Arg Phe Leu Lys Ile Arg Glu Lys Asp Pro Asp Ile Ile
        435                 440                 445

Ile Thr Tyr Asn Gly Asp Ser Phe Asp Leu Pro Tyr Leu Ala Lys Arg
        450                 455                 460

Ala Glu Lys Leu Gly Ile Lys Leu Thr Ile Gly Arg Asp Gly Ser Glu
465                 470                 475                 480

Pro Lys Met Gln Arg Ile Gly Asp Met Thr Ala Val Glu Val Lys Gly
                485                 490                 495

Arg Ile His Phe Asp Leu Tyr His Val Ile Arg Arg Thr Ile Asn Leu
                500                 505                 510

Pro Thr Tyr Thr Leu Glu Ala Val Tyr Glu Ala Ile Phe Gly Lys Pro
            515                 520                 525

Lys Glu Lys Val Tyr Ala Asp Glu Ile Ala Lys Ala Trp Glu Thr Gly
530                 535                 540

Glu Gly Leu Glu Arg Val Ala Lys Tyr Ser Met Glu Asp Ala Lys Ala
545                 550                 555                 560

Thr Tyr Glu Leu Gly Lys Glu Phe Phe Pro Met Glu Ala Gln Leu Ser
                565                 570                 575

Arg Leu Val Gly Gln Pro Leu Trp Asp Val Ser Arg Ser Ser Thr Gly
            580                 585                 590

Asn Leu Val Glu Trp Phe Leu Leu Arg Lys Ala Tyr Glu Arg Asn Glu
                595                 600                 605

Leu Ala Pro Asn Lys Pro Asp Glu Arg Glu Tyr Glu Arg Arg Leu Arg
        610                 615                 620

Glu Ser Tyr Ala Gly Gly Phe Val Lys Glu Pro Glu Lys Gly Leu Trp
625                 630                 635                 640

Glu Asn Ile Val Ser Leu Asp Phe Arg Ala Leu Tyr Pro Ser Ile Ile
                645                 650                 655
```

-continued

```
Ile Thr His Asn Val Ser Pro Asp Thr Leu Asn Arg Glu Gly Cys Arg
            660                 665                 670
Asn Tyr Asp Val Ala Pro Glu Val Gly His Lys Phe Cys Lys Asp Phe
        675                 680                 685
Pro Gly Phe Ile Pro Ser Leu Leu Lys Arg Leu Leu Asp Glu Arg Gln
    690                 695                 700
Lys Ile Lys Thr Lys Met Lys Ala Ser Gln Asp Pro Ile Glu Lys Ile
705                 710                 715                 720
Met Leu Asp Tyr Arg Gln Arg Ala Ile Lys Ile Leu Ala Asn Ser Tyr
                725                 730                 735
Tyr Gly Tyr Tyr Gly Tyr Ala Lys Ala Arg Trp Tyr Cys Lys Glu Cys
            740                 745                 750
Ala Glu Ser Val Thr Ala Trp Gly Arg Glu Tyr Ile Glu Phe Val Trp
        755                 760                 765
Lys Glu Leu Glu Glu Lys Phe Gly Phe Lys Val Leu Tyr Ile Asp Thr
    770                 775                 780
Asp Gly Leu Tyr Ala Thr Ile Pro Gly Gly Lys Ser Glu Glu Ile Lys
785                 790                 795                 800
Lys Lys Ala Leu Glu Phe Val Asp Tyr Ile Asn Ala Lys Leu Pro Gly
                805                 810                 815
Leu Leu Glu Leu Glu Tyr Glu Gly Phe Tyr Lys Arg Gly Phe Phe Val
            820                 825                 830
Thr Lys Lys Lys Tyr Ala Leu Ile Asp Glu Glu Gly Lys Ile Ile Thr
        835                 840                 845
Arg Gly Leu Glu Ile Val Arg Arg Asp Trp Ser Glu Ile Ala Lys Glu
    850                 855                 860
Thr Gln Ala Arg Val Leu Glu Ala Ile Leu Lys His Gly Asn Val Glu
865                 870                 875                 880
Glu Ala Val Arg Ile Val Lys Glu Val Thr Gln Lys Leu Ser Lys Tyr
                885                 890                 895
Glu Ile Pro Pro Glu Lys Leu Ala Ile Tyr Glu Gln Ile Thr Arg Pro
            900                 905                 910
Leu His Glu Tyr Lys Ala Ile Gly Pro His Val Ala Val Ala Lys Arg
        915                 920                 925
Leu Ala Ala Lys Gly Val Lys Ile Lys Pro Gly Met Val Ile Gly Tyr
    930                 935                 940
Ile Val Leu Arg Gly Asp Gly Pro Ile Ser Asn Arg Ala Ile Leu Ala
945                 950                 955                 960
Glu Glu Tyr Asp Pro Arg Lys His Lys Tyr Asp Ala Glu Tyr Tyr Ile
                965                 970                 975
Glu Asn Gln Val Leu Pro Ala Val Leu Arg Ile Leu Glu Gly Phe Gly
            980                 985                 990
Tyr Arg Lys Glu Asp Leu Arg Trp Gln Lys Thr Lys Gln Thr Gly Leu
        995                1000                1005
Thr Ser Trp Leu Asn Ile Lys Lys Ser Gly Thr Gly Gly Gly Gly Ala
    1010                1015                1020
Thr Val Lys Phe Lys Tyr Lys Gly Glu Glu Lys Glu Val Asp Ile Ser
1025                1030                1035                1040
Lys Ile Lys Lys Val Trp Arg Val Gly Pro Met Ile Ser Phe Thr Tyr
                1045                1050                1055
Asp Glu Gly Gly Gly Lys Thr Gly Arg Gly Ala Val Ser Glu Lys Asp
            1060                1065                1070
Ala Pro Lys Glu Leu Leu Gln Met Leu Glu Lys Gln Lys Ala Ala Ala
```

```
                1075         1080         1085
Leu Glu His His His His His His
      1090         1095

<210> SEQ ID NO 5
<211> LENGTH: 3602
<212> TYPE: DNA
<213> ORGANISM: Artificial Sequence
<220> FEATURE:
<223> OTHER INFORMATION: synthetic full length codon-optimized Pfu FEN1-
      polymerase-Sso7d fusion DNA polymerase, fusion protein #1,
      Archaeon Pyrococcus furiosus flap endonuclease (Pfu FEN1) fused to
      Sulfolobus solfataricus Sso7d

<400> SEQUENCE: 5
atgggcgtgc cgatcggtga atcatccca cgtaaagaaa tcgagctgga gaacctgtac     60
ggtaaaaaaa ttgctatcga cgctctcaac gccatttacc agttcctgtc aactatccgt    120
cagaaagacg gcactccgct catggatagc aagggtcgta ttacctctca cctgtccggc    180
ctgttctacc gtacgatcaa tctgatggaa gcagggatta aaccggtcta tgtgttcgat    240
ggcgaaccgc cagagttcaa aaagaaagag ttggaaaaac gccgtgaagc acgtgaagaa    300
gcggaagaaa atggcgtga gctctctgga aaaggcgaaa tcgaagaagc gcgtaaatac    360
gcccagcgtg cgacccgtgt caatgaaatg ctgatcgaag acgccaaaaa actgctggaa    420
ttgatgggta tccctatcgt gcaggctcca tctgaaggcg aagctcaagc ggcgtatatg    480
gccgcaaaag gctctgttta tgcgtctgct tcccaagatt acgactccct gctgtttggt    540
gcaccgcgcc tggtgcgtaa cctgaccatc acgggtaagc gtaagttgcc gggtaagaac    600
gtttatgtgg aaattaaacc tgaactgatt attctggaag aggtcctgaa agagctgaaa    660
ctgacacgcg aaaaactgat tgaactggct atcctggttg cacagactaa caccccaggc    720
ggtatcaaag catcggtct gaaaaagcg cttgaaatcg tgcgtcacag taaagatccg    780
ctggctaagt tcagaaaca gagcgacgtg gacctgtatg caattaaaga gttcttcctg    840
aaccctccgg ttactgataa ctacaacctg gtttggcgcg atccagacga ggagggtatc    900
ctgaaatttc tgtgtgatga acacgatttt ccgaggaac gtgttaaaaa cggtctggag    960
cgtctgaaga aggcgatcaa atctggcggt ggtagcggtg gcggcggttc tggcggtggt    1020
ggcagcatcc tggatgctga ctacatcact gaagaaggca accggttat ccgtctgttc    1080 aaaaaagaga acggcgaatt taagattgag catgatcgca cctttcgtcc atacatttac    1140
gctctgctga agatgattc taagattgag gaagttaaaa aaatcactgc tgagcgccat    1200
ggcaagattg ttcgtatcgt tgatgcggaa aaggtagaaa agaaatttct gggcagacca    1260
atcaccgtgt ggagactgta tttcgaacat ccacaagatg ttccgactat cgcgagaaa    1320 attcgcgaac attctgcagt tgttgacatc ttcgaatacg atattccatt tgcaaagcgt    1380
tacctcatcg acaaaggcct gataccaatg gagggcgatg aagaactcaa gctcctggcg    1440
ttcgctatag caaccctcta tcacgaaggc gaagagtttg gtaaaggccc aattataatg    1500
atcagctatg cagatgaaga agaagcaaag gtgattactt ggaaaaaaat agatctccca    1560
tacgttgagg ttgtatcttc cgagcgcgag atgattaagc gctttctcaa aattatccgc    1620
gagaaggatc cggacattat cattacttat aacggcgact ctttgaccct cccatatctg    1680
gcgaaacgcg cagaaaaact cggtattaaa ctgactatcg ccgtgatgg ttccgagccg    1740 aagatgcagc gtatcggcga tatgaccgct gtagaagtta aggtcgtat ccatttcgac    1800 ctgtatcatg taattcgtcg tactattaac ctcccgactt acactctcga ggctgtatat    1860
```

```
gaagcaattt ttggtaagcc gaaggagaag gtatacgccg atgagattgc aaaggcgtgg    1920
gaaaccggtg agggcctcga gcgtgttgca aaatactcca tggaagatgc aaaggcgact    1980
tatgaactcg gcaaagaatt cttcccaatg gaagctcagc tctctcgcct ggttggccaa    2040
ccactgtggg atgtttctcg ttcttccacc ggtaacctcg tagagtggtt tctcctgcgc    2100
aaagcgtacg aacgcaacga actggctccg aacaagccag atgaacgtga gtatgaacgc    2160
cgtctccgcg agtcttacgc tggtggcttt gttaaagagc cagaaaaggg cctctgggaa    2220
aacatcgtgt ccctcgattt tcgcgctctg tatccgtcta ttatcattac ccacaacgtg    2280
tctccggata ctctcaaccg cgagggctgc agaaactatg atgttgctcc ggaagtaggc    2340
cacaagttct gcaaggactt cccgggcttt attccgtctc tcctgaaacg tctgctcgat    2400
gaacgccaaa agattaagac taaaatgaag gcgtcccagg atccgattga aaaataatg    2460 ctcgactatc gccaaagagc gattaaaatc ctcgcaaact cttattacgg ctattatggc    2520
tatgcaaaag cacgctggta ctgtaaggag tgtgctgagt ccgttactgc ttggggtcgc    2580
gaatacatcg agttcgtgtg gaaggagctc gaagaaaagt ttggctttaa agttctctac    2640
attgacactg atggtctcta tgcgactatt ccgggtggta agtctgagga aattaagaaa    2700
aaggctctag aatttgtgga ttacattaac gcgaagctcc cgggtctcct ggagctcgaa    2760
tatgaaggct tttataaacg cggcttcttc gttaccaaga gaaatatgc gctgattgat    2820 gaagaaggca aaattattac tcgtggtctc gagattgtgc gccgtgattg gagcgaaatt    2880
gcgaaagaaa ctcaagctag agttctcgag gctattctca acacggcaa cgttgaagaa    2940 gctgtgagaa ttgtaaaaga gtaacccaa agctctcta aatatgaaat tccgccagag    3000
aagctcgcga tttatgagca gattactcgc ccgctgcatg agtataaggc gattggtccg    3060
cacgtggctg ttgcaaagag actggctgct aaaggcgtga aaattaaacc gggtatggta    3120
attggctaca ttgtactccg cggcgatggt ccgattagca accgtgcaat tctagctgag    3180
gaatacgatc cgagaaagca caagtatgac gcagaatatt acattgagaa ccaggtgctc    3240
ccggcggtac tccgtattct ggagggtttt ggctaccgta aggaagacct ccgctggcaa    3300
aagactaaac agactggcct cacttcttgg ctcaacatta aaaaatccgg taccggcggt    3360
ggcggtgcaa ccgtaaagtt caagtacaaa ggcgaagaaa aagaggtaga catctccaag    3420
atcaagaaag tatggcgtgt gggcccaatg atctccttca cctacgacga gggcggtggc    3480
aagaccggcc gtggtgcggt aagcgaaaag gacgcgccga aggagctgct gcagatgctg    3540
gagaagcaga aagcggccgc actcgagcac caccaccacc accactgaga tccggctgct    3600
aa                                                                  3602
```

<210> SEQ ID NO 6
<211> LENGTH: 3227
<212> TYPE: DNA
<213> ORGANISM: Artificial Sequence
<220> FEATURE:
<223> OTHER INFORMATION: synthetic full length codon-optimized Da FEN1-
       polymerase-Sso7d fusion DNA polymerase, fusion protein #2,
       Archaeon Desulfurococcus amylolyticus flap endonuclease (Da FEN1)
       fused to Sulfolobus solfataricus Sso7d

<400> SEQUENCE: 6

```
atgggcgtgc cgatcggtga atcatccca cgtaaagaaa tcgagctgga gaacctgtac      60
ggtaaaaaaa ttgctatcga cgctctcaac gccatttacc agttcctgtc aactatccgt    120
cagaaagacg gcactccgct catggatagc aagggtcgta ttacctctca cctgtccggc    180
```

```
ctgttctacc gtacgatcaa tctgatggaa gcagggatta aaccggtcta tgtgttcgat      240
ggcgaaccgc cagagttcaa aaagaaagag ttggaaaaac gccgtgaagc acgtgaagaa      300
gcggaagaaa aatggcgtga agctctggaa aaaggcgaaa tcgaagaagc gcgtaaatac      360
gcccagcgtg cgaccgtgt caatgaaatg ctgatcgaag acgccaaaaa actgctggaa       420
ttgatgggta tccctatcgt gcaggctcca tctgaaggcg aagctcaagc ggcgtatatg      480
gccgcaaaag gctctgttta tgcgtctgct tcccaagatt acgactccct gctgtttggt      540
gcaccgcgcc tggtgcgtaa cctgaccatc acgggtaagc gtaagttgcc gggtaagaac      600
gtttatgtgg aaattaaacc tgaactgatt attctggaag aggtcctgaa agagctgaaa      660
ctgacacgcg aaaaactgat tgaactggct atcctggttg gcacagacta cacccaggc      720 ggtatcaaag catcggtct gaaaaaagcg cttgaaatcg tgcgtcacag taaagatccg      780
ctggctaagt ttcagaaaca gagcgacgtg gacctgtatg caattaaaga gttcttcctg      840
aaccctccgg ttactgataa ctacaacctg gttttggcgcg atccagacga ggagggtatc     900
ctgaaatttc tgtgtgatga acacgatttc tccgaggaac gtgttaaaaa cggtctggag      960
cgtctgaaga aggcgatcaa atctggcggt ggtagcggtg gcggcggttc tggcggtggt     1020
ggcagcatac caatggaggg cgatgaagaa ctcaagctcc tggcgttcgc tatagcaacc     1080
ctctatcacg aaggcgaaga gtttggtaaa ggcccaatta taatgatcag ctatgcagat     1140
gaagaagaag caaaggtgat tacttggaaa aaaatagatc tcccatacgt tgaggttgta     1200
tcttccgagc gcgagatgat taagcgcttt ctcaaaatta tccgcgagaa ggatccggac     1260
attatcatta cttataacgg cgactctttt gacctcccat atctggcgaa acgcgcagaa     1320
aaactcggta ttaaactgac tatcggccgt gatggttccg agccgaagat gcagcgtatc     1380
ggcgatatga ccgctgtaga agttaagggt cgtatccatt cgacctgta tcatgtaatt     1440 cgtcgtacta ttaacctccc gacttacact ctcgaggctg tatatgaagc aattttttggt     1500 aagccgaagg agaaggtata cgccgatgag attgcaaagg cgtgggaaac cggtgagggc     1560
ctcgagcgtg ttgcaaaata ctccatggaa gatgcaaagg cgacttatga actcggcaaa     1620
gaattcttcc aatgaaagc tcagctctct cgcctggttg ccaaccact gtgggatgtt     1680 tctcgttctt ccaccggtaa cctcgtagag tggtttctcc tgcgcaaagc gtacgaacgc     1740
aacgaactgg ctccgaacaa gccagatgaa cgtgagtatg aacgccgtct ccgcgagtct     1800
tacgctggtg gctttgttaa agagccagaa aagggcctct gggaaaacat cgtgtccctc     1860
gattttcgcg ctctgtatcc gtctattatc attacccaca acgtgtctcc ggatactctc     1920
aaccgcgagg gctgcagaaa ctatgatgtt gctccggaag taggccacaa gttctgcaag     1980
gacttcccgg gctttattcc gtctctcctg aaacgtctgc tcgatgaacg ccaaaagatt     2040
aagactaaaa tgaaggcgtc ccaggatccg attgaaaaaa taatgctcga ctatcgccaa     2100
agagcgatta aaatcctcgc aaactcttat tacggctatt atggctatgc aaaagcacgc     2160
tggtactgta aggagtgtgc tgagtccgtt actgcttggg gtcgcgaata catcgagttc     2220
gtgtggaagg agctcgaaga aaagtttggc tttaaagttc tctacattga cactgatggt     2280
ctctatgcga ctattccggg tggtaagtct gaggaaatta agaaaaaggc tctagaattt     2340
gtggattaca ttaacgcgaa gctcccgggt ctcctggagc tcgaatatga aggcttttat     2400
aaacgcggct tcttcgttac caagaagaaa tatgcgctga ttgatgaaga aggcaaaatt     2460
attactcgtg gtctcgagat tgtgcgccgt gattggagcg aaattgcgaa agaaactcaa     2520
```

| | |
|---|---|
| gctagagttc tcgaggctat tctcaaacac ggcaacgttg aagaagctgt gagaattgta | 2580 |
| aaagaagtaa cccaaaagct ctctaaatat gaaattccgc cagagaagct cgcgatttat | 2640 |
| gagcagatta ctcgcccgct gcatgagtat aaggcgattg gtccgcacgt ggctgttgca | 2700 |
| aagagactgg ctgctaaagg cgtgaaaatt aaaccgggta tggtaattgg ctacattgta | 2760 |
| ctccgcggcg atggtccgat tagcaaccgt gcaattctag ctgaggaata cgatccgaga | 2820 |
| aagcacaagt atgacgcaga atattacatt gagaaccagg tgctcccggc ggtactccgt | 2880 |
| attctggagg gttttggcta ccgtaaggaa gacctccgct ggcaaaagac taaacagact | 2940 |
| ggcctcactt cttggctcaa cattaaaaaa tccggtaccg gcggtggcgg tgcaaccgta | 3000 |
| aagttcaagt acaaaggcga agaaaaagag gtagacatct ccaagatcaa gaaagtatgg | 3060 |
| cgtgtgggcc caatgatctc cttcacctac gacgagggcg gtggcaagac cggccgtggt | 3120 |
| gcggtaagcg aaaaggacgc gccgaaggag ctgctgcaga tgctggagaa gcagaaagcg | 3180 |
| gccgcactcg agcaccacca ccaccaccac tgagatccgg ctgctaa | 3227 |

<210> SEQ ID NO 7
<211> LENGTH: 3680
<212> TYPE: DNA
<213> ORGANISM: Artificial Sequence
<220> FEATURE:
<223> OTHER INFORMATION: synthetic full length codon-optimized Pfu FEN1-
     polymerase (USD minus)-Sso7d fusion DNA polymerase, fusion protein
     #3, Archaeon Pyrococcus furiosus flap endonuclease (Pfu FEN1)
     without uracil sensing domain (USD) fused to Sulfolobus
     solfataricus Sso7d

<400> SEQUENCE: 7

| | |
|---|---|
| atgggtgtag acctgaaaga cattatcccg ggtgaggcga agactgtgat cgaagacctg | 60 |
| cgtatcctgc acggtaagat cattgtcatt gacggtttata acgcgctgta tcagttcctg | 120 |
| gctgctatcc gccaaccgga cggtactccg ctgatggata caacggtcg tattaccagc | 180 |
| catctgtctg gtctctttta tcgtaccatc aacatcgttg aagcgggtat caaaccagta | 240 |
| tatgtatttg atggtaaacc gccggaactg aaagcgcgcg aaattgagcg tcgtaaagcc | 300 |
| gttaaagaag aagccgcgaa aaagtatgaa gaagcagttc agtcgggtga tcttgaactg | 360 |
| gcgcgccgtt acgccatgat gagcgcgaaa ctgacagagg aaatggttcg tgacgcgaaa | 420 |
| tctctgctgg atgcgatggg catcccgtgg gtacaggccc cggctgaagg cgaggcgcag | 480 |
| gctgcgtata tcgttaaaaa aggtgacgct tacgcttccg cttcccagga ctatgattct | 540 |
| ctgctgttcg gttcgccgaa actggtgcgt aaccttacca tctctggccg tcgtaagctg | 600 |
| ccacgtaaga acgaatacgt ggaagtaaag ccggaactga ttgaactgga taaactgcta | 660 |
| gtccagctgg gcatcaccct ggaaaacctg atcgacatcg gtattctgct ggggacggat | 720 |
| tacaacccgg atggcttcga aggtatcggt ccaaaaaaag cactgcagct ggtgaaagcc | 780 |
| tatggtgcca ttgaaaaaat cccgaaaccg atcctgaaat cccgatcga gttgacgtt | 840 |
| attgctatca aaaatattt tctgcagccg caggttaccg caactatcg catcgaatgg | 900 |
| cacaccccgg accgggatgc cgtcaaacgt atcctggtcg acgaacatga cttttccatc | 960 |
| gaccgtgtat cgacggcgct ggaacgctac gtaaaagcgt tcaaagaaaa cattcgtggt | 1020 |
| gaacagaaag gcctgtctaa gtggttctcc aagccgaaat ctggcggtgg tagcggtggc | 1080 |
| ggcggttctg gcggtggtgg cagcatcctg atgctgact acatcactga agaaggcaaa | 1140 |
| ccggttatcc gtctgttcaa aaaagagaac ggcgaattta agattgagca tgatcgcacc | 1200 |
| tttcgtccat acatttacgc tctgctgaaa gatgattcta agattgagga agttaaaaaa | 1260 |

```
atcactgctg agcgccatgg caagattgtt cgtatcgttg atgcggaaaa ggtagaaaag    1320
aaatttctgg gcagaccaat caccgtgtgg agactgtatt cgaacatcc acaagatgtt    1380
ccgactattc gcgagaaaat tcgcgaacat tctgcagttg ttgacatctt cgaatacgat    1440
attccatttg caaagcgtta cctcatcgac aaaggcctga taccaatgga gggcgatgaa    1500
gaactcaagc tcctggcgtt cgctatagca accctctatc acgaaggcga agagtttggt    1560
aaaggcccaa ttataatgat cagctatgca gatgaagaag aagcaaaggt gattacttgg    1620
aaaaaaatag atctcccata cgttgaggtt gtatcttccg agcgcgagat gattaagcgc    1680
tttctcaaaa ttatccgcga gaaggatccg gacattatca ttacttataa cggcgactct    1740
tttgacctcc catatctggc gaaacgcgca gaaaaactcg gtattaaact gactatcggc    1800
cgtgatggtt ccgagccgaa gatgcagcgt atcggcgata tgaccgctgt agaagttaag    1860
ggtcgtatcc atttcgacct gtatcatgta attcgtcgta ctattaaccc cccgacttac    1920
actctcgagg ctgtatatga agcaattttt ggtaagccga aggagaaggt atacgccgat    1980
gagattgcaa aggcgtggga accggtgagg ggcctcgagc gtgttgcaaa atactccatg    2040
gaagatgcaa aggcgactta tgaactcggc aaagaattct cccaatggga agctcagctc    2100
tctcgcctgg ttggccaacc actgtgggat gtttctcgtt cttccaccgg taacctcgta    2160
gagtggtttc cctgcgcaa agcgtacgaa cgcaacgaac tggctccgaa caagccagat    2220
gaacgtgagt atgaacgccg tctccgcgag tcttacgctg gtggctttgt taagagcca    2280
gaaaagggcc tctgggaaaa catcgtgtcc ctcgattttc gcgctctgta tccgtctatt    2340
atcattaccc acaacgtgtc tccggatact ctcaaccgcg agggctgcag aaactatgat    2400
gttgctccgg aagtaggcca caagttctgc aaggacttcc cgggctttat tccgtctctc    2460
ctgaaacgtc tgctcgatga acgccaaaag attaagacta aaatgaaggc gtcccaggat    2520
ccgattgaaa aaataatgct cgactatcgc caaagagcga ttaaaatcct cgcaaactct    2580
tattacggct attatggcta tgcaaaagca cgctggtact gtaaggagtg tgctgagtcc    2640
gttactgctt ggggtcgcga atacatcgag ttcgtgtgga aggagctcga agaaaagttt    2700
ggctttaaag ttctctacat tgacactgat ggtctctatg cgactattcc gggtggtaag    2760
tctgaggaaa ttaagaaaaa ggctctagaa tttgtggatt acattaacgc gaagctcccg    2820
ggtctcctgg agctcgaata tgaaggcttt tataaacgcg gcttcttcgt taccaagaag    2880
aaatatgcgc tgattgatga agaaggcaaa attattactc gtggtctcga gattgtgcgc    2940
cgtgattgga gcgaaattgc gaaagaaact caagctagtt ttctcgaggc tattctcaaa    3000
cacggcaacg ttgaagaagc tgtgagaatt gtaaagaag taacccaaaa gctctctaaa    3060
tatgaaattc cgccagagaa gctcgcgatt tatgagcaga ttactcgccc gctgcatgag    3120
tataaggcga ttggtccgca cgtggctgtt gcaaagagac tggctgctaa aggcgtgaaa    3180
attaaaccgg gtatggtaat tggctacatt gtactccgcg gcgatggtcc gattagcaac    3240
cgtgcaattc tagctgagga atacgatccg agaaagcaca gtatgacgc agaatattac    3300
attgagaacc aggtgctccc ggcggtactc cgtattctgg agggttttgg ctaccgtaag    3360
gaagacctcc gctggcaaaa gactaaacag actggcctca cttcttggct caacattaaa    3420
aaatccggta ccggcggtgg cggtgcaacc gtaaagttca gtacaaagg cgaagaaaaa    3480
gaggtagaca tctccaagat caagaaagta tggcgtgtgg gcccaatgat ctccttcacc    3540
tacgacgagg gcggtggcaa gaccggccgt ggtgcggtaa gcgaaaagga cgcgccgaag    3600
```

| gagctgctgc agatgctgga gaagcagaaa gcggccgcac tcgagcacca ccaccaccac | 3660 |
| cactgagatc cggctgctaa | 3680 |

<210> SEQ ID NO 8
<211> LENGTH: 3305
<212> TYPE: DNA
<213> ORGANISM: Artificial Sequence
<220> FEATURE:
<223> OTHER INFORMATION: synthetic full length codon-optimized Da FEN1-
polymerase (USD minus)-Sso7d fusion DNA polymerase, fusion protein
4, Archaeon Desulfurococcus amylolyticus flap endonuclease (Da
FEN1) without uracil sensing domain (USD) fused to Sso7d

<400> SEQUENCE: 8

| atgggtgtag acctgaaaga cattatcccg ggtgaggcga agactgtgat cgaagacctg | 60 |
| cgtatcctgc acgtaagat cattgtcatt gacggttata acgcgctgta tcagttcctg | 120 |
| gctgctatcc gccaaccgga cggtactccg ctgatggata caacggtcg tattaccagc | 180 |
| catctgtctg gtctcttta tcgtaccatc aacatcgttg aagcgggtat caaaccagta | 240 |
| tatgtatttg atggtaaacc gccggaactg aaagcgcgcg aaattgagcg tcgtaaagcc | 300 |
| gttaaagaag aagccgcgaa aaagtatgaa gaagcagttc agtcgggtga tcttgaactg | 360 |
| gcgcgccgtt acgccatgat gagcgcgaaa ctgacagagg aaatggttcg tgacgcgaaa | 420 |
| tctctgctgg atgcgatggg catcccgtgg gtacaggccc cggctgaagg cgaggcgcag | 480 |
| gctgcgtata tcgttaaaaa aggtgacgct tacgcttccg cttcccagga ctatgattct | 540 |
| ctgctgttcg gttcgccgaa actggtgcgt aaccttacca tctctggccg tgtaagctg | 600 |
| ccacgtaaga acgaatacgt ggaagtaaag ccggaactga ttgaactgga taaactgcta | 660 |
| gtccagctgg gcatcaccct ggaaaacctg atcgacatcg gtattctgct ggggacggat | 720 |
| tacaacccgg atggcttcga aggtatcggt ccaaaaaag cactgcagct ggtgaaagcc | 780 |
| tatggtggca ttgaaaaaat cccgaaaccg atcctgaaat ccccgatcga agttgacgtt | 840 |
| attgctatca aaaaatattt tctgcagccg caggttaccg acaactatcg catcgaatgg | 900 |
| cacaccccgg accggatgc cgtcaaacgt atcctggtcg acgaacatga cttttccatc | 960 |
| gaccgtgtat cgacggcgct ggaacgctac gtaaaagcgt tcaaagaaaa cattcgtggt | 1020 |
| gaacagaaag gcctgtctaa gtggttctcc aagccgaaat ctggcggtgg tagcggtggc | 1080 |
| ggcggttctg gcgtggtgg cagcatacca atggagggcg atgaagaact caagctcctg | 1140 |
| gcgttcgcta tagcaaccct ctatcacgaa ggcgaagagt ttggtaaagg cccaattata | 1200 |
| atgatcagct atgcagatga agaagaagca aaggtgatta cttggaaaaa aatagatctc | 1260 |
| ccatacgttg aggttgtatc ttccgagcgc gagatgatta gcgctttct caaaattatc | 1320 |
| cgcgagaagg atccggacat tatcattact tataacggcg actcttttga cctcccatat | 1380 |
| ctggcgaaac gcgcagaaaa actcggtatt aaactgacta tcggccgtga tggttccgag | 1440 |
| ccgaagatgc agcgtatcgg cgatatgacc gctgtagaag ttaagggtcg tatccatttc | 1500 |
| gacctgtatc atgtaattcg tcgtactatt aacctcccga cttacactct cgaggctgta | 1560 |
| tatgaagcaa tttttggtaa gccgaaggag aaggtatacg ccgatgagat tgcaaaggcg | 1620 |
| tgggaaaccg gtgagggcct cgagcgtgtt gcaaatatact ccatgaaga tgcaaaggcg | 1680 |
| acttatgaac tcggcaaaga attcttccca atggaagctc agctctctcg cctggttggc | 1740 |
| caaccactgt gggatgttc tcgttcttcc accggtaacc tcgtagagtg gtttctcctg | 1800 |
| cgcaaagcgt acgaacgcaa cgaactggct ccgaacaagc cagatgaacg tgagtatgaa | 1860 |

```
cgccgtctcc gcgagtctta cgctggtggc tttgttaaag agccagaaaa gggcctctgg   1920
gaaaacatcg tgtccctcga ttttcgcgct ctgtatccgt ctattatcat acccacaac    1980 gtgtctccgg atactctcaa ccgcgagggc tgcagaaact atgatgttgc tccggaagta   2040
ggccacaagt tctgcaagga cttcccgggc tttattccgt ctctcctgaa cgtctgctc    2100 gatgaacgcc aaaagattaa gactaaaatg aaggcgtccc aggatccgat tgaaaaaata   2160
atgctcgact atcgccaaag agcgattaaa atcctcgcaa actcttatta cggctattat   2220
ggctatgcaa aagcacgctg gtactgtaag gagtgtgctg agtccgttac tgcttggggt   2280
cgcgaataca tcgagttcgt gtggaaggag ctcgaagaaa agtttggctt aaagttctc    2340 tacattgaca ctgatggtct ctatgcgact attccgggtg gtaagtctga ggaaattaag   2400
aaaaaggctc tagaatttgt ggattacatt aacgcgaagc tcccgggtct cctggagctc   2460
gaatatgaag ctttttataa acgcggcttc ttcgttacca agaagaaata tgcgctgatt   2520
gatgaagaag gcaaaattat tactcgtggt ctcgagattg tgcgccgtga ttggagcgaa   2580
attgcgaaag aaactcaagc tagagttctc gaggctattc tcaaacacgg caacgttgaa   2640
gaagctgtga gaattgtaaa agaagtaacc caaaagctct ctaaatatga aattccgcca   2700
gagaagctcg cgatttatga gcagattact cgcccgctgc atgagtataa ggcgattggt   2760
ccgcacgtgg ctgttgcaaa gagactggct gctaaaggcg tgaaaattaa accgggtatg   2820
gtaattggct acattgtact ccgcggcgat ggtccgatta gcaaccgtgc aattctagct   2880
gaggaatacg atccgagaaa gcacaagtat gacgcagaat attacattga gaaccaggtg   2940
ctcccggcgg tactccgtat tctggagggt tttggctacc gtaaggaaga cctccgctgg   3000
caaaagacta acagactgg cctcacttct tggctcaaca ttaaaaaatc cggtaccggc   3060
ggtggcggtg caaccgtaaa gttcaagtac aaaggcgaag aaaaagaggt agacatctcc   3120
aagatcaaga agtatggcg tgtgggccca atgatctcct tcacctacga cgagggcggt   3180
ggcaagaccg gccgtggtgc ggtaagcgaa aaggacgcgc cgaaggagct gctgcagatg   3240
ctggagaagc agaaagcggc cgcactcgag caccaccacc accaccactg agatccggct   3300
gctaa                                                               3305
```

<210> SEQ ID NO 9
<211> LENGTH: 1059
<212> TYPE: DNA
<213> ORGANISM: Artificial Sequence
<220> FEATURE:
<223> OTHER INFORMATION: synthetic full length codon-optimized Da
      FEN1-polymerase (USD minus)-Sso7d fusion DNA
      polymerase, Archaeon Desulfurococcus amylolyticus
      flap endonuclease (Da FEN1)

<400> SEQUENCE: 9

```
atgggtgtag acctgaaaga cattatcccg ggtgaggcga agactgtgat cgaagacctg    60
cgtatcctgc acggtaagat cattgtcatt gacggttata cgcgctgta tcagttcctg   120 gctgctatcc gccaaccgga cggtactccg ctgatggata caacggtcg tattaccagc   180 catctgtctg gtctcttttta tcgtaccatc aacatcgttg aagcgggtat caaaccagta   240
tatgtatttg atggtaaacc gccggaactg aaagcgcgcg aaattgagcg tcgtaaagcc   300
gttaaagaag aagccgcgaa aaagtatgaa gaagcagttc agtcgggtga tcttgaactg   360
gcgcgccgtt acgccatgat gagcgcgaaa ctgacagagg aaatggttcg tgacgcgaaa   420
tctctgctgg atgcgatggg catcccgtgg gtacaggccc cggctgaagg cgaggcgcag   480
```

-continued

```
gctgcgtata tcgttaaaaa aggtgacgct tacgcttccg cttcccagga ctatgattct    540
ctgctgttcg gttcgccgaa actggtgcgt aaccttacca tctctggccg tcgtaagctg    600
ccacgtaaga acgaatacgt ggaagtaaag ccggaactga ttgaactgga taaactgcta    660
gtccagctgg gcatcaccct ggaaaacctg atcgacatcg gtattctgct ggggacggat    720
tacaacccgg atggcttcga aggtatcggt ccaaaaaaag cactgcagct ggtgaaagcc    780
tatggtggca ttgaaaaaat cccgaaaccg atcctgaaat ccccgatcga agttgacgtt    840
attgctatca aaaatatttt tctgcagccg caggttaccg acaactatcg catcgaatgg    900
cacaccccgg accggatgc cgtcaaacgt atcctggtcg acgaacatga cttttccatc    960
gaccgtgtat cgacggcgct ggaacgctac gtaaaagcgt tcaagaaaaa cattcgtggt   1020
gaacagaaag gcctgtctaa gtggttctcc aagccgaaa                          1059
```

<210> SEQ ID NO 10
<211> LENGTH: 353
<212> TYPE: PRT
<213> ORGANISM: Artificial Sequence
<220> FEATURE:
<223> OTHER INFORMATION: synthetic Da FEN1 polymerase, Archaeon
      Desulfurococcus amylolyticus flap endonuclease (Da FEN1)

<400> SEQUENCE: 10

```
Met Gly Val Asp Leu Lys Asp Ile Ile Pro Gly Glu Ala Lys Thr Val
1               5                   10                  15

Ile Glu Asp Leu Arg Ile Leu His Gly Lys Ile Ile Val Ile Asp Gly
            20                  25                  30

Tyr Asn Ala Leu Tyr Gln Phe Leu Ala Ala Ile Arg Gln Pro Asp Gly
        35                  40                  45

Thr Pro Leu Met Asp Asn Asn Gly Arg Ile Thr Ser His Leu Ser Gly
    50                  55                  60

Leu Phe Tyr Arg Thr Ile Asn Ile Val Glu Ala Gly Ile Lys Pro Val
65                  70                  75                  80

Tyr Val Phe Asp Gly Lys Pro Pro Glu Leu Lys Ala Arg Glu Ile Glu
                85                  90                  95

Arg Arg Lys Ala Val Lys Glu Glu Ala Ala Lys Lys Tyr Glu Glu Ala
            100                 105                 110

Val Gln Ser Gly Asp Leu Glu Leu Ala Arg Arg Tyr Ala Met Met Ser
        115                 120                 125

Ala Lys Leu Thr Glu Glu Met Val Arg Asp Ala Lys Ser Leu Leu Asp
    130                 135                 140

Ala Met Gly Ile Pro Trp Val Gln Ala Pro Ala Glu Gly Glu Ala Gln
145                 150                 155                 160

Ala Ala Tyr Ile Val Lys Lys Gly Asp Ala Tyr Ala Ser Ala Ser Gln
                165                 170                 175

Asp Tyr Asp Ser Leu Leu Phe Gly Ser Pro Lys Leu Val Arg Asn Leu
            180                 185                 190

Thr Ile Ser Gly Arg Arg Lys Leu Pro Arg Lys Asn Glu Tyr Val Glu
        195                 200                 205

Val Lys Pro Glu Leu Ile Glu Leu Asp Lys Leu Leu Val Gln Leu Gly
    210                 215                 220

Ile Thr Leu Glu Asn Leu Ile Asp Ile Gly Ile Leu Leu Gly Thr Asp
225                 230                 235                 240

Tyr Asn Pro Asp Gly Phe Glu Gly Ile Gly Pro Lys Lys Ala Leu Gln
                245                 250                 255
```

```
Leu Val Lys Ala Tyr Gly Gly Ile Glu Lys Ile Pro Lys Pro Ile Leu
            260                 265                 270

Lys Ser Pro Ile Glu Val Asp Val Ile Ala Ile Lys Lys Tyr Phe Leu
        275                 280                 285

Gln Pro Gln Val Thr Asp Asn Tyr Arg Ile Glu Trp His Thr Pro Asp
    290                 295                 300

Pro Asp Ala Val Lys Arg Ile Leu Val Asp Glu His Asp Phe Ser Ile
305                 310                 315                 320

Asp Arg Val Ser Thr Ala Leu Glu Arg Tyr Val Lys Ala Phe Lys Glu
                325                 330                 335

Asn Ile Arg Gly Glu Gln Lys Gly Leu Ser Lys Trp Phe Ser Lys Pro
            340                 345                 350

Lys

<210> SEQ ID NO 11
<211> LENGTH: 45
<212> TYPE: DNA
<213> ORGANISM: Artificial Sequence
<220> FEATURE:
<223> OTHER INFORMATION: synthetic linker between Da FEN1 and
      Pfu/DeepVent hybrid DNA polymerase

<400> SEQUENCE: 11
tctggcggtg gtagcggtgg cggcggttct ggcggtggtg gcagc              45

<210> SEQ ID NO 12
<211> LENGTH: 15
<212> TYPE: PRT
<213> ORGANISM: Artificial Sequence
<220> FEATURE:
<223> OTHER INFORMATION: synthetic linker between Da FEN1 and
      Pfu/DeepVent hybrid DNA polymerase

<400> SEQUENCE: 12

Ser Gly Gly Gly Ser Gly Gly Gly Ser Gly Gly Gly Gly Ser
1               5                   10                  15

<210> SEQ ID NO 13
<211> LENGTH: 357
<212> TYPE: DNA
<213> ORGANISM: Artificial Sequence
<220> FEATURE:
<223> OTHER INFORMATION: synthetic Pfu/DeepVent hybrid DNA polymerase
      uracil-sensing domain (USD)

<400> SEQUENCE: 13
atcctggatg ctgactacat cactgaagaa ggcaaaccgg ttatccgtct gttcaaaaaa    60
gagaacggcg aatttaagat tgagcatgat cgcacctttc gtccatacat ttacgctctg   120
ctgaaagatg attctaagat tgaggaagtt aaaaaaatca ctgctgagcg ccatggcaag   180
attgttcgta tcgttgatgc ggaaaaggta gaaagaaat ttctgggcag accaatcacc    240
gtgtggagac tgtatttcga acatccacaa gatgttccga ctattcgcga gaaaattcgc   300
gaacattctg cagttgttga catcttcgaa tacgatattc catttgcaaa gcgttac      357

<210> SEQ ID NO 14
<211> LENGTH: 375
<212> TYPE: DNA
<213> ORGANISM: Artificial Sequence
<220> FEATURE:
<223> OTHER INFORMATION: synthetic Pfu/DeepVent hybrid DNA polymerase
      uracil-sensing domain (USD) plus nucleotides removed in USD minus
      construct
```

<400> SEQUENCE: 14

```
atcctggatg ctgactacat cactgaagaa ggcaaaccgg ttatccgtct gttcaaaaaa      60
gagaacggcg aatttaagat tgagcatgat cgcacctttc gtccatacat ttacgctctg     120
ctgaaagatt attctaagat tgaggaagtt aaaaaaatca ctgctgagcg ccatggcaag     180
attgttcgta tcgttgatgc ggaaaaggta gaaagaaat ttctgggcag accaatcacc      240
gtgtggagac tgtatttcga acatccacaa gatgttccga ctattcgcga gaaaattcgc     300
gaacattctg cagttgttga catcttcgaa tacgatattc catttgcaaa gcgttacctc     360
atcgacaaag gcctg                                                      375
```

<210> SEQ ID NO 15
<211> LENGTH: 1944
<212> TYPE: DNA
<213> ORGANISM: Artificial Sequence
<220> FEATURE:
<223> OTHER INFORMATION: synthetic Pfu/DeepVent hybrid DNA polymerase without uracil-sensing domain (USD)

<400> SEQUENCE: 15

```
ataccaatgg agggcgatga agaactcaag ctcctggcgt tcgctatagc aaccctctat      60
cacgaaggcg aagagtttgg taaaggccca attataatga tcagctatgc agatgaagaa     120
gaagcaaagg tgattacttg gaaaaaaata gatctcccat acgttgaggt tgtatcttcc     180
gagcgcgaga tgattaagcg ctttctcaaa attatccgcg agaaggatcc ggacattatc     240
attacttata acgcgactc tttttgacctc ccatatctgg cgaaacgcgc agaaaaactc    300
ggtattaaac tgactatcgg ccgtgatggt tccgagccga agatgcagcg tatcggcgat     360
atgaccgctg tagaagttaa gggtcgtatc catttcgacc tgtatcatgt aattcgtcgt     420
actattaacc tcccgactta cactctcgag gctgtatatg aagcaatttt tggtaagccg     480
aaggagaagg tatacgccga tgagattgca aaggcgtggg aaaccggtga gggcctcgag     540
cgtgttgcaa atactccat ggaagatgca aaggcgactt atgaactcgg caagaattc      600
ttcccaatgg aagctcagct ctctcgcctg gttggccaac cactgtggga tgtttctcgt     660
tcttccaccg gtaacctcgt agagtggttt ctcctgcgca aagcgtacga acgcaacgaa     720
ctggctccga caagccaga tgaacgtgag tatgaacgcc gtctccgcga gtcttacgct     780
ggtggctttg ttaaagagcc agaaaagggc ctctgggaaa acatcgtgtc cctcgatttt     840
cgcgctctgt atccgtctat tatcattacc acaacgtgt ctccggatac tctcaaccgc     900
gagggctgca gaaactatga tgttgctccg gaagtaggcc acaagttctg caaggacttc     960
ccgggcttta ttccgtctct cctgaaacgt ctgctcgatg aacgccaaaa gattaagact    1020
aaaatgaagg cgtcccagga tccgattgaa aaaataatgc tcgactatcg ccaaagagcg    1080
attaaaatcc tcgcaaactc ttattacggc tattatggct atgcaaaagc acgctggtac    1140
tgtaaggagt gtgctgagtc cgttactgct tggggtcgcg aatacatcga gttcgtgtgg    1200
aaggagctcg aagaaaagtt tggctttaaa gttctctaca ttgacactga tggtctctat    1260
gcgactattc cggtggtaa gtctgaggaa attaagaaaa aggctctaga atttgtggat    1320
tacattaacg cgaagctccc gggtctcctg gagctcgaat atgaaggctt ttataaacgc    1380
ggcttcttcg ttaccaagaa gaaatatgcg ctgattgatg aagaaggcaa aattattact    1440
cgtggtctcg agattgtgcg ccgtgattgg agcgaaattg cgaaagaaac tcaagctaga    1500
gttctcgagg ctattctcaa acacggcaac gttgaagaag ctgtgagaat tgtaaaagaa    1560
```

```
gtaacccaaa agctctctaa atatgaaatt ccgccagaga agctcgcgat ttatgagcag    1620
attactcgcc cgctgcatga gtataaggcg attggtccgc acgtggctgt tgcaaagaga    1680
ctggctgcta aaggcgtgaa aattaaaccg ggtatggtaa ttggctacat tgtactccgc    1740
ggcgatggtc cgattagcaa ccgtgcaatt ctagctgagg aatacgatcc gagaaagcac    1800
aagtatgacg cagaatatta cattgagaac caggtgctcc cggcggtact ccgtattctg    1860
gagggttttg gctaccgtaa ggaagacctc cgctggcaaa agactaaaca gactggcctc    1920
acttcttggc tcaacattaa aaaa                                           1944

<210> SEQ ID NO 16
<211> LENGTH: 2319
<212> TYPE: DNA
<213> ORGANISM: Artificial Sequence
<220> FEATURE:
<223> OTHER INFORMATION: synthetic Pfu/DeepVent hybrid DNA polymerase
      with uracil-sensing domain (USD)

<400> SEQUENCE: 16
atcctggatg ctgactacat cactgaagaa ggcaaaccgg ttatccgtct gttcaaaaaa      60
gagaacggcg aatttaagat tgagcatgat cgcacctttc gtccatacat ttacgctctg    120
ctgaaagatg attctaagat tgaggaagtt aaaaaaatca ctgctgagcg ccatggcaag    180
attgttcgta tcgttgatgc ggaaaaggta gaaaagaaat ttctgggcag accaatcacc    240
gtgtggagac tgtatttcga acatccacaa gatgttccga ctattcgcga gaaaattcgc    300
gaacattctg cagttgttga catcttcgaa tacgatattc catttgcaaa agcttaccte    360 atcgacaaag gcctgatacc aatggagggc gatgaagaac tcaagctcct ggcgttcgct    420
atagcaaccc tctatcacga aggcgaagag tttggtaaag ccccaattat aatgatcagc    480
tatgcagatg aagaagaagc aaaggtgatt acttggaaaa aaatagatct cccatacgtt    540
gaggttgtat cttccgagcg cgagatgatt aagcgctttc tcaaaattat ccgcgagaag    600
gatccggaca ttatcattac ttataacggc gactcttttg acctcccata tctggcgaaa    660
cgcgcagaaa aactcggtat taaactgact atcggccgtg atggttccga gccgaagatg    720
cagcgtatcg gcgatatgac cgctgtagaa gttaagggtc gtatccattt cgacctgtat    780
catgtaattc gtcgtactat taacctcccg acttacactc tcgaggctgt atatgaagca    840
attttttggt agccgaagga gaaggtatac gccgatgaga ttgcaaaggc gtgggaaacc    900
ggtgagggcc tcgagcgtgt tgcaaaatac tccatggaag atgcaaaggc gacttatgaa    960
ctcggcaaag aattcttccc aatggaagct cagctctctc gcctggttgg ccaaccactg    1020
tgggatgttt ctcgttcttc caccggtaac ctcgtagagt ggtttctcct gcgcaaagcg    1080
tacgaacgca acgaactggc tccgaacaag ccagatgaac gtgagtatga acgccgtctc    1140
cgcgagtctt acgctggtgg cttttgttaaa gagccagaaa agggcctctg gaaaacatc    1200 gtgtccctcg attttcgcgc tctgtatccg tctattatca ttacccacaa cgtgtctccg    1260
gatactctca accgcgaggg ctgcagaaac tatgatgttg ctccggaagt aggccacaag    1320
ttctgcaagg acttcccggg ctttattccg tctctcctga acgtctgct cgatgaacgc    1380 caaaagatta agactaaaat gaaggcgtcc caggatccga ttgaaaaaat aatgctcgac    1440
tatcgccaaa gagcgattaa aatcctcgca aactcttatt acggctatta tggctatgca    1500
aaagcacgct ggtactgtaa ggagtgtgct gagtccgtta ctgcttgggg tcgcgaatac    1560
atcgagttcg tgtggaagga gctcgaagaa aagtttggct ttaaagttct ctacattgac    1620
```

```
actgatggtc tctatgcgac tattccgggt ggtaagtctg aggaaattaa gaaaaaggct    1680
ctagaatttg tggattacat taacgcgaag ctcccgggtc tcctggagct cgaatatgaa    1740 ggctttata aacgcggctt cttcgttacc aagaagaaat atgcgctgat tgatgaagaa    1800
ggcaaaatta ttactcgtgg tctcgagatt gtgcgccgtg attggagcga aattgcgaaa    1860
gaaactcaag ctagagttct cgaggctatt ctcaaacacg caacgttga agaagctgtg    1920 agaattgtaa agaagtaac ccaaaagctc tctaaatatg aaattccgcc agagaagctc    1980
gcgatttatg agcagattac tcgcccgctg catgagtata aggcgattgg tccgcacgtg    2040
gctgttgcaa agagactggc tgctaaaggc gtgaaaatta accgggtat ggtaattggc     2100 tacattgtac tccgcggcga tggtccgatt agcaaccgtg caattctagc tgaggaatac    2160
gatccgagaa agcacaagta tgacgcagaa tattacattg agaaccaggt gctcccggcg    2220
gtactccgta ttctggaggg ttttggctac cgtaaggaag acctccgctg gcaaaagact    2280
aaacagactg gcctcacttc ttggctcaac attaaaaaa                          2319

<210> SEQ ID NO 17
<211> LENGTH: 21
<212> TYPE: DNA
<213> ORGANISM: Artificial Sequence
<220> FEATURE:
<223> OTHER INFORMATION: synthetic linker between DNA polymerase and
      Sso7d

<400> SEQUENCE: 17
tccggtaccg gcggtggcgg t                                               21

<210> SEQ ID NO 18
<211> LENGTH: 201
<212> TYPE: DNA
<213> ORGANISM: Artificial Sequence
<220> FEATURE:
<223> OTHER INFORMATION: synthetic linker between DNA polymerase and
      Sso7d

<400> SEQUENCE: 18
gcaaccgtaa agttcaagta caaaggcgaa gaaaaagagg tagacatctc caagatcaag     60
aaagtatggc gtgtgggccc aatgatctcc ttcacctacg acgagggcgg tggcaagacc    120
ggccgtggtg cggtaagcga aaaggacgcg ccgaaggagc tgctgcagat gctggagaag    180
cagaaagcgg ccgcactcga g                                              201

<210> SEQ ID NO 19
<211> LENGTH: 125
<212> TYPE: PRT
<213> ORGANISM: Artificial Sequence
<220> FEATURE:
<223> OTHER INFORMATION: synthetic DNA polymerase uracil-sensing domain
      (USD)

<400> SEQUENCE: 19

Ile Leu Asp Ala Asp Tyr Ile Thr Glu Glu Gly Lys Pro Val Ile Arg
  1               5                  10                  15

Leu Phe Lys Lys Glu Asn Gly Glu Phe Lys Ile Glu His Asp Arg Thr
             20                  25                  30

Phe Arg Pro Tyr Ile Tyr Ala Leu Leu Lys Asp Asp Ser Lys Ile Glu
         35                  40                  45

Glu Val Lys Lys Ile Thr Ala Glu Arg His Gly Lys Ile Val Arg Ile
     50                  55                  60
```

Val Asp Ala Glu Lys Val Lys Lys Phe Leu Gly Arg Pro Ile Thr
65                  70                  75                  80

Val Trp Arg Leu Tyr Phe Glu His Pro Gln Asp Val Pro Thr Ile Arg
                85                  90                  95

Glu Lys Ile Arg Glu His Ser Ala Val Val Asp Ile Phe Glu Tyr Asp
            100                 105                 110

Ile Pro Phe Ala Lys Arg Tyr Leu Ile Asp Lys Gly Leu
            115                 120                 125

<210> SEQ ID NO 20
<211> LENGTH: 648
<212> TYPE: PRT
<213> ORGANISM: Artificial Sequence
<220> FEATURE:
<223> OTHER INFORMATION: synthetic Pfu/DeepVent hybrid DNA polymerase
      (polymerase portion)

<400> SEQUENCE: 20

Ile Pro Met Glu Gly Asp Glu Glu Leu Lys Leu Leu Ala Phe Ala Ile
1               5                   10                  15

Ala Thr Leu Tyr His Glu Gly Glu Phe Gly Lys Gly Pro Ile Ile
            20                  25                  30

Met Ile Ser Tyr Ala Asp Glu Glu Ala Lys Val Ile Thr Trp Lys
        35                  40                  45

Lys Ile Asp Leu Pro Tyr Val Glu Val Ser Ser Glu Arg Glu Met
    50                  55                  60

Ile Lys Arg Phe Leu Lys Ile Ile Arg Glu Lys Asp Pro Asp Ile Ile
65                  70                  75                  80

Ile Thr Tyr Asn Gly Asp Ser Phe Asp Leu Pro Tyr Leu Ala Lys Arg
                85                  90                  95

Ala Glu Lys Leu Gly Ile Lys Leu Thr Ile Gly Arg Asp Gly Ser Glu
            100                 105                 110

Pro Lys Met Gln Arg Ile Gly Asp Met Thr Ala Val Glu Val Lys Gly
            115                 120                 125

Arg Ile His Phe Asp Leu Tyr His Val Ile Arg Arg Thr Ile Asn Leu
            130                 135                 140

Pro Thr Tyr Thr Leu Glu Ala Val Tyr Glu Ala Ile Phe Gly Lys Pro
145                 150                 155                 160

Lys Glu Lys Val Tyr Ala Asp Glu Ile Ala Lys Ala Trp Glu Thr Gly
                165                 170                 175

Glu Gly Leu Glu Arg Val Ala Lys Tyr Ser Met Glu Asp Ala Lys Ala
            180                 185                 190

Thr Tyr Glu Leu Gly Lys Glu Phe Phe Pro Met Glu Ala Gln Leu Ser
            195                 200                 205

Arg Leu Val Gly Gln Pro Leu Trp Asp Val Ser Arg Ser Ser Thr Gly
210                 215                 220

Asn Leu Val Glu Trp Phe Leu Leu Arg Lys Ala Tyr Glu Arg Asn Glu
225                 230                 235                 240

Leu Ala Pro Asn Lys Pro Asp Glu Arg Glu Tyr Glu Arg Arg Leu Arg
                245                 250                 255

Glu Ser Tyr Ala Gly Gly Phe Val Lys Glu Pro Glu Lys Gly Leu Trp
            260                 265                 270

Glu Asn Ile Val Ser Leu Asp Phe Arg Ala Leu Tyr Pro Ser Ile Ile
            275                 280                 285

Ile Thr His Asn Val Ser Pro Asp Thr Leu Asn Arg Glu Gly Cys Arg

```
            290                 295                 300
Asn Tyr Asp Val Ala Pro Glu Val Gly His Lys Phe Cys Lys Asp Phe
305                 310                 315                 320

Pro Gly Phe Ile Pro Ser Leu Leu Lys Arg Leu Leu Asp Glu Arg Gln
                325                 330                 335

Lys Ile Lys Thr Lys Met Lys Ala Ser Gln Asp Pro Ile Glu Lys Ile
            340                 345                 350

Met Leu Asp Tyr Arg Gln Arg Ala Ile Lys Ile Leu Ala Asn Ser Tyr
        355                 360                 365

Tyr Gly Tyr Tyr Gly Tyr Ala Lys Ala Arg Trp Tyr Cys Lys Glu Cys
    370                 375                 380

Ala Glu Ser Val Thr Ala Trp Gly Arg Glu Tyr Ile Glu Phe Val Trp
385                 390                 395                 400

Lys Glu Leu Glu Glu Lys Phe Gly Phe Lys Val Leu Tyr Ile Asp Thr
                405                 410                 415

Asp Gly Leu Tyr Ala Thr Ile Pro Gly Gly Lys Ser Glu Glu Ile Lys
            420                 425                 430

Lys Lys Ala Leu Glu Phe Val Asp Tyr Ile Asn Ala Lys Leu Pro Gly
        435                 440                 445

Leu Leu Glu Leu Glu Tyr Glu Gly Phe Tyr Lys Arg Gly Phe Phe Val
    450                 455                 460

Thr Lys Lys Lys Tyr Ala Leu Ile Asp Glu Glu Gly Lys Ile Ile Thr
465                 470                 475                 480

Arg Gly Leu Glu Ile Val Arg Arg Asp Trp Ser Glu Ile Ala Lys Glu
                485                 490                 495

Thr Gln Ala Arg Val Leu Glu Ala Ile Leu Lys His Gly Asn Val Glu
            500                 505                 510

Glu Ala Val Arg Ile Val Lys Glu Val Thr Gln Lys Leu Ser Lys Tyr
        515                 520                 525

Glu Ile Pro Pro Glu Lys Leu Ala Ile Tyr Glu Gln Ile Thr Arg Pro
    530                 535                 540

Leu His Glu Tyr Lys Ala Ile Gly Pro His Val Ala Val Ala Lys Arg
545                 550                 555                 560

Leu Ala Ala Lys Gly Val Lys Ile Lys Pro Gly Met Val Ile Gly Tyr
                565                 570                 575

Ile Val Leu Arg Gly Asp Gly Pro Ile Ser Asn Arg Ala Ile Leu Ala
            580                 585                 590

Glu Glu Tyr Asp Pro Arg Lys His Lys Tyr Asp Ala Glu Tyr Tyr Ile
        595                 600                 605

Glu Asn Gln Val Leu Pro Ala Val Leu Arg Ile Leu Glu Gly Phe Gly
    610                 615                 620

Tyr Arg Lys Glu Asp Leu Arg Trp Gln Lys Thr Lys Gln Thr Gly Leu
625                 630                 635                 640

Thr Ser Trp Leu Asn Ile Lys Lys
                645

<210> SEQ ID NO 21
<211> LENGTH: 7
<212> TYPE: PRT
<213> ORGANISM: Artificial Sequence
<220> FEATURE:
<223> OTHER INFORMATION: synthetic linker between DNA polymerase portion
      and Sso7d

<400> SEQUENCE: 21
```

Ser Gly Thr Gly Gly Gly Gly
 1               5

<210> SEQ ID NO 22
<211> LENGTH: 67
<212> TYPE: PRT
<213> ORGANISM: Artificial Sequence
<220> FEATURE:
<223> OTHER INFORMATION: synthetic Sso7d K28P mutant

<400> SEQUENCE: 22

Ala Thr Val Lys Phe Lys Tyr Lys Gly Glu Glu Lys Glu Val Asp Ile
 1               5                  10                  15

Ser Lys Ile Lys Lys Val Trp Arg Val Gly Pro Met Ile Ser Phe Thr
            20                  25                  30

Tyr Asp Glu Gly Gly Gly Lys Thr Gly Arg Gly Ala Val Ser Glu Lys
                35                  40                  45

Asp Ala Pro Lys Glu Leu Leu Gln Met Leu Lys Gln Lys Ala Ala
        50                  55                  60

Ala Leu Glu
65

<210> SEQ ID NO 23
<211> LENGTH: 981
<212> TYPE: DNA
<213> ORGANISM: Artificial Sequence
<220> FEATURE:
<223> OTHER INFORMATION: synthetic codon-optimized Archaeon Pyrococcus
      furiosus flap endonuclease (Pfu FEN1) with
      C-terminal signal sequence and PCNA-interacting
      protein (PIP-box) motif deleted

<400> SEQUENCE: 23
atgggcgtgc cgatcggtga atcatccca cgtaaagaaa tcgagctgga gaacctgtac      60
ggtaaaaaaa ttgctatcga cgctctcaac gccatttacc agttcctgtc aactatccgt    120
cagaaagacg gcactccgct catggatagc aagggtcgta ttacctctca cctgtccggc    180
ctgttctacc gtacgatcaa tctgatggaa gcaggatta aaccggtcta tgtgttcgat     240
ggcgaaccgc cagagttcaa aagaaagag ttggaaaaac gccgtgaagc acgtgaagaa     300
gcggaagaaa atggcgtga agctctggaa aaaggcgaaa tcgaagaagc gcgtaaatac    360
gcccagcgtg cgacccgtgt caatgaaatg ctgatcgaag acgccaaaaa actgctggaa   420
ttgatgggta tccctatcgt gcaggctcca tctgaaggcg aagctcaagc ggcgtatatg    480
gccgcaaaag gctctgttta tgcgtctgct tcccaagatt acgactccct gctgtttggt    540
gcaccgcgcc tggtgcgtaa cctgaccatc acgggtaagc gtaagttgcc gggtaagaac    600
gtttatgtgg aaattaaacc tgaactgatt attctggaag aggtcctgaa agagctgaaa    660
ctgacacgcg aaaaactgat tgaactggct atcctggttg gcacagacta caacccaggc    720
ggtatcaaag catcggtct gaaaaaagcg cttgaaatcg tgcgtcacag taaagatccg    780
ctggctaagt ttcagaaaca gagcgacgtg gacctgtatg caattaaaga gttcttcctg    840
aaccctccgg ttactgataa ctacaacctg gtttggcgcg atccagacga ggagggtatc    900
ctgaaatttc tgtgtgatga acacgatttc tccgaggaac gtgttaaaaa cggtctggag    960
cgtctgaaga aggcgatcaa a                                              981

<210> SEQ ID NO 24
<211> LENGTH: 327
<212> TYPE: PRT

<213> ORGANISM: Artificial Sequence
<220> FEATURE:
<223> OTHER INFORMATION: synthetic codon-optimized Archaeon Pyrococcus furiosus flap endonuclease (Pfu FEN1) with C-terminal signal sequence and PCNA-interacting protein (PIP-box) motif deleted

<400> SEQUENCE: 24

```
Met Gly Val Pro Ile Gly Glu Ile Ile Pro Arg Lys Glu Ile Glu Leu
 1               5                  10                  15
Glu Asn Leu Tyr Gly Lys Lys Ile Ala Ile Asp Ala Leu Asn Ala Ile
                20                  25                  30
Tyr Gln Phe Leu Ser Thr Ile Arg Gln Lys Asp Gly Thr Pro Leu Met
            35                  40                  45
Asp Ser Lys Gly Arg Ile Thr Ser His Leu Ser Gly Leu Phe Tyr Arg
        50                  55                  60
Thr Ile Asn Leu Met Glu Ala Gly Ile Lys Pro Val Tyr Val Phe Asp
65                  70                  75                  80
Gly Glu Pro Pro Glu Phe Lys Lys Lys Glu Leu Glu Lys Arg Arg Glu
                85                  90                  95
Ala Arg Glu Glu Ala Glu Glu Lys Trp Arg Glu Ala Leu Glu Lys Gly
            100                 105                 110
Glu Ile Glu Glu Ala Arg Lys Tyr Ala Gln Arg Ala Thr Arg Val Asn
        115                 120                 125
Glu Met Leu Ile Glu Asp Ala Lys Lys Leu Leu Glu Leu Met Gly Ile
    130                 135                 140
Pro Ile Val Gln Ala Pro Ser Glu Gly Glu Ala Gln Ala Ala Tyr Met
145                 150                 155                 160
Ala Ala Lys Gly Ser Val Tyr Ala Ser Ala Ser Gln Asp Tyr Asp Ser
                165                 170                 175
Leu Leu Phe Gly Ala Pro Arg Leu Val Arg Asn Leu Thr Ile Thr Gly
            180                 185                 190
Lys Arg Lys Leu Pro Gly Lys Asn Val Tyr Val Glu Ile Lys Pro Glu
        195                 200                 205
Leu Ile Ile Leu Glu Glu Val Leu Lys Glu Leu Lys Leu Thr Arg Glu
    210                 215                 220
Lys Leu Ile Glu Leu Ala Ile Leu Val Gly Thr Asp Tyr Asn Pro Gly
225                 230                 235                 240
Gly Ile Lys Gly Ile Gly Leu Lys Lys Ala Leu Glu Ile Val Arg His
                245                 250                 255
Ser Lys Asp Pro Leu Ala Lys Phe Gln Lys Gln Ser Asp Val Asp Leu
            260                 265                 270
Tyr Ala Ile Lys Glu Phe Phe Leu Asn Pro Pro Val Thr Asp Asn Tyr
        275                 280                 285
Asn Leu Val Trp Arg Asp Pro Asp Glu Glu Gly Ile Leu Lys Phe Leu
    290                 295                 300
Cys Asp Glu His Asp Phe Ser Glu Glu Arg Val Lys Asn Gly Leu Glu
305                 310                 315                 320
Arg Leu Lys Lys Ala Ile Lys
                325
```

<210> SEQ ID NO 25
<211> LENGTH: 119
<212> TYPE: PRT
<213> ORGANISM: Artificial Sequence
<220> FEATURE:
<223> OTHER INFORMATION: synthetic Pfu/DeepVent hybrid DNA polymerase uracil-sensing domain (USD)

<400> SEQUENCE: 25

Ile Leu Asp Ala Asp Tyr Ile Thr Glu Glu Gly Lys Pro Val Ile Arg
1               5                   10                  15

Leu Phe Lys Lys Glu Asn Gly Glu Phe Lys Ile Glu His Asp Arg Thr
            20                  25                  30

Phe Arg Pro Tyr Ile Tyr Ala Leu Leu Lys Asp Asp Ser Lys Ile Glu
        35                  40                  45

Glu Val Lys Lys Ile Thr Ala Glu Arg His Gly Lys Ile Val Arg Ile
    50                  55                  60

Val Asp Ala Glu Lys Val Glu Lys Lys Phe Leu Gly Arg Pro Ile Thr
65                  70                  75                  80

Val Trp Arg Leu Tyr Phe Glu His Pro Gln Asp Val Pro Thr Ile Arg
                85                  90                  95

Glu Lys Ile Arg Glu His Ser Ala Val Val Asp Ile Phe Glu Tyr Asp
            100                 105                 110

Ile Pro Phe Ala Lys Arg Tyr
        115

<210> SEQ ID NO 26
<211> LENGTH: 6
<212> TYPE: PRT
<213> ORGANISM: Artificial Sequence
<220> FEATURE:
<223> OTHER INFORMATION: synthetic amino acids deleted from DNA
      polymerase in addition to uracil-sensing domain (USD)

<400> SEQUENCE: 26

Leu Ile Asp Lys Gly Leu
1               5

<210> SEQ ID NO 27
<211> LENGTH: 64
<212> TYPE: PRT
<213> ORGANISM: Sulfolobus acidocaldarius
<220> FEATURE:
<223> OTHER INFORMATION: DNA-binding protein Sso7d/Ssh7A/SsoP2

<400> SEQUENCE: 27

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 28
<211> LENGTH: 64
<212> TYPE: PRT
<213> ORGANISM: Sulfolobus shibatae
<220> FEATURE:
<223> OTHER INFORMATION: DNA-binding protein Ssh7b

<400> SEQUENCE: 28

Met Val Thr Val Lys Phe Lys Tyr Lys Gly Glu Glu Lys Glu Val Asp
1               5                   10                  15

Thr Ser Lys Ile Lys Lys Val Trp Arg Val Gly Lys Met Ile Ser Phe
            20                  25                  30

```
Thr Tyr Asp Glu Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
 50                  55                  60

<210> SEQ ID NO 29
<211> LENGTH: 66
<212> TYPE: PRT
<213> ORGANISM: Sulfolobus acidocaldarius
<220> FEATURE:
<223> OTHER INFORMATION: DNA-binding protein Sac7d

<400> SEQUENCE: 29

Met Val Lys Val Lys Phe Lys Tyr Lys Gly Glu Glu Lys Glu Val Asp
  1               5                  10                  15

Thr Ser Lys Ile Lys Lys Val Trp Arg Val Gly Lys Met Val Ser Phe
                 20                  25                  30

Thr Tyr Asp Asp Asn Gly Lys Thr Gly Arg Gly Ala Val Ser Glu Lys
            35                  40                  45

Asp Ala Pro Lys Glu Leu Leu Asp Met Leu Ala Arg Ala Glu Arg Glu
 50                  55                  60

Lys Lys
 65

<210> SEQ ID NO 30
<211> LENGTH: 65
<212> TYPE: PRT
<213> ORGANISM: Sulfolobus acidocaldarius
<220> FEATURE:
<223> OTHER INFORMATION: Sulfolobus acidocaldarius strain DSM 639
      DNA-binding protein 7e, Sac7e

<400> SEQUENCE: 30

Met Ala Lys Val Arg Phe Lys Tyr Lys Gly Glu Glu Lys Glu Val Asp
  1               5                  10                  15

Thr Ser Lys Ile Lys Lys Val Trp Arg Val Gly Lys Met Val Ser Phe
                 20                  25                  30

Thr Tyr Asp Asp Asn Gly Lys Thr Gly Arg Gly Ala Val Ser Glu Lys
            35                  40                  45

Asp Ala Pro Lys Glu Leu Met Asp Met Leu Ala Arg Ala Glu Lys Lys
 50                  55                  60

Lys
 65

<210> SEQ ID NO 31
<211> LENGTH: 64
<212> TYPE: PRT
<213> ORGANISM: Sulfolobus tokodaii
<220> FEATURE:
<223> OTHER INFORMATION: Sulfolobus tokodaii strain 7 DNA-binding
      protein 7e, Sto7e

<400> SEQUENCE: 31

Met Val Thr Val Lys Phe Lys Tyr Lys Gly Glu Glu Lys Glu Val Asp
  1               5                  10                  15

Ile Ser Lys Ile Lys Lys Val Trp Arg Val Gly Lys Met Ile Ser Phe
                 20                  25                  30

Thr Tyr Asp Asp Asn Gly Lys Thr Gly Arg Gly Ala Val Ser Glu Lys
            35                  40                  45

Asp Ala Pro Lys Glu Leu Leu Gln Met Leu Glu Lys Ser Gly Lys Lys
```

<210> SEQ ID NO 32
<211> LENGTH: 3465
<212> TYPE: DNA
<213> ORGANISM: Artificial Sequence
<220> FEATURE:
<223> OTHER INFORMATION: synthetic pET29b-Taq 5'Exo-Linker-Pfu/DeepVent hybrid DNA polymerase-HisTag full construct

<400> SEQUENCE: 32

```
atgttaccct tgtttgaacc aaaaggtcgc gttttattag tagatggcca tcacttagcc      60
taccgtacat ttcacgcatt aaaaggactg actacctctc gtggcgaacc cgtccaagct     120
gtttatggat ttgctaaatc attattaaaa gccttaaaag aagatggtga tgccgttatt     180
gtagttttcg atgcaaaagc cccctcattt cggcacgagg cttatggtgg ttacaaagct     240
ggtcgtgcac cgacgcccga agattttccg cgccagttag cccttatcaa agaactcgta     300
gatttattag gtctcgcacg cttagaagtc cccggctacg aagcagatga cgttctcgcc     360
agccttgcca agaaagcaga aaaagaagga tatgaagtac gcatcctgac agccgacaaa     420
gacttatacc aactcctttc agatcgcatc cacgttttac atcccgaagg ctacttaatt     480
accccctgcat ggctgtggga aaatatggga ttacgtccgg atcaatgggc cgattaccgt     540
gctttaaccg gtgatgaatc agataacctg ccaggtgtta aagggattgg agaaaaaact     600
gcccgtaaat tgttagaaga tgggggctct ttggaagcac tgttaaaaaa ccttgatcgt     660
ctcaaacctg ccatccgcga aaaaattctg gcccacatgg atgacttaaa actgagctgg     720
gatctcgcta agttcgtac cgacttacct cttgaagttg attttgcaaa acgccgtgaa     780
cctgatcgtg aacgccttcg tgcatttctt gaacgtctgg aatttggctc cttgttacat     840
gaatttggcc tcttagaatc aggcggtggt agcggtggcg cggttctgg cggtggtggc     900
agcatcctgg atgctgacta catcactgaa gaaggcaaac cggttatccg tctgttcaaa     960
aaagagaacg gcgaatttaa gattgagcat gatcgcacct ttcgtccata catttacgct    1020
ctgctgaaag atgattctaa gattgaggaa gttaaaaaaa tcactgctga gcgccatggc    1080
aagattgttc gtatcgttga tgcggaaaag gtagaaaaga aatttctggg cagaccaatc    1140
accgtgtgga gactgtattt cgaacatcca caagatgttc cgactattcg cgagaaaatt    1200
cgcgaacatt ctgcagttgt tgacatcttc gaatacgata ttccatttgc aaagcgttac    1260
ctcatcgaca aaggcctgat accaatggag ggcgatgaag aactcaagct cctggcgttc    1320
gctatagcaa ccctctatca cgaaggcgaa gagtttggta aagcccaat tataatgatc    1380
agctatgcag atgaagaaga agcaaaggtg attacttgga aaaaaataga tctcccatac    1440
gttgaggttg tatcttccga gcgcgagatg attaagcgct ttctcaaaat tatccgcgag    1500
aaggatccgg acattatcat tacttataac ggcgactctt ttgacctccc atatctggcg    1560
aaacgcgcag aaaaactcgg tattaaactg actatcggcc gtgatggttc cgagccgaag    1620
atgcagcgta tcggcgatat gaccgctgta gaagttaagg gtcgtatcca tttcgacctg    1680
tatcatgtaa ttcgtcgtac tattaacctc ccgacttaca ctctcgaggc tgtatatgaa    1740
gcaatttttg gtaagccgaa ggagaaggta tacgccgatg agattgcaaa ggcgtgggaa    1800
accggtgagg gcctcgagcg tgttgcaaaa tactccatgg aagatgcaaa ggcgacttat    1860
gaactcggca agaattcttt cccaatgaa gctcagctct ctcgcctggt ggccaacca    1920
ctgtgggatg tttctcgttc ttccaccggt aacctcgtag agtggtttct cctgcgcaaa    1980
```

```
gcgtacgaac gcaacgaact ggctccgaac aagccagatg aacgtgagta tgaacgccgt    2040
ctccgcgagt cttacgctgg tggctttgtt aaagagccag aaaagggcct ctgggaaaac    2100
atcgtgtccc tcgattttcg cgctctgtat ccgtctatta tcattaccca caacgtgtct    2160
ccggatactc tcaaccgcga gggctgcaga aactatgatg ttgctccgga agtaggccac    2220
aagttctgca aggacttccc gggctttatt ccgtctctcc tgaaacgtct gctcgatgaa    2280
cgccaaaaga ttaagactaa aatgaaggcg tcccaggatc cgattgaaaa ataatgctc    2340 gactatcgcc aaagagcgat taaaatcctc gcaaactctt attacggcta ttatggctat    2400
gcaaaagcac gctggtactg taaggagtgt gctgagtccg ttactgcttg ggtcgcgaa    2460 tacatcgagt tcgtgtggaa ggagctcgaa gaaaagtttg gctttaaagt tctctacatt    2520
gacactgatg gtctctatgc gactattccg ggtggtaagt ctgaggaaat taagaaaaag    2580
gctctagaat ttgtggatta cattaacgcg aagctcccgg gtctcctgga gctcgaatat    2640
gaaggctttt ataaacgcgg cttcttcgtt accaagaaga aatatgcgct gattgatgaa    2700
gaaggcaaaa ttattactcg tggtctcgag attgtgcgcc gtgattggag cgaaattgcg    2760
aaagaaactc aagctagagt tctcgaggct attctcaaac acggcaacgt tgaagaagct    2820
gtgagaattg taaagaagt aacccaaaag ctctctaaat atgaaattcc gccagagaag    2880
ctcgcgattt atgagcagat tactcgcccg ctgcatgagt ataaggcgat tggtccgcac    2940
gtggctgttg caaagagact ggctgctaaa ggcgtgaaaa ttaaaccggg tatggtaatt    3000
ggctacattg tactccgcgg cgatggtccg attagcaacc gtgcaattct agctgaggaa    3060
tacgatccga gaaagcacaa gtatgacgca gaatattaca ttgagaacca ggtgctcccg    3120
gcggtactcc gtattctgga gggttttggc taccgtaagg aagacctccg ctggcaaaag    3180
actaaacaga ctggcctcac ttcttggctc aacattaaaa aatccggtac cggcggtggc    3240
ggtgcaaccg taaagttcaa gtacaaggc gaagaaaaag aggtagacat ctccaagatc    3300
aagaaagtat ggcgtgtggg cccaatgatc tccttcacct acgacgaggg cggtggcaag    3360
accggccgtg gtgcggtaag cgaaaaggac gcgccgaagg agctgctgca gatgctggag    3420
aagcagaaag cggccgcact cgagcaccac caccaccacc actga                    3465
```

<210> SEQ ID NO 33
<211> LENGTH: 1154
<212> TYPE: PRT
<213> ORGANISM: Artificial Sequence
<220> FEATURE:
<223> OTHER INFORMATION: synthetic pET29b-Taq 5'Exo-Linker-Pfu/DeepVent
      hybrid DNA polymerase-HisTag full construct

<400> SEQUENCE: 33

```
Met Leu Pro Leu Phe Glu Pro Lys Gly Arg Val Leu Leu Val Asp Gly
 1               5                  10                  15

His His Leu Ala Tyr Arg Thr Phe His Ala Leu Lys Gly Leu Thr Thr
                20                  25                  30

Ser Arg Gly Glu Pro Val Gln Ala Val Tyr Gly Phe Ala Lys Ser Leu
            35                  40                  45

Leu Lys Ala Leu Lys Glu Asp Gly Asp Ala Val Ile Val Val Phe Asp
        50                  55                  60

Ala Lys Ala Pro Ser Phe Arg His Glu Ala Tyr Gly Gly Tyr Lys Ala
 65                  70                  75                  80

Gly Arg Ala Pro Thr Pro Glu Asp Phe Pro Arg Gln Leu Ala Leu Ile
                85                  90                  95
```

-continued

```
Lys Glu Leu Val Asp Leu Leu Gly Leu Ala Arg Leu Glu Val Pro Gly
                100                 105                 110
Tyr Glu Ala Asp Asp Val Leu Ala Ser Leu Ala Lys Lys Ala Glu Lys
            115                 120                 125
Glu Gly Tyr Glu Val Arg Ile Leu Thr Ala Asp Lys Asp Leu Tyr Gln
        130                 135                 140
Leu Leu Ser Asp Arg Ile His Val Leu His Pro Gly Tyr Leu Ile
145                 150                 155                 160
Thr Pro Ala Trp Leu Trp Glu Lys Tyr Gly Leu Arg Pro Asp Gln Trp
                165                 170                 175
Ala Asp Tyr Arg Ala Leu Thr Gly Asp Glu Ser Asp Asn Leu Pro Gly
            180                 185                 190
Val Lys Gly Ile Gly Glu Lys Thr Ala Arg Lys Leu Leu Glu Glu Trp
        195                 200                 205
Gly Ser Leu Glu Ala Leu Leu Lys Asn Leu Asp Arg Leu Lys Pro Ala
    210                 215                 220
Ile Arg Glu Lys Ile Leu Ala His Met Asp Asp Leu Lys Leu Ser Trp
225                 230                 235                 240
Asp Leu Ala Lys Val Arg Thr Asp Leu Pro Leu Glu Val Asp Phe Ala
                245                 250                 255
Lys Arg Arg Glu Pro Asp Arg Glu Arg Leu Arg Ala Phe Leu Glu Arg
            260                 265                 270
Leu Glu Phe Gly Ser Leu Leu His Glu Phe Gly Leu Leu Glu Ser Gly
        275                 280                 285
Gly Gly Ser Gly Gly Gly Ser Gly Gly Gly Ser Ile Leu Asp
    290                 295                 300
Ala Asp Tyr Ile Thr Glu Glu Gly Lys Pro Val Ile Arg Leu Phe Lys
305                 310                 315                 320
Lys Glu Asn Gly Glu Phe Lys Ile Glu His Asp Arg Thr Phe Arg Pro
                325                 330                 335
Tyr Ile Tyr Ala Leu Leu Lys Asp Asp Ser Lys Ile Glu Glu Val Lys
            340                 345                 350
Lys Ile Thr Ala Glu Arg His Gly Lys Ile Val Arg Ile Val Asp Ala
        355                 360                 365
Glu Lys Val Glu Lys Lys Phe Leu Gly Arg Pro Ile Thr Val Trp Arg
    370                 375                 380
Leu Tyr Phe Glu His Pro Gln Asp Val Pro Thr Ile Arg Glu Lys Ile
385                 390                 395                 400
Arg Glu His Ser Ala Val Val Asp Ile Phe Glu Tyr Asp Ile Pro Phe
                405                 410                 415
Ala Lys Arg Tyr Leu Ile Asp Lys Gly Leu Ile Pro Met Glu Gly Asp
            420                 425                 430
Glu Glu Leu Lys Leu Leu Ala Phe Ala Ile Ala Thr Leu Tyr His Glu
        435                 440                 445
Gly Glu Glu Phe Gly Lys Gly Pro Ile Ile Met Ile Ser Tyr Ala Asp
    450                 455                 460
Glu Glu Glu Ala Lys Val Ile Thr Trp Lys Lys Ile Asp Leu Pro Tyr
465                 470                 475                 480
Val Glu Val Val Ser Ser Glu Arg Glu Met Ile Lys Arg Phe Leu Lys
                485                 490                 495
Ile Ile Arg Glu Lys Asp Pro Asp Ile Ile Thr Tyr Asn Gly Asp
            500                 505                 510
Ser Phe Asp Leu Pro Tyr Leu Ala Lys Arg Ala Glu Lys Leu Gly Ile
```

```
            515                 520                 525
Lys Leu Thr Ile Gly Arg Asp Gly Ser Glu Pro Lys Met Gln Arg Ile
    530                 535                 540

Gly Asp Met Thr Ala Val Glu Val Lys Gly Arg Ile His Phe Asp Leu
545                 550                 555                 560

Tyr His Val Ile Arg Arg Thr Ile Asn Leu Pro Thr Tyr Thr Leu Glu
                565                 570                 575

Ala Val Tyr Glu Ala Ile Phe Gly Lys Pro Lys Glu Lys Val Tyr Ala
                580                 585                 590

Asp Glu Ile Ala Lys Ala Trp Glu Thr Gly Glu Gly Leu Glu Arg Val
                595                 600                 605

Ala Lys Tyr Ser Met Glu Asp Ala Lys Ala Thr Tyr Glu Leu Gly Lys
    610                 615                 620

Glu Phe Phe Pro Met Glu Ala Gln Leu Ser Arg Leu Val Gly Gln Pro
625                 630                 635                 640

Leu Trp Asp Val Ser Arg Ser Ser Thr Gly Asn Leu Val Glu Trp Phe
                645                 650                 655

Leu Leu Arg Lys Ala Tyr Glu Arg Asn Glu Leu Ala Pro Asn Lys Pro
                660                 665                 670

Asp Glu Arg Glu Tyr Glu Arg Leu Arg Glu Ser Tyr Ala Gly Gly
                675                 680                 685

Phe Val Lys Glu Pro Glu Lys Gly Leu Trp Glu Asn Ile Val Ser Leu
    690                 695                 700

Asp Phe Arg Ala Leu Tyr Pro Ser Ile Ile Thr His Asn Val Ser
705                 710                 715                 720

Pro Asp Thr Leu Asn Arg Glu Gly Cys Arg Asn Tyr Asp Val Ala Pro
                725                 730                 735

Glu Val Gly His Lys Phe Cys Lys Asp Phe Pro Gly Phe Ile Pro Ser
                740                 745                 750

Leu Leu Lys Arg Leu Leu Asp Glu Arg Gln Lys Ile Lys Thr Lys Met
    755                 760                 765

Lys Ala Ser Gln Asp Pro Ile Glu Lys Ile Met Leu Asp Tyr Arg Gln
770                 775                 780

Arg Ala Ile Lys Ile Leu Ala Asn Ser Tyr Tyr Gly Tyr Gly Tyr
785                 790                 795                 800

Ala Lys Ala Arg Trp Tyr Cys Lys Glu Cys Ala Glu Ser Val Thr Ala
                805                 810                 815

Trp Gly Arg Glu Tyr Ile Glu Phe Val Trp Lys Glu Leu Glu Glu Lys
                820                 825                 830

Phe Gly Phe Lys Val Leu Tyr Ile Asp Thr Asp Gly Leu Tyr Ala Thr
    835                 840                 845

Ile Pro Gly Gly Lys Ser Glu Ile Lys Lys Ala Leu Glu Phe
850                 855                 860

Val Asp Tyr Ile Asn Ala Lys Leu Pro Gly Leu Leu Glu Leu Glu Tyr
865                 870                 875                 880

Glu Gly Phe Tyr Lys Arg Gly Phe Phe Val Thr Lys Lys Tyr Ala
                885                 890                 895

Leu Ile Asp Glu Glu Gly Lys Ile Thr Arg Gly Leu Glu Ile Val
                900                 905                 910

Arg Arg Asp Trp Ser Glu Ile Ala Lys Glu Thr Gln Ala Arg Val Leu
                915                 920                 925

Glu Ala Ile Leu Lys His Gly Asn Val Glu Glu Ala Val Arg Ile Val
    930                 935                 940
```

Lys Glu Val Thr Gln Lys Leu Ser Lys Tyr Glu Ile Pro Pro Glu Lys
945                 950                 955                 960

Leu Ala Ile Tyr Glu Gln Ile Thr Arg Pro Leu His Glu Tyr Lys Ala
                965                 970                 975

Ile Gly Pro His Val Ala Val Ala Lys Arg Leu Ala Ala Lys Gly Val
            980                 985                 990

Lys Ile Lys Pro Gly Met Val Ile Gly Tyr Ile Val Leu Arg Gly Asp
        995                 1000                1005

Gly Pro Ile Ser Asn Arg Ala Ile Leu Ala Glu Tyr Asp Pro Arg
    1010                1015                1020

Lys His Lys Tyr Asp Ala Glu Tyr Tyr Ile Glu Asn Gln Val Leu Pro
1025                1030                1035                1040

Ala Val Leu Arg Ile Leu Glu Gly Phe Gly Tyr Arg Lys Glu Asp Leu
                1045                1050                1055

Arg Trp Gln Lys Thr Lys Gln Thr Gly Leu Thr Ser Trp Leu Asn Ile
                1060                1065                1070

Lys Lys Ser Gly Thr Gly Gly Gly Ala Thr Val Lys Phe Lys Tyr
            1075                1080                1085

Lys Gly Glu Glu Lys Glu Val Asp Ile Ser Lys Ile Lys Lys Val Trp
    1090                1095                1100

Arg Val Gly Pro Met Ile Ser Phe Thr Tyr Asp Glu Gly Gly Gly Lys
1105                1110                1115                1120

Thr Gly Arg Gly Ala Val Ser Glu Lys Asp Ala Pro Lys Glu Leu Leu
                1125                1130                1135

Gln Met Leu Glu Lys Gln Lys Ala Ala Ala Leu Glu His His His His
                1140                1145                1150

His His

<210> SEQ ID NO 34
<211> LENGTH: 861
<212> TYPE: DNA
<213> ORGANISM: Artificial Sequence
<220> FEATURE:
<223> OTHER INFORMATION: synthetic pET29b-Taq 5'Exo-Linker-Pfu/DeepVent
      hybrid DNA polymerase-HisTag codon-optimized Taq 5'Exo domain

<400> SEQUENCE: 34
atgttaccct tgtttgaacc aaaaggtcgc gtttattatag tagatggcca tcacttagcc      60
taccgtacat ttcacgcatt aaaaggactg actacctctc gtggcgaacc cgtccaagct     120
gtttatggat ttgctaaatc attattaaaa gccttaaaag aagatggtga tgccgttatt     180
gtagttttcg atgcaaaagc ccctcattt cggcacgagg cttatggtgg ttacaaagct     240
ggtcgtgcac cgacgcccga agattttccg cgccagttag cccttatcaa agaactcgta     300
gatttattag gtctcgcacg cttagaagtc cccggctacg aagcagatga cgttctcgcc     360
agccttgcca agaaagcaga aaagaagga tatgaagtac gcatcctgac agccgacaaa     420
gacttatacc aactcctttc agatcgcatc acgttttac atcccgaagg ctacttaatt     480 accctgcat ggctgtggga aaaatatgga ttacgtccgg atcaatgggc cgattaccgt     540
gctttaaccg tgatgaatc agataacctg ccaggtgtta agggattgg agaaaaaact     600 gcccgtaaat tgttagaaga tggggctct ttggaagcac tgttaaaaaa ccttgatcgt     660
ctcaaacctg ccatccgcga aaaaattctg gcccacatgg atgacttaaa actgagctgg     720
gatctcgcta aagttcgtac cgacttacct cttgaagttg attttgcaaa acgccgtgaa     780
cctgatcgtg aacgccttcg tgcatttctt gaacgtctgg aatttggctc cttgttacat    840
gaatttggcc tcttagaatc a                                                861

```
<210> SEQ ID NO 35
<211> LENGTH: 287
<212> TYPE: PRT
<213> ORGANISM: Artificial Sequence
<220> FEATURE:
<223> OTHER INFORMATION: synthetic pET29b-Taq 5'Exo-Linker-Pfu/DeepVent
      hybrid DNA polymerase-HisTag Taq 5'Exo domain

<400> SEQUENCE: 35
```

Met Leu Pro Leu Phe Glu Pro Lys Gly Arg Val Leu Leu Val Asp Gly
 1               5                  10                  15

His His Leu Ala Tyr Arg Thr Phe His Ala Leu Lys Gly Leu Thr Thr
             20                  25                  30

Ser Arg Gly Glu Pro Val Gln Ala Val Tyr Gly Phe Ala Lys Ser Leu
         35                  40                  45

Leu Lys Ala Leu Lys Glu Asp Gly Asp Ala Val Ile Val Val Phe Asp
     50                  55                  60

Ala Lys Ala Pro Ser Phe Arg His Glu Ala Tyr Gly Gly Tyr Lys Ala
 65                  70                  75                  80

Gly Arg Ala Pro Thr Pro Glu Asp Phe Pro Arg Gln Leu Ala Leu Ile
                 85                  90                  95

Lys Glu Leu Val Asp Leu Leu Gly Leu Ala Arg Leu Glu Val Pro Gly
            100                 105                 110

Tyr Glu Ala Asp Asp Val Leu Ala Ser Leu Ala Lys Lys Ala Glu Lys
        115                 120                 125

Glu Gly Tyr Glu Val Arg Ile Leu Thr Ala Asp Lys Asp Leu Tyr Gln
    130                 135                 140

Leu Leu Ser Asp Arg Ile His Val Leu His Pro Glu Gly Tyr Leu Ile
145                 150                 155                 160

Thr Pro Ala Trp Leu Trp Glu Lys Tyr Gly Leu Arg Pro Asp Gln Trp
                165                 170                 175

Ala Asp Tyr Arg Ala Leu Thr Gly Asp Glu Ser Asp Asn Leu Pro Gly
            180                 185                 190

Val Lys Gly Ile Gly Glu Lys Thr Ala Arg Lys Leu Leu Glu Glu Trp
        195                 200                 205

Gly Ser Leu Glu Ala Leu Leu Lys Asn Leu Asp Arg Leu Lys Pro Ala
    210                 215                 220

Ile Arg Glu Lys Ile Leu Ala His Met Asp Asp Leu Lys Leu Ser Trp
225                 230                 235                 240

Asp Leu Ala Lys Val Arg Thr Asp Leu Pro Leu Glu Val Asp Phe Ala
                245                 250                 255

Lys Arg Arg Glu Pro Asp Arg Glu Arg Leu Arg Ala Phe Leu Glu Arg
            260                 265                 270

Leu Glu Phe Gly Ser Leu Leu His Glu Phe Gly Leu Leu Glu Ser
        275                 280                 285

```
<210> SEQ ID NO 36
<211> LENGTH: 42
<212> TYPE: DNA
<213> ORGANISM: Artificial Sequence
<220> FEATURE:
<223> OTHER INFORMATION: synthetic linker bbetween Taq 5'Exo domain and
      Pfu/DeepVent hybrid DNA polymerase

<400> SEQUENCE: 36
```

```
ggcggtggta gcggtggcgg cggttctggc ggtggtggca gc                        42
```

<210> SEQ ID NO 37
<211> LENGTH: 14
<212> TYPE: PRT
<213> ORGANISM: Artificial Sequence
<220> FEATURE:
<223> OTHER INFORMATION: synthetic linker between Taq 5'Exo domain and
      Pfu/DeepVent hybrid DNA polymerase

<400> SEQUENCE: 37

Gly Gly Gly Ser Gly Gly Gly Gly Ser Gly Gly Gly Gly Ser
1               5                   10

<210> SEQ ID NO 38
<211> LENGTH: 119
<212> TYPE: PRT
<213> ORGANISM: Artificial Sequence
<220> FEATURE:
<223> OTHER INFORMATION: synthetic Archaeon Pyrococcus furiosus (Pfu)
      DNA polymerase uracil-sensing domain (USD)

<400> SEQUENCE: 38

Ile Leu Asp Val Asp Tyr Ile Thr Glu Glu Gly Lys Pro Val Ile Arg
1               5                   10                  15

Leu Phe Lys Lys Glu Asn Gly Lys Phe Lys Ile Glu His Asp Arg Thr
            20                  25                  30

Phe Arg Pro Tyr Ile Tyr Ala Leu Leu Arg Asp Asp Ser Lys Ile Glu
        35                  40                  45

Glu Val Lys Lys Ile Thr Gly Glu Arg His Gly Lys Ile Val Arg Ile
    50                  55                  60

Val Asp Val Glu Lys Val Glu Lys Lys Phe Leu Gly Lys Pro Ile Thr
65                  70                  75                  80

Val Trp Lys Leu Tyr Leu Glu His Pro Gln Asp Val Pro Thr Ile Arg
                85                  90                  95

Glu Lys Val Arg Glu His Pro Ala Val Val Asp Ile Phe Glu Tyr Asp
            100                 105                 110

Ile Pro Phe Ala Lys Arg Tyr
        115

<210> SEQ ID NO 39
<211> LENGTH: 6
<212> TYPE: PRT
<213> ORGANISM: Artificial Sequence
<220> FEATURE:
<223> OTHER INFORMATION: synthetic 6-His epitope tag

<400> SEQUENCE: 39

His His His His His His
1               5

<210> SEQ ID NO 40
<211> LENGTH: 8
<212> TYPE: PRT
<213> ORGANISM: Artificial Sequence
<220> FEATURE:
<223> OTHER INFORMATION: synthetic anti-DYKDDDDK epitope tag

<400> SEQUENCE: 40

Asp Tyr Lys Asp Asp Asp Asp Lys
1               5

```
<210> SEQ ID NO 41
<211> LENGTH: 4
<212> TYPE: PRT
<213> ORGANISM: Artificial Sequence
<220> FEATURE:
<223> OTHER INFORMATION: synthetic DNA-dependent DNA polymerase II
      family B region of similarity I conserved tetrapeptide motif

<400> SEQUENCE: 41

Asp Thr Asp Ser
  1
```

FUSION POLYMERASES

CROSS-REFERENCE TO RELATED PATENT APPLICATIONS

The present application is a continuation of U.S. patent application Ser. No. 14/562,396 filed Dec. 5, 2014, which claims benefit of priority to U.S. Provisional Patent Application No. 61/912,981, filed Dec. 6, 2013 and U.S. Provisional Patent Application No. 62/006,409, filed Jun. 2, 2014, each of which are incorporated herein by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 094260-1063250_SEQ.TXT, created on Oct. 19, 2017, 106,649 bytes, machine format IBM-PC, MS-Windows operating system, is hereby incorporated by reference in its entirety for all purposes.

BACKGROUND OF THE INVENTION

Nucleic acid amplification reactions, such as polymerase chain reaction (PCR), are generally template-dependent reactions in which a desired nucleic acid sequence is amplified by treating separate complementary strands of a target nucleic acid with an excess of two oligonucleotide primers. The primers are extended to form complementary primer extension products which act as templates for synthesizing the desired nucleic acid sequence. In such processes, the nucleic acid sequence between the primers on the respective DNA strands is selectively amplified.

A variety of thermostable polymerases have been discovered that can be used in PCR. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerization and 3' to 5' exonuclease activity.

Taq polymerase has inherent polymerase and 5'-3' exonuclease activity, but does not have 3'-5' exonuclease ("proofreading") activity. Utilizing the inherent 5' to 3' exonuclease activity of Taq, it is possible to achieve PCR amplification and signal release from a target-specific fluorogenic probe (e.g., a "Taqman" probe). The 5' to 3' exonuclease activity of Taq cleaves the 5' terminus of a hybridized oligo probe to release both mono- and oligonucleotides. The probe is hydrolyzed during strand replication so that the accumulating fluorescent signal correlates with amplification.

Pfu DNA polymerase and other family B polymerases has superior thermostability, inhibitor tolerance, and proofreading properties compared to Taq DNA polymerase. Unlike Taq DNA polymerase, Pfu DNA polymerase possesses 3' to 5' exonuclease proofreading activity, meaning that it works its way along the DNA from the 5' end to the 3' end and corrects nucleotide-misincorporation errors. This means that Pfu DNA polymerase-generated PCR fragments will have fewer errors than Taq-generated PCR inserts. However, Pfu and other family B polymerases lack 5'-3' exonuclease activity and thus do not work in probe-based quantitative PCR methods such as those involving Taqman probes.

BRIEF SUMMARY OF THE INVENTION

Provided herein are polypeptides having at least polymerase activity and 5'-3' exonuclease activity, wherein the polypeptides ("fusion polypeptide") comprise a 5'-3' exonuclease domain linked to a heterologous polymerase that does not naturally have 5'-3' exonuclease activity. In some embodiments, the polymerase activity and 5'-3' exonuclease activity are thermostable.

In some embodiments, the heterologous polymerase is a family B polymerase. In some embodiments, the heterologous polymerase is derived from two parental polymerases.

In some embodiments, the 5'-3' exonuclease domain is a flap endonuclease 5'-3' exonuclease domain. In some embodiments, the 5'-3' exonuclease domain is a 5'-3' exonuclease domain from a polymerase.

In some embodiments, the polymerase comprises a uracil-sensing domain (USD). In some embodiments, the USD comprises one or more point mutation substantially eliminating uracil-sensing activity.

In some embodiments, the polymerase lacks at least 10 (e.g., at least 10, 20, 30, 40, 50, 60, 70, 80, 90, 100, 110, 120, or 125) amino acids of a native uracil-sensing domain (USD). In some embodiments, the uracil-sensing domain (USD) is removed or otherwise absent.

In some embodiments, the fusion polypeptide further comprises a heterologous sequence non-specific double-stranded or single-stranded DNA binding domain. In some embodiments, the heterologous sequence non-specific double stranded DNA binding domain comprises a Sso7 DNA binding domain or a Sso7-like DNA binding domain. In some embodiments, the heterologous sequence non-specific double stranded DNA binding domain substantially (e.g., at least 60%) identical to any of SEQ ID NOs: 27, 28, 29, 30, or 31.

In some embodiments, the 5'-3' exonuclease domain and the heterologous family B polymerase are linked by a linker. In some embodiments, the linker is an amino acid linker.

In some embodiments, the carboxyl terminus of the 5'-3' exonuclease domain is linked via a linker to the amino terminus of the family B polymerase. In some embodiments, the amino terminus of the 5'-3' exonuclease domain is linked via a linker to the carboxyl terminus of the family B polymerase.

In some embodiments, the polypeptide has 3'-5' exonuclease activity.

In some embodiments, the polypeptide substantially lacks 3'-5' exonuclease activity. In some embodiments, the polymerase comprises at least one point mutation that substantially eliminates 3'-5' exonuclease activity. In some embodiments, the polymerase comprises a deletion that substantially eliminates 3'-5' exonuclease activity.

In some embodiments, the polypeptide is bound to a reagent that prevents the polymerase activity until the polypeptide is heated.

In some embodiments, the reagent is one or more antibody or aptamer bound to the polymerase.

In some embodiments, the reagent is a reversible covalent chemical modification.

Also provided are kits comprising the fusion polypeptide and other components as described above or elsewhere herein. In some embodiments, the kit further comprises a reverse transcriptase.

Also provided are reaction mixtures, e.g., comprising the fusion polypeptide and other components as described above or elsewhere herein. In some embodiments, the reaction mixture further comprises a polynucleotide primer. In some embodiments, the reaction mixture comprises a sample nucleic acid. In some embodiments, the reaction mixture does not comprise a sample nucleic acid.

In some embodiments, the reaction mixture further comprises a reverse transcriptase.

In some embodiments, the reaction mixture further comprises dUTP and/or a nucleic acid template comprising incorporated uracil.

In some embodiments, the reaction mixture comprises at least one polynucleotide primer and at least one probe with a fluorophore and quencher that is hybridized to a target polynucleotide sequence, wherein during amplification of the target polynucleotide sequence the 5'-3' exonuclease activity releases the fluorophore from the probe, thereby generating fluorescent signal.

Also provided are nucleic acids comprising a polynucleotide encoding the fusion polypeptide as described above or elsewhere herein.

Also provided are methods of performing polymerase chain reaction (PCR) or other type (e.g., isothermal) of amplification. In some embodiments, the method comprises: contacting in an amplification reaction mixture the fusion polypeptide as described herein to a sample comprising nucleic acids under conditions to allow for amplification of a target sequence in the nucleic acids, if present; and detecting the presence or absence of amplified target sequence.

In some embodiments, the amplification reaction comprises at least one polynucleotide primer and at least one probe with a fluorophore and quencher that is hybridized to a target polynucleotide sequence, wherein during amplification of the target polynucleotide sequence the 5'-3' exonuclease activity releases the fluorophore from the probe, thereby generating fluorescent signal.

In some embodiments, the sample comprises one or more inhibitor of PCR. In some embodiments, the sample is crude sample that has not undergone nucleic acid purification. In some embodiments, the sample is blood or serum.

In some embodiments, the amplification reaction comprises dUTP and/or a nucleic acid template comprising incorporated uracil.

In some embodiments, the sample comprises a RNA target nucleic acid and the reaction mixture comprises a reverse transcriptase, and wherein the method further comprises: reverse transcribing the RNA target nucleic acid with the reverse transcriptase to generate a cDNA; and amplifying the cDNA with the polypeptide.

Also provided is a method of making the fusion polypeptide. In some embodiments, the method comprises incubating cells comprising a polynucleotide encoding the polypeptide under conditions to cause expression of the polypeptide in the cells; and purifying the expressed polypeptide.

Also provided are polypeptides having polymerase activity (e.g., thermostable polymerase activity), the polypeptide comprising a family B polymerase but lacking at least 10 amino acids of a native uracil-sensing domain (USD). In some embodiments, the uracil-sensing domain (USD) is absent.

In some embodiments, the polypeptide further comprises a heterologous sequence non-specific double stranded DNA binding domain. In some embodiments, the heterologous sequence non-specific double stranded DNA binding domain comprises a Sso7 DNA binding domain or a Sso7-like DNA binding domain.

Also provided is a kit comprising the polypeptide having polymerase activity (e.g., thermostable polymerase activity), the polypeptide comprising a family B polymerase but lacking at least 10 amino acids of a native uracil-sensing domain (USD).

Also provided are reaction mixtures comprising the polypeptide having polymerase activity (e.g., thermostable polymerase activity), the polypeptide comprising a family B polymerase but lacking at least 10 amino acids of a native uracil-sensing domain (USD).

In some embodiments, the reaction mixture further comprises a polynucleotide primer. In some embodiments, the reaction mixture comprises a sample nucleic acid. In some embodiments, the reaction mixture does not comprise a sample nucleic acid.

In some embodiments, the reaction mixture further comprises a reverse transcriptase.

In some embodiments, the reaction mixture further comprises dUTP and/or a nucleic acid template comprising incorporated uracil.

Also provided are nucleic acids comprising a polynucleotide encoding the polypeptide having polymerase activity (e.g., thermostable polymerase activity), the polypeptide comprising a family B polymerase but lacking at least 10 amino acids of a native uracil-sensing domain (USD).

Also provided are methods of performing polymerase chain reaction (PCR). In some embodiments, the method comprises: contacting in an amplification reaction mixture polypeptide having polymerase activity (e.g., thermostable polymerase activity) to a sample comprising nucleic acids under conditions to allow for amplification of a target sequence in the nucleic acids, if present, wherein the polypeptide comprises a family B polymerase but lacks at least 10, 20, 30, 40, 50, 60, 70, 80, 90, 100, 110, 120, or 125 amino acids of a native uracil-sensing domain (USD); and detecting the presence or absence of amplified target sequence.

In some embodiments, the amplification reaction comprises dUTP and/or a nucleic acid template comprising incorporated uracil.

In some embodiments, the sample comprises a RNA target nucleic acid and the reaction mixture comprises a reverse transcriptase, and wherein the method further comprises: reverse transcribing the RNA target nucleic acid with the reverse transcriptase to generate a cDNA; and amplifying the cDNA with the polypeptide.

Also provided are methods of making the polypeptide. In some embodiments, the method comprises incubating cells comprising a polynucleotide encoding the polypeptide under conditions to cause expression of the polypeptide in the cells; and purifying the expressed polypeptide.

Other aspects of the invention will be evident as described below.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "Sso7" or "Sso7 DNA binding domain" or "Sso7-like DNA binding domain" or "Sso7 domain" refers to nucleic acid and polypeptide polymorphic variants, alleles, mutants, and interspecies homologs that have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity to SEQ ID NO:27, 28, 29, 30, or 31. The term includes both full-length Sso7d polypeptides and fragments of the polypeptides that have sequence non-specific double-stranded binding activity. Sso7-like proteins include, but are not limited to, Sso7d, Sac7d and Sac7e.

"Domain" refers to a unit of a protein or protein complex, comprising a polypeptide subsequence, a complete polypeptide sequence, or a plurality of polypeptide sequences where that unit has a defined function.

"Heterologous", when used with reference to portions of a protein, indicates that the protein comprises two or more domains that are not found in the same relationship (e.g., do not occur in the same polypeptide) to each other in nature. Such a protein, e.g., a fusion protein, contains two or more domains from unrelated proteins arranged to make a new functional protein.

"Thermally stable polymerase activity" or "thermostable polymerase activity" of a polypeptide as used herein refers to enzyme activity that catalyzes polynucleotide synthesis by addition of nucleotide units to a nucleotide chain using DNA or RNA as a template and has an optimal activity at a temperature above 45° C., e.g., above 60° C.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. As discussed further herein, amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

A "template" refers to a polynucleotide sequence that comprises the polynucleotide to be amplified, flanked by primer hybridization sites. Thus, a "target template" comprises the target polynucleotide sequence flanked by hybridization sites for a 5' primer and a 3' primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

The terms "oligonucleotide" or "polynucleotide" or "nucleic acid" interchangeably refer to a polymer of monomers that can be corresponded to a ribose nucleic acid (RNA) or deoxyribose nucleic acid (DNA) polymer, or analog thereof. This includes polymers of nucleotides such as RNA and DNA, as well as modified forms thereof, peptide nucleic acids (PNAs), locked nucleic acids (LNA™), and the like. In certain applications, the nucleic acid can be a polymer that includes multiple monomer types, e.g., both RNA and DNA subunits.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., a carbon atom that is bound to a hydrogen atom, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "encoding" refers to a polynucleotide sequence encoding one or more amino acids. The term does not require a start or stop codon. An amino acid sequence can be encoded in any one of six different reading frames provided by a polynucleotide sequence.

The term "promoter" refers to regions or sequence located upstream and/or downstream from the start of transcription and which are involved in recognition and binding of RNA polymerase and other proteins to initiate transcription.

A "vector" refers to a polynucleotide, which when independent of the host chromosome, is capable replication in a host organism. Preferred vectors include plasmids and typically have an origin of replication. Vectors can comprise, e.g., transcription and translation terminators, transcription and translation initiation sequences, and promoters useful for regulation of the expression of the particular nucleic acid. Any of the polynucleotides described herein can be included in a vector.

A "DNA polymerase" or a "polymerase," as used herein, refers to an enzyme that performs template-directed synthesis of DNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis, Bacillus stearothermophilus*, and *Thermotoga maritime*, or modified versions thereof. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity over a specified region), when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared.

When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Accelrys), or by manual alignment and visual inspection.

Algorithms suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

BRIEF DESCRIPTION OF THE DRAWINGS

FIG. 1, upper portion: Probe based real-time PCR amplification curves of 100 ng to 100 pg cDNA input using qPCR reagent containing Taq DNA polymerase, which has intrinsic 5'-3' exonuclease activity. Cross labelled traces are no template control (NTC). A standard curve of Cq (signal take-off cycle) against input concentration is shown on the right. PCR efficiency in percentage is shown as E value.

FIG. 1, lower portion: Probe based real-time PCR amplification curves of 100 ng to 100 pg cDNA input using qPCR reagent containing Pfu-based DNA polymerase (a fusion polymerase of Sso7d and pfu/deepVent hybrid DNA polymerase), which lacks intrinsic 5'-3' exonuclease activity. Cross labelled traces are no template control (NTC). A standard curve of Cq (signal take-off cycle) against input concentration is shown on the right. PCR efficiency in percentage is shown as E value.

FIG. 2, upper portion: Probe based real-time PCR amplification curves of 100 ng to 100 pg cDNA input using qPCR reagent containing a fusion DNA polymerase of Pfu flap endonuclease 1 (Pfu FEN1) and Pfu-based DNA polymerase. Cross labelled traces are no template control (NTC). A standard curve of Cq (signal take-off cycle) against input concentration is shown on the right. PCR efficiency in percentage is shown as E value.

FIG. 2, lower portion: Probe based real-time PCR amplification curves of 100 ng to 100 pg cDNA input using qPCR reagent containing a fusion DNA polymerase of Pfu flap endonuclease 1 (Pfu FEN1) and uracil-sensing domain minus Pfu-based DNA polymerase. Cross labelled traces are no template control (NTC). A standard curve of Cq (signal take-off cycle) against input concentration is shown on the right. PCR efficiency in percentage is shown as E value.

FIG. 3, upper portion: Probe based real-time PCR amplification curves of 100 ng to 100 pg cDNA input using qPCR reagent containing a fusion DNA polymerase of Da flap endonuclease 1 (Da FEN1) and Pfu-based DNA polymerase. Cross labelled traces are no template control (NTC). A standard curve of Cq (signal take-off cycle) against input concentration is shown on the right. PCR efficiency in percentage is shown as E value.

FIG. 3, lower portion: Probe based real-time PCR amplification curves of 100 ng to 100 pg cDNA input using qPCR reagent containing a fusion DNA polymerase of Da flap endonuclease 1 (Da FEN1) and uracil-sensing domain minus Pfu-based DNA polymerase. Cross labelled traces are no template control (NTC). A standard curve of Cq (signal take-off cycle) against input concentration is shown on the right. PCR efficiency in percentage is shown as E value.

DETAILED DESCRIPTION OF THE INVENTION

I. Introduction

Figure 1:
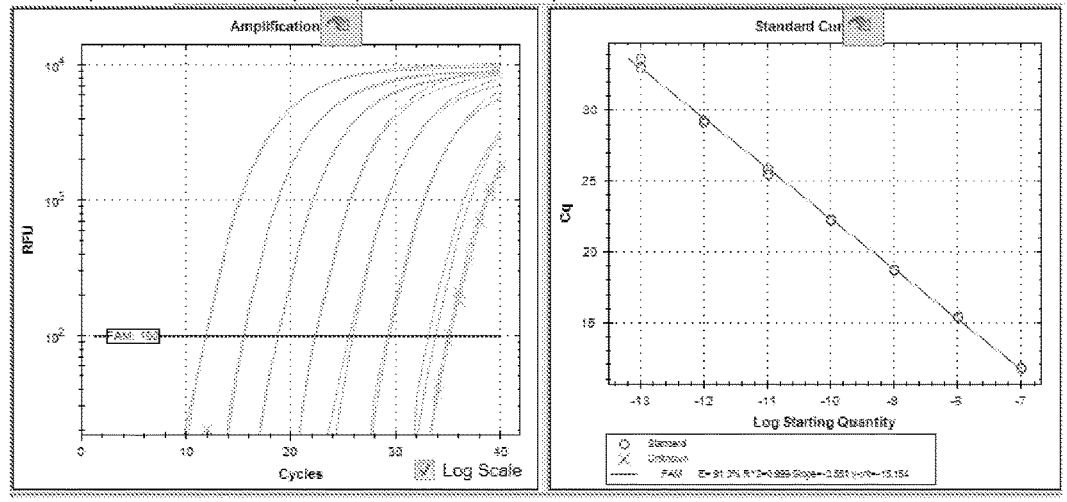
FIG. 1 illustrates results of quantitative detection of probe-based qPCR reactions using two different kinds of control polymerases.
Figure 1:
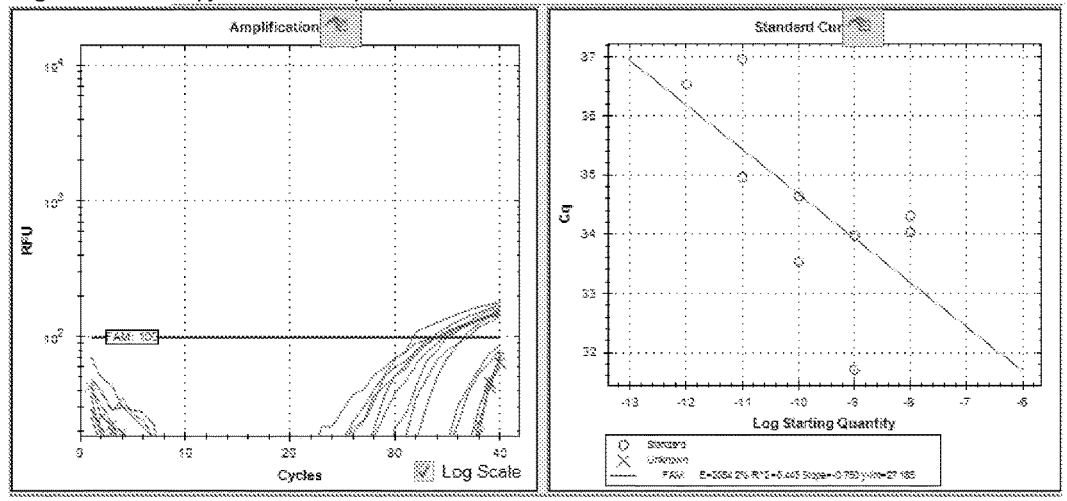
Figure 2:
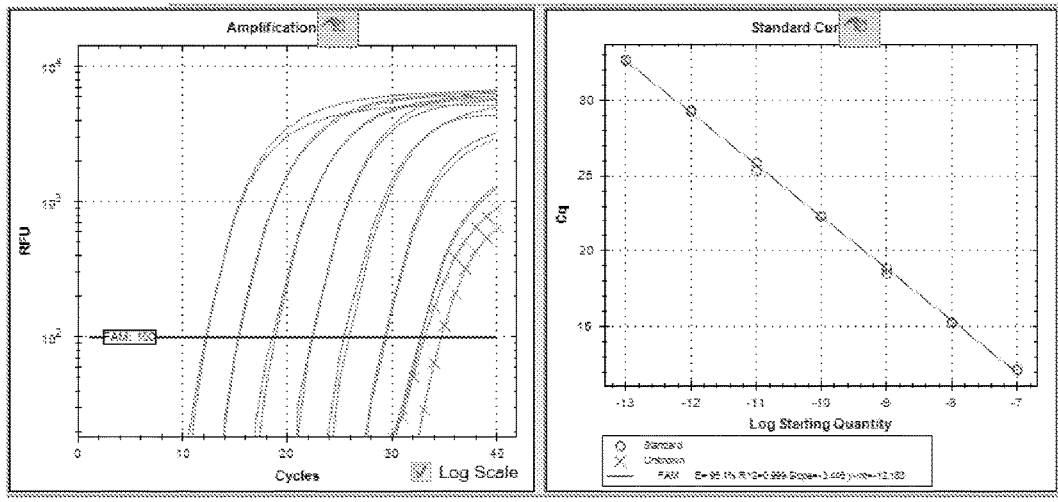
FIG. 2 illustrates results of quantitative detection of probe-based qPCR reactions using Pfu FEN1 5'-3' exonuclease domain fused to DNA polymerase (upper), and Pfu FEN1 5'-3' exonuclease domain fused to DNA polymerase lack of uracil-sensing domain (lower).
Figure 2:
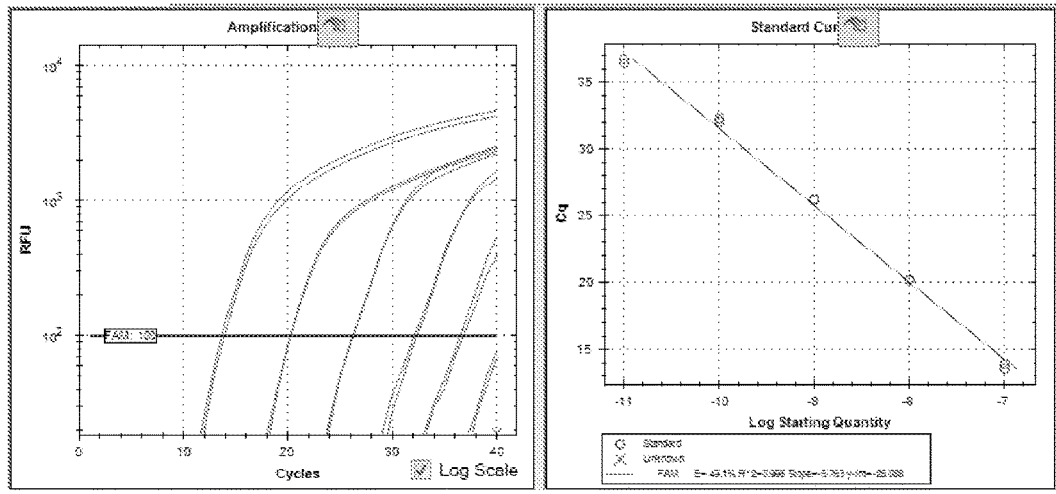

It has been surprisingly discovered that polymerases that do not naturally have a 5'-3' exonuclease activity can be fused with a heterologous 5'-3' exonuclease domain to generate a fusion protein that retains both polymerase and 5'-3' exonuclease activity. This discovery thus allows, for example, for use of family B polymerases and other polymerases that do not naturally have a 5'-3' exonuclease activity in probe-based quantitative PCR (qPCR) applications that rely on a polymerase having 5'-3' exonuclease activity. It is also expected that the fusion protein will retain the improved tolerance of inhibitors of family B polymerases (compared, for example, to the lesser inhibitor tolerance of family A polymerases such as Taq polymerase).

As demonstrated in the examples, 5'-3' exonuclease domains have been fused to the amino terminus of a family B polymerase via a linker and have been shown to have activity in probe-based qPCR methods. Also demonstrated in the example is the generation of a family B polymerase lacking the uracil-sensing domain (USD) and fused to a heterologous 5'-3' exonuclease domain. This demonstrates, for the first time to the inventor's knowledge, that a family B polymerase can retain polymerase activity without the presence (i.e., the structure) of the USD.

II. 5'-3' Exonuclease Domains

It is believed that any domain having 5'-3' exonuclease activity can be fused to a polymerase that does not naturally have a 5'-3' exonuclease activity. Generally, the 5'-3' exonuclease will be fused to the amino terminus of the polymerase, either directly or via a linker. Linkage of the 5'-3' exonuclease and the polymerase can be achieved by any method. A convenient way to link the 5'-3' exonuclease to the polymerase is via recombinant DNA techniques to generate a coding polynucleotide sequence encoding the fused protein and then expressing the protein from the polynucleotide in a cell or via in vitro translation.

A variety of domains having 5'-3' exonuclease activity are known and can be used in the fusion proteins as described herein. In some embodiments, the 5'-3' exonuclease domain is a flap endonuclease (FEN1) or a fragment thereof retaining 5'-3' exonuclease activity. FEN1 proteins are generally from Eukarya and Archea and possess 5'-3' exonuclease activity. A variety of FEN1 proteins (as well as active fragments or variants thereof) are known (see, e.g., Williams, et al., *J. Mol. Biol.* 371(1):34-38 (2007)) and can be used as the 5'-3' exonuclease domain as described herein. In some embodiments the FEN1 protein has thermostable 5'-3' exonuclease activity. Thermostable FEN1 proteins include, but are not limited to, the *Methanococcus jannaschii* FEN1 protein (see, e.g., Rao, et al., *J. Bacteriol.* 180(20):5406-5412 (1998)), the *Pyrococcus furiosus* FEN1 protein (see, e.g., Hosfield, et al., *Cell* 95:135-146 (1998)) or the *Desulfurococcus amylolyticus* FEN1 protein (see, e.g., Mase et al., *Acta Crystallographica Section F* F67:209-213 (2011), as well as active variants (e.g., substantially identical versions thereof) or fragments thereof. An exemplary active FEN1 protein fragment is a FEN1 protein that lacks a PCNA-interacting protein motif (PIP) box. PIP boxes are described in, e.g., Querol-Audi, et al., *Proc. Natl. Acad. Sci USA* 109(22):8528-8533 (2012). Exemplary thermostable FEN1 protein sequences include those substantially identical to SEQ ID NOs: 10 or 24.

In some embodiments, the 5'-3' exonuclease domain is from a heterologous polymerase. For example family A polymerases have 5'-3' activity and thus fragments of a family A polymerase can be used as the 5'-3' exonuclease domain. Conserved sites within the 5'-3' exonuclease domain of the *E. coli* polymerase (Pol I) has been described. See, e.g., Gutman et al., *Nucleic Acids Res.* 21(18):4406-7 (1993). The 5'-3' exonuclease domain of various thermostable polymerases have also been identified and separately expressed with retained activity. See, e.g., Choi et al., *Biotechnol. Letts.* 23:1647-52 (2001) and Kaiser et al., *J. Chem. Biol.* 274(30):21387-21394 (1999). An exemplary listing of sources of 5'-3' exonuclease domains useful in the protein fusions described herein include, but are not limited to, *Thermus thermophilus* (Tth) DNA polymerase, *Thermus aquaticus* (Taq) DNA polymerase, *Thermotoga neopolitana* (Tne) DNA polymerase, *Bacillus stearothermophilus* DNA polymerase, and *Thermotoga maritima* (Tma) DNA polymerase, and mutants, and variants (e.g., substantially identical versions thereof) and derivatives thereof. An exemplary Taq 5'-3' exonuclease domain is SEQ ID NO:35, or a substantially identical amino acid sequence thereof.

In some embodiments, the coding sequences of each polypeptide in a resulting fusion protein (e.g., the 5'-3' exonuclease domain and the polymerase and optionally the sequence non-specific DNA binding protein discussed further below) are directly joined at their amino- or carboxy-terminus via a peptide bond. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) *Gene* 40:39-46; Murphy et al. (1986) *Proc. Natl. Acad. Sci. USA* 83:8258-8262; U.S. Pat. Nos. 4,935,233 and 4,751,180, each of which is hereby incorporated by reference in its entirety for all purposes and in particular for all teachings related to linkers. The linker sequence may generally be from 1 to about 50 amino acids in length, e.g., 3, 4, 6, or 10 amino acids in length, but can be 100 or 200 amino acids in length. Linker sequences may not be required when the first and second polypeptides have non-essential N-terminal amino acid regions that can be used to separate the functional domains and prevent steric interference. In some embodiments, linker sequences of use in the present invention comprise an amino acid sequence according to SEQ ID NO: 12 or 21.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterobifunctional linkages.

Other methods of joining a DNA binding domain and polymerase domain include ionic binding by expressing negative and positive tails and indirect binding through antibodies and streptavidin-biotin interactions. See, e.g., Bioconjugate Techniques, Hermanson, Ed., Academic Press (1996).

As previously described, nucleic acids encoding the polymerase or DNA binding domains can be obtained using routine techniques in the field of recombinant genetics. Basic texts disclosing the general methods of use in this invention include Sambrook and Russell, Molecular Cloning, *A Laboratory Manual* (3rd ed. 2001); Kriegler, *Gene Transfer and Expression: A Laboratory Manual* (1990); and *Current Protocols in Molecular Biology* (Ausubel et al., eds., 1994-1999). Such nucleic acids may also be obtained through in vitro amplification methods such as those described herein and in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) C&EN 36-47; *The Journal Of NIH Research* (1991) 3: 81-94; Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117, each of which is incorporated by reference in its entirety for all purposes and in particular for all teachings related to amplification methods.

Modifications can additionally be made to the 5'-3' exonuclease domain (or the polymerase) without diminishing their biological activity. Some modifications may be made to facilitate the cloning, expression, or incorporation of a domain into a fusion protein. Such modifications can include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

The fusion polypeptides described herein can be expressed in a variety of host cells, including *E. coli*, other bacterial hosts, yeasts, filamentous fungi, and various higher eukaryotic cells such as the COS, CHO and HeLa cells lines and myeloma cell lines. Techniques for gene expression in microorganisms are described in, for example, Smith, *Gene Expression in Recombinant Microorganisms* (Bioprocess Technology, Vol. 22), Marcel Dekker, 1994.

There are many expression systems for producing the fusion polypeptides described herein that are known to those of ordinary skill in the art. See, e.g., *Gene Expression Systems*, Fernandex and Hoeffler, Eds. Academic Press, 1999; Sambrook and Russell, supra; and Ausubel et al, supra.) Typically, the polynucleotide that encodes the fusion polypeptide is placed under the control of a promoter that is functional in the desired host cell. Many different promoters are available and known to one of skill in the art, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived PL promoter and N-gene ribosome binding site (Shimatake et al., *Nature* (1981) 292: 128). The particular promoter system is not critical, any available promoter that functions in prokaryotes can be used. Standard bacterial expression vectors include plasmids such as pBR322-based plasmids, e.g., pBLUESCRIPT™, pSKF, pET23D, lambda-phage derived vectors, and fusion expression systems such as GST and LacZ. Epitope tags can also be added to recombinant proteins to provide convenient methods of isolation, e.g., c-myc, HA-tag, 6-His (SEQ ID NO:39) tag, maltose binding protein, VSV-G tag, anti-DYKDDDDK (SEQ ID NO:40) tag, or any such tag, a large number of which are well known to those of skill in the art.

III. Polymerases

As noted above, it is believed that any polymerase not naturally having 5'-3' exonuclease activity can be used as described herein as a fusion partner with a heterologous 5'-3' exonuclease domain. Exemplary polymerases not naturally having 5'-3' exonuclease activity include family B polymerases. In some embodiments, the family B polymerase is an archeal family B polymerase.

A number of DNA polymerases have been grouped under the designation of DNA polymerase family B. Six regions of similarity (numbered from I to VI) are found in all or a subset of the B family polymerases. The most conserved region (I) includes a conserved tetrapeptide with two aspartate residues. Its function is not yet known. However, it has been suggested that it may be involved in binding a magnesium ion. All naturally-occurring polymerase sequences in the B family contain a characteristic DTDS (SEQ ID NO:41) motif, and possess many functional domains, including a 5'-3' elongation domain, a 3'-5' exonuclease domain, a DNA binding domain, and binding domains for both dNTP's and pyrophosphate (see, e.g., Zhou M, et al., *Acta Crystallographica*. Section D, Biological Crystallography 54 (Pt 5): 994-995 (1998)). Conserved amino acid residues of family B polymerases are described, for example, Hopfner, K.-P., et al., *Proc. Natl. Acad. Sci USA* 96: 36003605 (1999) in general and in FIG. 3 in particular.

Exemplary polymerases useful in the fusions described herein include, but are not limited to, *Pyrococcus horikoshii* (e.g., accession number 059610), *P. abyssi* (e.g., accession number P77916), *P. glycovorans* (e.g., accession number CAC12849), *Pyrococcus* sp. GE23 (e.g., accession number CAA90887), *Pyrococcus* sp. GB-D (e.g., accession number Q51334), *P. furiosus* (e.g., accession number P61875), *P. woesei* (e.g., accession number P61876), *Thermococcus kodakaraensis* (e.g., accession number P77933), *T. gorgonarius* (e.g., accession number P56689), *T. fumicolans* (e.g., accession number P74918), *T.* sp. 9oN-7 (e.g., accession number Q56366), *T. onnurineus* NA1 (e.g., accession number ABC11972), *T. litoralis* (e.g., accession number P30317), and *T. aggregans* (e.g., accession number 033845), as well as fragments and variants (e.g., substantially identical versions thereof) thereof that retain polymerase activity. In some embodiments, the polymerase is derived from two parental polymerases, e.g., Pfu and DeepVent. Such polymerases are described for example in U.S. Application Publication Nos. 20040219558; 20040214194; 20040191825; 20030162173, each of which is hereby incorporated by reference in its entirety for all purposes and in particular for all teachings related to hybrid polymerases.

In some aspects, the fusion polypeptide has 3'-5' exonuclease activity and an active uracil sensing activity, as well as polymerase activity. In other aspects, the polymerase lacks one or more 3'-5' exonuclease activity and an active uracil sensing activity. As described in more detail below, in some aspects, the polymerase lacks or substantially lacks the uracil sensing domain (USD).

In one aspect, the fusion polypeptide lacks 3'-5' exonuclease activity. In one embodiment, such fusion polypeptides comprise a double point mutation in the polymerase domain that provides this exonuclease deficiency. A variety of mutations can be introduced into a native or mutant polymerase domain to reduce or eliminate 3'-5' exonuclease activity. For example, U.S. Pat. Nos. 6,015,668; 5,939,301 and 5,948,614 describe mutations of a metal-binding aspartate to an alanine residue in the 3'-5' exonuclease domain of the Tma and Tne DNA polymerases. These mutations reduce the 3'-5' exonuclease activities of these enzymes to below detectable levels. Similarly, U.S. Pat. No. 5,882,904 describes an analogous aspartate-to-alanine mutation in *Thermococcus barossi*, and U.S. Pat. No. 5,489,523 teaches the double-mutant D141A E143A of the *Pyrococcus wosei* DNA polymerases. Both of these mutant polymerases have virtually no detectable 3'-5' exonuclease activity. Methods of assaying 3'-5' exonuclease activity are well-known in the art. See, e.g., Freemont et al., *Proteins* 1:66 (1986); Derbyshire et al., *EMBO J.* 16:17 (1991) and Derbyshire et al., *Methods in Enzymology* 262: 363 85 (1995). It will be understood that while the above-described mutations were originally identified in one polymerase, one can generally introduce such mutations into other polymerases to reduce or eliminate exonuclease activity. In a specific embodiment, a polymerase comprises the double point mutation corresponding to D141A/E143A in the polymerase domain. Sequence comparisons can be performed using any BLAST including BLAST 2.2 algorithm with default parameters, described in Altschul et al., *Nuc. Acids Res.* 25:3389 3402 (1977) and Altschul et al., *J. Mol. Biol.* 215:403 410 (1990), respectively, to determine the "corresponding" amino acid in a different polymerase.

Figure 3:
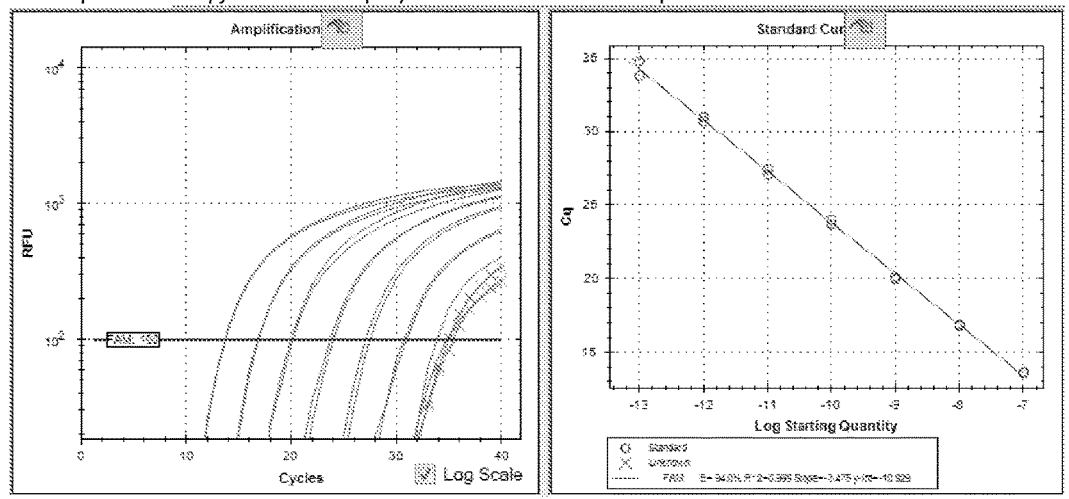
FIG. 3 illustrates results of quantitative detection of probe-based qPCR reactions using Da FEN1 5'-3' exonuclease domain fused to DNA polymerase (upper), and Da FEN1 5'-3' exonuclease domain fused to DNA polymerase lack of uracil-sensing domain (lower).
Figure 3:
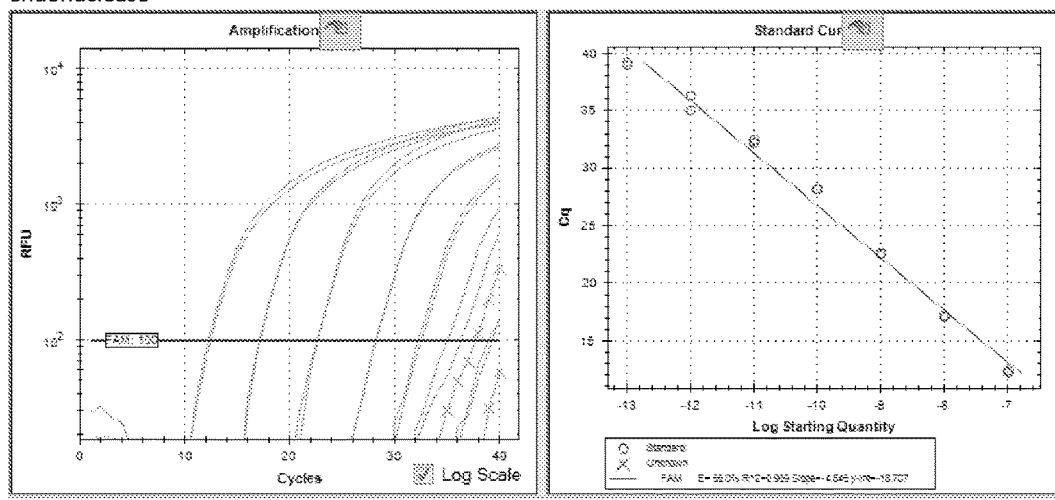

In one aspect, the polymerase in the fusion polypeptide lacks a uracil sensing domain (USD). The USD is generally described in Kim et al., *J. Microbiol. Biotechnol.* 18(8): 1377-1385 (2008), which also describes assays for measuring uracil sensing. FIG. 3 of Kim et al, supra, provides an alignment of various USDs. USDs are also described in, e.g., European Patent Application Publication No. EP1463809B1. As described in the Examples below, it has been surprisingly discovered the entire USD can be removed from a family B polymerase without significantly affecting polymerase activity. Accordingly, in some embodiments, the fusion polypeptides as described herein lack at least a portion (e.g., at least 10, 20, 30, 40, 50, 60, 70, 80, 90, 100, 110, 120, or 125 contiguous amino acids), a majority of, or all of the native USD. The USD of an exemplary Pfu/DeepVent hybrid DNA polymerase (SEQ ID NO: 20) is ILDADYITEEGKPVIRLFKKENGEFKIEHDRTFRPYI-YALLKDDSKIEEVKKITAERHGKIV RIVDAEKVEK-KFLGRPITVWRLYFEHPQDVPTIREKIREHSAV-VDIFEYDIPFAKRY (SEQ ID NO:25) and the USD of Pfu is ILDVDYITEEGKPVIRLFKKENGKFKIEHDRT-FRPYIYALLRDDSKIEEVKKITGERHGKIV RIVDVEK-VEKKFLGKPITVWKLYLEHPQDVPTIREKVREHPAV-VDIFEYDIPFAKRY (SEQ ID NO:38), though it will be appreciated that USDs of other polymerases may vary at least somewhat in sequence from SEQ ID NO:25 (e.g., a USD can be substantially identical to SEQ ID NO:25). As shown in the Examples, the inventors have found that additional amino acids (e.g., corresponding to SEQ ID NO:26) following the USD can also be conveniently removed from the polymerase without significantly affecting polymerase activity. Removal or inactivation of the USD can be useful to enable the fusion polypeptide to amplify templates comprising incorporated uracils, deaminated bases (e.g., inosine), and/or bisulfite-converted bases, for example.

IV. Sequence Non-Specific DNA Binding Domains

In some embodiments, fusion polypeptides described herein comprise a heterologous DNA binding domain. A DNA binding domain is a protein, or a defined region of a protein, that binds to nucleic acid in a sequence-independent matter, e.g., binding does not exhibit a gross preference for a particular sequence. DNA binding domains may bind single or double stranded nucleic acids.

The DNA binding proteins of use are generally thermostable. Examples of such proteins include, but are not limited to, the Archaeal small basic DNA binding proteins Sso7d and Sso7d-like proteins (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998), Archaeal HMf-like proteins (see, e.g., Starich et al., *J. Molec. Biol.* 255:187-203, 1996; Sandman et al., *Gene* 150:207-208, 1994), and PCNA homologs (see, e.g., Cann et al., *J. Bacteriology* 181:6591-6599, 1999; Shamoo and Steitz, *Cell:* 99, 155-166, 1999; De Felice et al., *J. Molec. Biol.* 291, 47-57, 1999; and Zhang et al., *Biochemistry* 34:10703-10712, 1995).

Sso7d and Sso7d-like proteins, Sac7d and Sac7d-like proteins, e.g., Sac7a, Sac7b, Sac7d, and Sac7e are small (about 7,000 kd MW), basic chromosomal proteins from the hyperthermophilic archaebacteria *Sulfolobus solfataricus* and *S. acidocaldarius*, respectively. These proteins are lysine-rich and have high thermal, acid and chemical stability. They bind DNA in a sequence-independent manner and when bound, increase the $T_m$ of DNA by up to 40° C. under some conditions (McAfee, *Biochemistry* 34:10063-10077, 1995; Gao et al., *Nat. Struct. Biol.* 5(9):782-786, 1998). These proteins and their homologs are typically believed to be involved in stabilizing genomic DNA at elevated temperatures. Suitable Sso7d-like DNA binding domains for use in the invention can be modified based on their sequence homology to Sso7d. Typically, DNA binding domains that are identical to or substantially identical to a known DNA binding protein over a comparison window of about 25 amino acids, optionally about 50-100 amino acids, or the length of the entire protein, can be used in the invention. The sequence can be compared and aligned for maximum correspondence over a comparison window, or designated region as measured using one of the described comparison algorithms or by manual alignment and visual inspection. A variety of mutations in the Sso7 binding domain have been described in, e.g., US Patent Application Nos. 2005/0048530; 2007/0141591; and WO 2012/138417.

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a).

Certain helix-hairpin-helix motifs have been shown to bind DNA nonspecifically and enhance the processivity of a DNA polymerase to which it is fused (Pavlov et al., *Proc Natl Acad Sci USA*. 99:13510-5, 2002). Single-stranded DNA binding proteins have also been described.

Additional DNA binding domains suitable for use can be identified by homology with known DNA binding proteins and/or by antibody cross reactivity, or may be found by means of a biochemical assay. DNA binding domains may be synthesized or isolated using the techniques described herein and known in the art.

Sequence non-specific single-stranded or doubled-stranded nucleic acid binding domains for use can also be identified by cross-reactivity using antibodies, including but not limited to, polyclonal antibodies that bind to known nucleic acid binding domains. Polyclonal antibodies are generated using methods well known to those of ordinary skill in the art (see, e.g., Coligan, *Current Protocols in Immunology* (1991); Harlow & Lane, *Antibodies, A Laboratory Manual* (1988)). Those proteins that are immunologically cross-reactive binding proteins can then be detected by a variety of assay methods. For descriptions of various formats and conditions that can be used, see, e.g., Methods in Cell Biology: Antibodies in Cell Biology, volume 37 (Asai, ed. 1993), Coligan, supra, and Harlow & Lane, supra.

Specificity for binding to double-stranded nucleic acids can be tested using a variety of assays known to those of ordinary skill in the art. These include such assays as filter binding assays or gel-shift assays. For example, in a filter-binding assay the polypeptide to be assessed for binding activity to double-stranded DNA is pre-mixed with radio-labeled DNA, either double-stranded or single-stranded, in the appropriate buffer. The mixture is filtered through a membrane (e.g., nitrocellulose) which retains the protein and the protein-DNA complex. The amount of DNA that is retained on the filter is indicative of the quantity that bound to the protein. Binding can be quantified by a competition analysis in which binding of labeled DNA is competed by the addition of increasing amounts of unlabeled DNA. A polypeptide that binds double-stranded DNA at a 10-fold or greater affinity than single-stranded DNA is defined herein as a double-stranded DNA binding protein. Alternatively, binding activity can be assessed by a gel shift assay in which radiolabeled DNA is incubated with the test polypeptide. The protein-DNA complex will migrate slower through the gel than unbound DNA, resulting in a shifted band. The amount of binding is assessed by incubating samples with increasing amounts of double-stranded or single-stranded unlabeled DNA, and quantifying the amount of radioactivity in the shifted band.

A binding domain binds to double-stranded nucleic acids in a sequence-independent fashion, i.e., a binding domain of the invention binds double-stranded nucleic acids with a significant affinity, but, there is no known double-stranded nucleic acid that binds to the domain with more than 100-fold more affinity than another double stranded nucleic acid with the same nucleotide composition, but a different nucleic acid sequence. Non-specific binding can be assayed using methodology similar to that described for determining double-stranded vs. single-stranded nucleic acid binding. Filter binding assays or gel mobility shift assays can be performed as above using competitor DNAs of the same nucleotide composition, but different nucleic acid sequences to determine specificity of binding.

Sequence non-specific single-stranded or double-stranded nucleic acid binding domains can also be assessed, for example, by assaying the ability of the single-stranded or double-stranded binding domain to increase processivity or efficiency of a modifying enzyme or, in the case of double-stranded nucleic acid binding domains, to increase the stability of a nucleic acid duplex by at least 1° C. can be determined.

A binding domain of the invention can also be identified by direct assessment of the ability of such a domain to stabilize a double-stranded nucleic acid conformation. For example, a melting curve of a primer-template construct can be obtained in the presence or absence of protein by monitoring the UV absorbance of the DNA at 260 nm. The $T_m$ of the double-stranded substrate can be determined from the midpoint of the melting curve. The effect of the sequence-non-specific double-stranded nucleic-acid-binding protein on the $T_m$ can then be determined by comparing the $T_m$ obtained in the presence of the modified enzyme with that in the presence of the unmodified enzyme. (The protein does not significantly contribute to the UV absorbance because it has a much lower extinction coefficient at 260 nm than DNA). A domain that increases the $T_m$ by 1° C., often by 5° C., 10° C. or more, can then be selected for use in the invention.

Novel sequence non-specific double-stranded nucleic acid binding proteins of the invention can also be isolated by taking advantage of their DNA binding activity, for instance by purification on DNA-cellulose columns. The isolated proteins can then be further purified by conventional means, sequenced, and the genes cloned by conventional means via PCR. Proteins overexpressed from these clones can then be tested by any of the means described above.

In some embodiments, the fusion polypeptides described herein comprise an Sso7 polypeptide sequence that is substantially identical to SEQ ID NOs: 27, 28, 29, 30, or 31. In some embodiments, the Sso7 polypeptide sequence has amino acid substitutions compared to the native (wildtype) Sso7d sequence. In some embodiments, the amino acid substitutions include amino acid changes from the native amino acid at the positions corresponding to K28 and/or R43 of SEQ ID NO:27. It should be understood that such position designations do not indicate the number of amino acids in the claimed molecule per se, but indicate where in the claimed molecule the residue occurs when the claimed molecule sequence is maximally aligned with SEQ ID NO:27.

Any Sso7 DNA binding protein domain can be substituted at the K28 and/or R43 position corresponding to SEQ ID NO:27. Thus, for example, in some embodiments, the variant Sso7 polypeptide sequence is substantially (e.g., at least 60, 70, 80, 85, 90, or 95%) identical to any of, e.g., SEQ ID NOS:27, 28, 29, 30, or 31, and comprises an amino acid other than K at the amino acid position corresponding to K28. In some embodiments, the amino acid position corresponding to K28 is serine (S), threonine (T), cysteine (C), proline (P), aspartic acid (D), glutamic acid (E), asparagine (N), glutamine (Q), alanine (A), phenylalanine (F), glycine (G), histidine (H), isoleucine (I), leucine (L), methionine (M), arginine (R), valine (V), tryptophan (W), or tyrosine (Y).

In some embodiments, the variant Sso7 polypeptide sequence is substantially (e.g., at least 60, 70, 80, 85, 90, or 95%) identical to any of, e.g., SEQ ID NOS: 27, 28, 29, 30, or 31, and comprises an amino acid other than R at the amino acid position corresponding to R43. In some embodiments, the amino acid position corresponding to R43 is alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y), or proline (P).

In some embodiments, the variant Sso7 polypeptide sequence is substantially (e.g., at least 60, 70, 80, 85, 90, or 95%) identical to any of, e.g., SEQ ID NOS: 27, 28, 29, 30, or 31, and comprises an amino acid other than K at the amino acid position corresponding to K28 and an amino acid other than R at the amino acid position corresponding to R43. For example, in some embodiments, the amino acid at position K28 is selected from: serine (S), threonine (T), cysteine (C), proline (P), aspartic acid (D), glutamic acid (E), asparagine (N), glutamine (Q), alanine (A), phenylalanine (F), glycine (G), histidine (H), isoleucine (I), leucine (L), valine (V), tryptophan (W), or tyrosine (Y) and the amino acid at position R43 is selected from: alanine (A), cytosine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y), or proline (P).

V. Methods

In some embodiments, the fusion polypeptides described herein are used in nucleic acid amplification reactions. Such amplification reactions can include without limitation polymerase chain reaction (PCR), DNA ligase chain reaction (LCR), QBeta RNA replicase, and RNA transcription-based (such as TAS and 3 SR) amplification reactions as well as others known to those of skill in the art. Polymerase chain reactions that can be conducted using the compositions described herein include without limitation reverse-transcription PCR (rt-PCR) and quantitative PCR (qPCR).

In some embodiments, the PCR is quantitative PCR in which the accumulation of amplicon is monitored in "real time" (i.e., continuously, e.g., once per cycle—rather than only following the completion of amplification). Quantitative amplification methods (e.g., quantitative PCR or quantitative linear amplification) can involve amplification of an nucleic acid template, directly or indirectly (e.g., determining a Ct value) determining the amount of amplified DNA, and then calculating the amount of initial template based on the number of cycles of the amplification. Amplification of a DNA locus using reactions is well known (see U.S. Pat. Nos. 4,683,195 and 4,683,202; PCR PROTOCOLS: A GUIDE TO METHODS AND APPLICATIONS (Innis et al., eds, 1990)). Typically, PCR is used to amplify DNA templates. However, alternative methods of amplification have been described and can also be employed, as long as the alternative methods amplify intact DNA to a greater extent than the methods amplify cleaved DNA. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002).

In some embodiments, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. *Genome Methods* 6:986-94 (1996) with reference to hydrolysis probes.

One method for detection of amplification products is the 5'-3' exonuclease "hydrolysis" PCR assay (also sometimes referred to as the TaqMan™ assay) (U.S. Pat. Nos. 5,210,015 and 5,487,972; Holland et al., *PNAS USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (e.g., the "TaqMan™" probe) during the amplification reaction. The fluorogenic probe consists of an oligonucleotide labeled with both a fluorescent reporter dye and a quencher dye. During PCR, this probe is cleaved by the 5'-3' exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in the open conformation and fluorescence is detected, while those that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of a nucleic acids are also known. For example, some methodologies employ one or more probe oligonucleotides that are structured such that a change in fluorescence is generated when the oligonucleotide(s) is hybridized to a target nucleic acid. For example, one such method involves is a dual fluorophore approach that exploits fluorescence resonance energy transfer (FRET), e.g., Light-Cycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145), Sunrise™ (or Amplifluor™) probes (e.g., Nazarenko et al., *Nuc. Acids Res.* 25:2516-2521, 1997, and U.S. Pat. No. 6,117,635), and probes that form a secondary structure that results in reduced signal without a quencher and that emits increased signal when hybridized to a target (e.g., Lux Probes™).

In some embodiments, the PCR reaction mixture does not include a labeled probe oligonucleotide. For example, the reaction mixture lacks a Taqman or other labeled oligonucleotide probe for monitoring real-time or endpoint accumulation of the amplicon. In some of these embodiments, an intercalating fluorescent dye is included. In some embodiments, the intercalating dye changes signal (increases or decreases) when bound to double stranded nucleic acids compared to single stranded nucleic acids. Exemplary agents include SYBR GREEN™, SYBR GOLD™, and EVAGREEN™. Since these agents are not template-specific, it is assumed that the signal is generated based on template-specific amplification. This can be confirmed by monitoring signal as a function of temperature because melting point of template sequences will generally be much higher than or different from, for example, primer-dimers, non-specifically amplified sequences, etc.

A number of components of a PCR reaction are well known and can be determined readily by a skilled artisan. In certain aspects, it may be desirable to include an additional compound as an additive to improve efficiency in amplification reactions, such as qPCR. For example, there may be situations in which a polymerase of the invention that lacks exonuclease activity exhibits low efficiency for certain targets when used in a formulation that includes certain binding dyes (such as, in one non-limiting example, an EvaGreen DNA binding dye) or in the presence of certain amplification inhibitors. Such low efficiency may in some embodiments be a result of delay in Ct values associated with low input DNA concentrations. Methods for measuring efficiency of a particular reaction are known in the art.

In some embodiments, an osmolyte may be included in an amplification reaction of the invention to improve efficiency. See, e.g., WO2010/080910, incorporated by reference. Members of the osmolyte family have been shown to improve the thermal stability of proteins (Santoro, *Biochemistry*, 1992) as well as decrease DNA double helix stability (Chadalavada, *FEBS Letters,* 1997). Osmolytes of use in the present invention may include without limitation sarcosine, trimethylamine N-oxide (TMAO), dimethyl sulfoniopropionate, and trimethylglycine. Sarcosine is chemically similar to betaine, a chemical which has been shown to improve conventional PCR (Henke, Nucleic Acids Research, 1997).

In conventional uses of osmolytes, the stabilizing effects of such compounds are generally observed at relatively high concentrations (>1M). However, in methods of the present invention, millimolar concentrations of osmolytes have been found to be effective for improving the reaction efficiency of amplification reactions such as qPCR. See, e.g., WO2010/080910, incorporated by reference. Without being bound by a mechanism of action, it is possible that the improvement in efficiency is the result of improvement of the Ct values for the reactions that contain low DNA template concentration. In some embodiments, concentrations of about 100 to about 1000 mM of osmolytes are used in methods and kits of the present invention. In still further embodiments, concentrations of about 50 to about 700, about 100 to about 600, about 150 to about 500, about 200 to about 400 mM, or about 300 to about 350 mM osmolytes are used in methods and kits of the invention. In some embodiments, the osmolyte used in methods and kits of the invention is sarcosine. Indeed, it has been found that addition of sarcosine improved the efficiency of the amplification reaction as compared to control comprising water.

In some embodiments, particularly in the amplification of low-copy target nucleic acids or in the presence of amplification inhibitors, efficiency decreases due to the binding of polymerase to non-primed double-stranded nucleic acid targets. Binding of the polymerase to the double-stranded targets will prevent those targets from denaturation, hybridizing to primers, and undergoing an amplification reaction. To improve the specificity of the polymerase for primed templates, in some embodiments methods and kits of the invention utilize heparin. See, e.g., WO2010/080910, incorporated by reference. Heparin molecules, which are negatively charged, can be included in the reaction mixture to mimic the electrostatic property of double stranded nucleic acids. The addition of heparin can, without being limited to a mechanism of action, prevent excess polymerase from binding to the double-stranded template until a single-stranded primed-template becomes available. In some exemplary embodiments, heparin is used in methods and kits of the invention at concentrations of about 50 to about 750 pg/µl. In further exemplary embodiments, heparin is used in methods and kits of the invention at concentrations of about 75 to about 700, about 100 to about 600, about 125 to about 500, about 150 to about 400, about 175 to about 300, or about 200 to about 250 µg/µl.

Non-specific amplification can be reduced by reducing the formation of extension products from primers bound to non-target sequences prior to the start of the reaction. In one method, referred to as a "hot-start" protocol, one or more critical reagents are withheld from the reaction mixture until the temperature is raised sufficiently to provide the necessary hybridization specificity. In this manner, the reaction mixture cannot support primer extension during the time that the reaction conditions do not insure specific primer hybridization. In some embodiments, the polypeptides as described herein can be reversibly inactivated by a reagent bound to the polymerase. The inhibitory reagent can be removed by heat (e.g., above 50 or at 95° C.). Thus, in some embodiments, the amplification reaction comprises a hot start reagent.

In some embodiments, the reagent is a "hot start" antibody. Hot-start antibodies increase the specificity of amplification reactions, because they render the polymerase inactive at room temperature, thus avoiding extension of nonspecifically annealed primers or primer dimers. See, e.g., U.S. Pat. No. 5,338,671. The functional activity of the polymerase is restored by disassociating the antibody from the polymerase, generally through incubation at a higher temperature. In some embodiment, such a "higher temperature" is from about 90° to about 99° C. for about 2 to about 10 minutes. It will be appreciated that the temperature and length of time for incubation to disassociate the antibody and activate the polymerase can be varied according to known parameters to provide the most effective method of activating the polymerase in these hot-start methods. In other embodiments, the reagent is an aptamer that inhibits polymerase activity until the polymerase is heated to disassociate the aptamer. Exemplary aptamers include, but are not limited to, slow off-rate modified aptamers (e.g., SOMAmers™).

Alternatively, a polymerase can be substantially inactivated by covalently linking a chemical reagent to the polymerase. For example a dicarboxylic acid anhydride can be linked to one or more lysine residue of the polymerase, thereby substantially inactivating the polymerase activity. See, e.g., U.S. Pat. Nos. 5,773,258 and 5,677,152. The reagents are thermally labile and thus can be removed upon heating.

In some embodiments, the fusion polypeptide comprising a FEN1 protein or active fragment thereof can be used to generate a 5' cleaved primer flap that subsequently is used to prime a second amplification reaction to generate a detectable signal. An example of such a method includes the TOCE™ assay (Seegene, KR). Such assays detect a target nucleic acid sequence in which the PTO (Probing and Tagging Oligonucleotide) hybridized with the target nucleic acid sequence is cleaved to release a fragment and the fragment is hybridized with the CTO (Capturing and Templating Oligonucleotide) to form an extended duplex, followed by detecting the presence of the extended duplex. The extended duplex provides signals (generation, increase, extinguishment or decrease of signals) from labels indicating the presence of the extended duplex and has adjustable Tm value, which are well adoptable for detection of the presence of the target nucleic acid sequence. See, e.g., US Patent Publication No. 2013/0109588.

In other embodiments, the fusion polypeptide can be used to cause recombination between DNA strands, thereby replacing one strand of a DNA duplex with a homologous third strand. For example, the fusion polypeptide comprising 5'-3' exonuclease activity can be used to facilitate "somatic recombination" type of cross-linking

VI. Reaction Mixtures

The present invention also provides for reaction mixtures comprising one or more of the fusion polypeptides as described herein. Other reagents as described herein can also be included in the reaction mixture. For example, in some embodiments, the reaction mixtures comprise a fluorogenic probe comprises an oligonucleotide labeled with both a fluorescent reporter dye and a quencher dye that generates signal in a 5'-3' exonuclease "hydrolysis" PCR assay (also referred to as a TaqMan™ assay) (U.S. Pat. Nos. 5,210,015 and 5,487,972; Holland et al., *PNAS USA* 88: 7276-7280 (1991); Lee et al., *Nucleic Acids Res.* 21: 3761-3766 (1993)).

In some embodiments, the fusion polypeptides described herein have increased tolerance for common PCR inhibitors, e.g., inhibitors of Taq polymerase. Exemplary PCR inhibitors include, but are not limited to, heparin, bile salts, polysaccharides, collagen, heme, humic acid, melanin and eumelanin, urea, hemoglobin, lactoferrin, immunoglobulin G (IgG), and indigo dye. Thus in some embodiments the reaction mixture comprises a sample having inhibitors that would significantly inhibit activity of Taq polymerase (e.g., degrading Ct values by at least 1 compared to the Ct of a polymerase as described herein).

In some embodiments, the sample is a crude sample, i.e., a sample in which minimal or no purification of nucleic acids has occurred. For example, the crude sample can be a blood or serum sample, cell lysate, a plant or animal tissue sample, etc.

In some embodiments, the amplification reaction comprises dUTP and/or a nucleic acid template comprising incorporated uracil. In some embodiments, dUTP is included in an amplification reaction mixture so that amplification products can be prevented from contaminating future amplification reactions. This is achieved by an additional incubation step in the presence of the enzyme, UNG, followed by inactivation of UNG, prior to the amplification reactions. UNG renders uracil-containing templates unable to be amplified by polymerases.

In some embodiments, the target template to be amplified contains incorporated uracil. Polymerases having an active uracil-sensing domain (e.g., most or all native B family polymerases) typically stall at an incorporated uracil in the template. In contrast, polypeptides lacking an active USD as described herein will not stall at incorporated uracils.

In some embodiments, the reaction mixture is formulated as a ready-to-use formulation, meaning the mixture contains all components needed for a polymerase reaction except for a sample or except for a sample and oligonucleotide primers.

In some embodiments, the reaction mixture further comprises a reverse transcriptase and optionally reagents necessary for reverse transcription. Thus in some embodiments, the reaction mixture can be used to generate a cDNA from RNA in a sample and then the fusion polypeptide can subsequently amplify the cDNA in the same reaction mixture. Alternatively, the cDNA can be generated in a previous reverse transcription reaction and the resulting cDNA can be added to a reaction mixture in a two-step reaction (a first step for the RT reaction, and a second for the cDNA amplification).

VII. Polynucleotides

Also provided are polynucleotides encoding (1) a fusion polypeptide comprising a heterologous 5'-3' exonuclease domain and a polymerase (e.g., family B polymerase) as described herein or (2) a family B polymerase lacking the uracil sensing domain (USD). In some embodiments, the polynucleotides are isolated, i.e., are separated from the cell in which the polypeptide was translated and optionally purified. In some embodiments, expression cassettes (i.e., a heterologous promoter operably linked to the coding sequence) or vectors comprising the above-described polynucleotide are provided, as well as host cells (including but not limited to bacterial, fungal, yeast, insect, or mammalian cells) comprising such expression cassettes or vectors. Such host cells can be incubated under conditions to result in expression of the encoded polypeptide, which can subsequently be purified as desired.

VIII. Kits

In one aspect, kits comprising a fusion polypeptide as described herein is provided. Kits can be adapted, for example, for conducting nucleic acid amplification reactions. In some embodiments, such kits include dNTPs, and at least one buffer. Such kits may also include one or more primers as well as instructions for conducting nucleic acid amplification reactions using the components of the kits.

In still further embodiments, kits can include optimized buffer (e.g., Tris-HCl), KCl, $(NH_4)_2SO_4$, stabilizer, detergent, dNTPs, $MgCl_2$, and/or DMSO.

In still further embodiments, kits can include double stranded DNA binding dyes. Such double stranded DNA binding dyes can include without limitation: EvaGreen and SYBR Green, as well as any other double stranded DNA binding dyes known in the art.

Alternatively, or in addition, the kit can comprise one of more nucleic acid probe for use in a 5'-3' exonuclease "hydrolysis" PCR assay (also referred to as a TaqMan™ assay) (U.S. Pat. Nos. 5,210,015 and 5,487,972; Holland et al., *PNAS USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the "TaqMan™ probe") during the amplification reaction. The fluorogenic probe comprises an oligonucleotide labeled with both a fluorescent reporter dye and a quencher dye. During PCR, this probe is cleaved by the 5'-3' exonuclease activity of DNA polymerase if, and only if, it hybridizes to the segment being amplified. Cleavage of the probe generates an increase in the fluorescence intensity of the reporter dye.

It will be appreciated that kits can also encompass any combination of the above-described components.

The following examples are offered to illustrate, but not to limit the claimed invention.

EXAMPLES

Example 1

Proof-reading DNA polymerases, such as pfu DNA polymerase, oftentimes are hyper-thermalphilic (or highly thermal stable) and have ability to perform well in the presence of common DNA polymerase inhibitors, such as salt and solvent. These proof-reading DNA polymerases usually have a 3'-5' exonuclease activity that enhances fidelity; however they lack of 5'-3' exonuclease activity that is essential for signal generation in probe-based qPCR applications.

We constructed fusion DNA polymerases comprising a proof-reading DNA polymerase fused to two different flap endonucleases (Archaeon *Pyrococcus furiosus* flap endonuclease (pfu FEN1 SEQ ID NO:24)) and Archaeon *Desulfurococcus amylolyticus* flap endonuclease (Da FEN1 SEQ ID NO:10)). A flexible linker (SEQ ID NO:8) was used to link the carboxyl terminus of the flap endonuclease domain to the amino terminus of the polymerase. The polymerase used was a Pfu/Vent-hybrid DNA polymerase (SEQ ID NO: 20) and further included a carboxyl terminal Sso7d domain with a K28 mutation (SEQ ID NO: 22) and then a poly-His tag. The full length amino acid and coding sequence of the pfu FEN1-polymerase-Sso7d fusion (referred to as "fusion protein #1") as tested is SEQ ID NO:1 and 5, respectively. The full length amino acid and coding sequence of the Da FEN1-polymerase-Sso7d fusion (referred to as "fusion protein #2") as tested is SEQ ID NO:2 and 6, respectively.

We also constructed similar fusions, however without the uracil sensing domain (USD) of polymerase. In fact, in addition to the removal of the entire USD, a small number of additional amino acids were removed from the polymerase based on the predicted structure of the polymerase. The full length amino acid and coding sequence of the pfu FEN1-polymerase (USD minus)-Sso7d fusion (referred to as "fusion protein #3") as tested is SEQ ID NO:3 and 7, respectively. The full length amino acid and coding sequence of the Da FEN1-polymerase (USD minus)-Sso7d fusion (referred to as "fusion protein #4") as tested is SEQ ID NO:4 and 8, respectively.

The fusions were tested in a probe qPCR assay that required 5'-3' exonuclease activity to generate signal. As shown in the top part of FIG. 1, the positive control (Taq polymerase) generated signal in a concentration dependent manner. In contrast, the negative control (a pfu/DeepVent hybrid polymerase lacking 5'-3' exonuclease activity) did not generate significant signal. However, each of the above-described fusion proteins (fusions #1-4) had activity at least comparable to Taq.

Example 2

Taq polymerase has 5'-3' exonuclease activity but is generally considered to have a relatively low tolerance for the presence of inhibitors in the reaction mixture. In contrast, pfu and other family B polymerases lack 5'-3' exonuclease activity, but have a higher inhibitor tolerance. We tested one of the fusions described herein (Pfu FEN1 fused to a Pfu/DeepVent hybrid DNA polymerase (SEQ ID NO:20) and an Sso7d domain) to determine whether the protein fusions retain the higher inhibitor tolerance of the B family polymerases with the fusion of the 5'-3' exonuclease domain. iSTaq DNA polymerase (a fusion Sso7d DNA-binding protein and Taq DNA polymerase) was used as a control polymerase in these experiments. The effect of the following inhibitors was tested: heparin with ammonium and sodium salt, hematin, and humic acid. Inhibitor tolerance is reported in term of Cq value.

| Heparin Ammonium Salt | | |
|---|---|---|
| ng per 20 ul reaction | iSTaq Pol (Control) Cq value | fusion protein #1 (Test) Cq value |
| 0 | 16.3 | 16.0 |
| 0.4 | 16.3 | 16.1 |
| 1.6 | 17.1 | 16.1 |
| 6.3 | n.d. | 16.0 |
| 25 | n.d. | 18.5 |

| Heparin Sodium Salt | | |
|---|---|---|
| ng per 20 ul reaction | iSTaq Pol (Control) Cq value | fusion protein #1 (Test) Cq value |
| 0 | 16.2 | 16.3 |
| 0.4 | 16.0 | 16.2 |
| 1.6 | 17.3 | 15.9 |
| 6.3 | n.d. | 15.8 |
| 25 | n.d. | 21.7 |

| Hematin | | |
|---|---|---|
| nM | iSTaq Pol (Control) Cq value | fusion protein #1 (Test) Cq value |
| 0 | 16.2 | 16.1 |
| 150 | 15.8 | 15.8 |
| 187.5 | 16.8 | 15.7 |
| 225 | 29.6 | 16.0 |
| 262.5 | 38.2 | 16.1 |
| 300 | n.d. | 29.4 |

| Humic Acid | | |
|---|---|---|
| ng per 20 ul reaction | iSTaq Pol (Control) Cq value | fusion protein #1 (Test) Cq value |
| 0 | 16.0 | 16.2 |
| 0.8 | 16.0 | 16.1 |
| 3.1 | 18.7 | 16.0 |
| 12.5 | n.d. | 27.2 |
| 50 | n.d. | n.d. |

As shown in the data above, the 5'-3' exonuclease—Pfu/DeepVent hybrid DNA polymerase—Sso7d fusion had a higher tolerance for a variety of inhibitors compared to the Taq polymerase-based Sso7d fusion, demonstrating that the fusions described herein retain the higher inhibitor tolerance of the family B polymerases even when fused to the 5'-3' exonuclease domain.

Example 3

A fusion DNA polymerases comprising a proof-reading DNA polymerase (SEQ ID NO: 20) was fused to 5'-3' exonuclease domain of Taq polymerase 5'-3' exonuclease domain (SEQ ID NO:35). The resulting DNA and amino acid sequence of the fusion was SEQ ID NO: 32 and 33, respectively. A flexible linker (SEQ ID NO:37) was used to link the carboxyl terminus of the 5'-3' exonuclease domain to the amino terminus of the polymerase. The fusion was further fused with a carboxyl terminal Sso7d domain with a K28 mutation (SEQ ID NO: 22) and then a poly-His tag.

Figure 4:
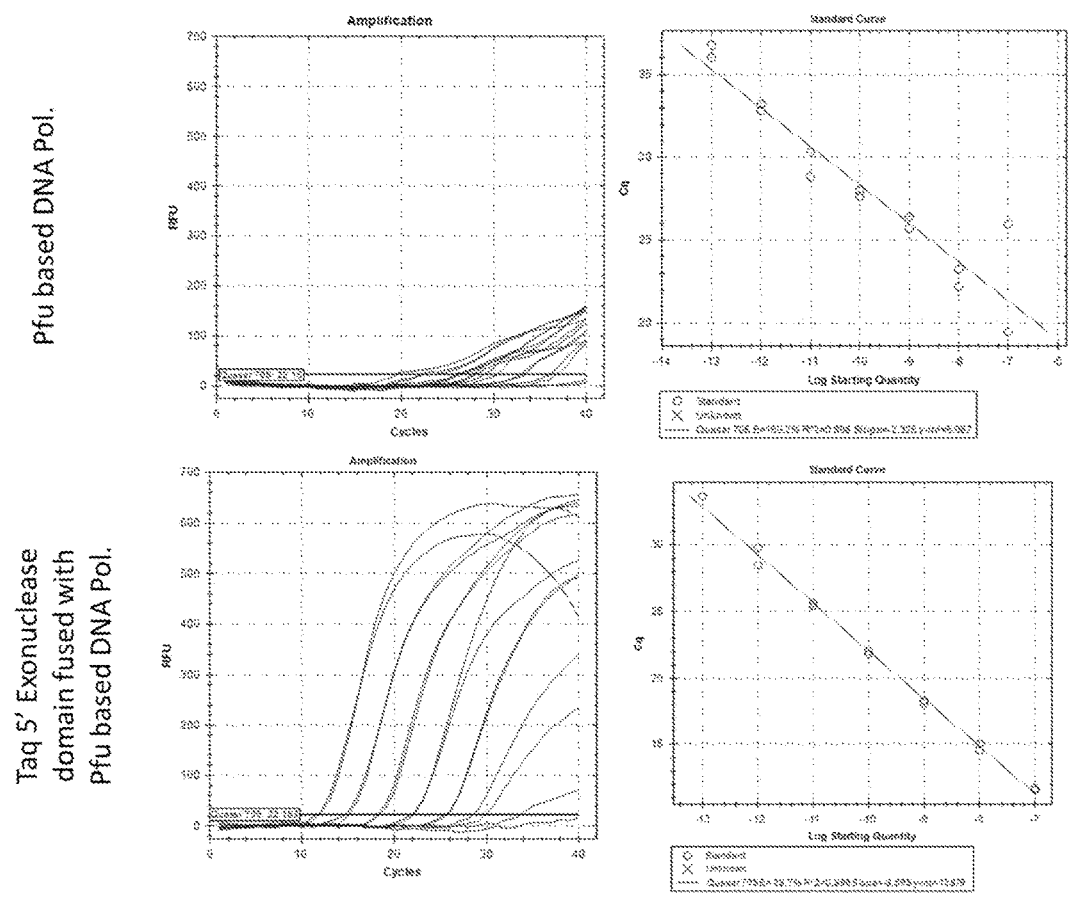
FIG. 4 illustrates results of quantitative detection of probe-based qPCR reactions using a PFU/DEEPVENT polymerase alone (upper) or a Taq 5'-3' exonuclease domain fused to the PFU/DEEPVENT polymerase (lower) as explained in Example 3.

FIG. 4 (lower portion) demonstrates that, in a probe-based qPCR assay, a fusion polymerase with the Taq polymerase 5'-3' exonuclease domain can amplify DNA targets and generate detection signal through probe hydrolysis. In contrast, a polymerase lack of Taq polymerase 5'-3' exonuclease domain cannot generate detectable signal (FIG. 4).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

SEQ ID NO: 1
>Fusion protein #1
MGVPIGEIIPRKEIELENLYGKKIAIDALNAIYQFLSTIRQKDGTPLMDSKGRITSHLSGLFYRTINLMEAGIKPVY
VFDGEPPEFKKKELEKRREAREEAEEKWREALEKGEIEEARKYAQRATRVNEMLIEDAKKLLELMGIPIVQAPSEGE
AQAAYMAAKGSVYASASQDYDSLLFGAPRLVRNLTITGKRKLPGKNVYVEIKPELIILEEVLKELKLTREKLIELAI
LVGTDYNPGGIKGIGLKKALEIVRHSKDPLAKFQKQSDVDLYAIKEFFLNPPVTDNYNLVWRDPDEEGILKFLCDEH
DESEERVKNGLERLKKAIKSGGGSGGGGSGGGGSILDADYITEEGKPVIRLFKKENGEFKIEHDRTFRPYIYALLKD
DSKIEEVKKITAERHGKIVRIVDAEKVEKKFLGRPITVWRLYFEHPQDVPTIREKIREHSAVVDIFEYDIPFAKRYL
IDKGLIPMEGDEELKLLAFAIATLYHEGEEFGKGPIIMISYADEEEAKVITWKKIDLPYVEVVSSEREMIKRFLKII
REKDPDIIITYNGDSFDLPYLAKRAEKLGIKLTIGRDGSEPKMQRIGDMTAVEVKGRIHFDLYHVIRRTINLPTYTL
EAVYEAIFGKPKEKVYADEIAKAWETGEGLERVAKYSMEDAKATYELGKEFFPMEAQLSRLVGQPLWDVSRSSTGNL
VEWELLRKAYERNELAPNKPDEREYERRLRESYAGGFVKEPEKGLWENIVSLDFRALYPSIIITHNVSPDTLNREGC
RNYDVAPEVGHKFCKDFPGFIPSLLKRLLDERQKIKTKMKASQDPIEKIMLDYRQRAIKILANSYYGYYGYAKARWY
CKECAESVTAWGREYIEFVWKELEEKFGEKVLYIDTDGLYATIPGGKSEEIKKKALEFVDYINAKLPGLLELEYEGF
YKRGFEVIKKKYALIDEEGKIITRGLEIVRRDWSEIAKETQARVLEAILKHGNVEEAVRIVKEVTQKLSKYEIPPEK
LAIYEQITRPLHEYKAIGPHVAVAKRLAAKGVKIKPGMVIGYIVLRGDGPISNRAILAEEYDPRKHKYDAEYYIENQ
VLPAVLRILEGFGYRKEDLRWQKTKQTGLTSWLNIKKSGTGGGGATVKFKFKYKGEEKEVDISKIKKVWRVGPMISFTY
DEGGGKTGRGAVSEKDAPKELLQMLEKQKAAALEHHHHHH SEQ ID NO: 2
>Fusion protein #2
MGVPIGEIIPRKEIELENLYGKKIAIDALNAIYQFLSTIRQKDGTPLMDSKGRITSHLSGLFYRTINLMEAGIKPVY
VFDGEPPEFKKKELEKRREAREEAEEKWREALEKGEIEEARKYAQRATRVNEMLIEDAKKLLELMGIPIVQAPSEGE
AQAAYMAAKGSVYASASQDYDSLLFGAPRLVRNLTITGKRKLPGKNVYVEIKPELIILEEVLKELKLTREKLIELAI
LVGTDYNPGGIKGIGLKKALEIVRHSKDPLAKFQKQSDVDLYAIKEFFLNPPVTDNYNLVWRDPDEEGILKFLCDEH
DESEERVKNGLERLKKAIKSGGGSGGGGSGGGGSIPMEGDEELKLLAFAIATLYHEGEEFGKGPIIMISYADEEEAK
VITWKKIDLPYVEVVSSEREMIKRFLKIIREKDPDIIITYNGDSFDLPYLAKRAEKLGIKLTIGRDGSEPKMQRIGD
MTAVEVKGRIHFDLYHVIRRTINLPTYTLEAVYEAIFGKPKEKVYADEIAKAWETGEGLERVAKYSMEDAKATYELG
KEFFPMEAQLSRLVGQPLWDVSRSSTGNLVEWFLLRKAYERNELAPNKPDEREYERRLRESYAGGFVKEPEKGLWEN
IVSLDFRALYPSIIITHNVSPDTLNREGCRNYDVAPEVGHKECKDFPGFIPSLLKRLLDERQKIKTKMKASQDPIEK
IMLDYRQRAIKILANSYYGYYGYAKARWYCKECAESVTAWGREYIEFVWKELEEKFGEKVLYIDTDGLYATIPGGKS
EEIKKKALEFVDYINAKLPGLLELEYEGFYKRGFEVIKKKYALIDEEGKIITRGLEIVRRDWSEIAKETQARVLEAI
LKHGNVEEAVRIVKEVTQKLSKYEIPPEKLAIYEQITRPLHEYKAIGPHVAVAKRLAAKGVKIKPGMVIGYIVLRGD
GPISNRAILAEEYDPRKHKYDAEYYIENQVLPAVLRILEGFGYRKEDLRWQKTKQTGLTSWLNIKKSGTGGGGATVK
FKYKGEEKEVDISKIKKVWRVGPMISFTYDEGGGKTGRGAVSEKDAPKELLQMLEKQKAAALEHHHHHH SEQ ID NO: 3
>Fusion protein #3
MGVDLKDIIPGEAKTVIEDLRILHGKIIVIDGYNALYQFLAAIRQPDGTPLMDNNGRITSHLSGLFYRTINIVEAGI
KPVYVFDGKPPELKAREIERRKAVKEEAAKKYEEAVQSGDLELARRYAMMSAKLTEEMVRDAKSLLDAMGIPWVQAP
AEGEAQAAYIVKKGDAYASASQDYDSLLFGSPKLVRNLTISGRRKLPRKNEYVEVKPELIELDKLLVQLGITLENLI
DIGILLGTDYNPDGFEGIGPKKALQLVKAYGGIEKIPKPILKSPIEVDVIAIKKYFLQPQVIDNYRIEWHTPDPDAV
KRILVDEHDFSIDRVSTALERYVKAFKENIRGEQKGLSKWFSKPKSGGGSGGGGSGGGGSILDADYITEEGKPVIRL
FKKENGEFKIEHDRTFRPYIYALLKDDSKIEEVKKITAERHGKIVRIVDAEKVEKKFLGRPITVWRLYFEHPQDVPT
IREKIREHSAVVDIFEYDIPFAKRYLIDKGLIPMEGDEELKLLAFAIATLYHEGEEFGKGPIIMISYADEEEAKVIT
WKKIDLPYVEVVSSEREMIKRFLKIIREKDPDIIITYNGDSFDLPYLAKRAEKLGIKLTIGRDGSEPKMQRIGDMTA
VEVKGRIHFDLYHVIRRTINLPTYTLEAVYEAIFGKPKEKVYADEIAKAWETGEGLERVAKYSMEDAKATYELGKEF
FPMEAQLSRLVGQPLWDVSRSSIGNLVEWELLRKAYERNELAPNKPDEREYERRLRESYAGGFVKEPEKGLWENIVS
LDFRALYPSIIITHNVSPDTLNREGCRNYDVAPEVGHKECKDFPGFIPSLLKRLLDERQKIKTKMKASQDPIEKIML
DYRQRAIKILANSYYGYYGYAKARWYCKECAESVTAWGREYIEFVWKELEEKFGEKVLYIDTDGLYATIPGGKSEEI

SEQUENCE LISTING

KKKALEFVDYINAKLPGLLELEYEGFYKRGFEVIKKKYALIDEEGKIITRGLEIVRRDWSEIAKETQARVLEAILKH
GNVEEAVRIVKEVTQKLSKYEIPPEKLAIYEQITRPLHEYKAIGPHVAVAKRLAAKGVKIKPGMVIGYIVLRGDGPI
SNRAILAEEYDPRKHKYDAEYYIENQVLPAVLRILEGFGYRKEDLRWQKTKQTGLTSWLNIKKSGTGGGGATVKFKY
KGEEKEVDISKIKKVWRVGPMISFTYDEGGGKTGRGAVSEKDAPKELLQMLEKQKAAALEHHHHHH

SEQ ID NO: 4
>Fusion protein #4
MGVDLKDIIPGEAKTVIEDLRILHGKIIVIDGYNALYQFLAAIRQPDGTPLMDNNGRITSHLSGLFYRTINIVEAGI
KPVYVFDGKPPELKAREIERRKAVKEEAAKKYEEAVQSGDLELARRYAMMSAKLTEEMVRDAKSLLDAMGIPWVQAP
AEGEAQAAYIVKKGDAYASASQDYDSLLFGSPKLVRNLTISGRRKLPRKNEYVEVKPELIELDKLLVQLGITLENLI
DIGILLGTDYNPDGFEGIGPKKALQLVKAYGGIEKIPKPILKSPIEVDVIAIKKYFLQPQVTDNYRIEWHTPDPDAV
KRILVDEHDFSIDRVSTALERYVKAFKENIRGEQKGLSKWFSKPKSGGGSGGGGSGGGGSIPMEGDEELKLLAFAIA
TLYHEGEEFGKGPIIMISYADEEEAKVITWKKIDLPYVEVVSSEREMIKRFLKIIREKDPDIIITYNGDSFDLPYLA
KRAEKLGIKLTIGRDGSEPKMQRIGDMTAVEVKGRIHFDLYHVIRRTINLPTYTLEAVYEAIFGKPKEKVYADEIAK
AWETGEGLERVAKYSMEDAKATYELGKEFFPMEAQLSRLVGQPLWDVSRSSTGNLVEWFLLRKAYERNELAPNKPDE
REYERRLRESYAGGFVKEPEKGLWENIVSLDFRALYPSIIITHNVSPDTLNREGCRNYDVAPEVGHKFCKDFPGFIP
SLLKRLLDERQKIKTKMKASQDPIEKIMLDYRQRAIKILANSYYGYYGYAKARWYCKECAESVTAWGREYIEFVWKE
LEEKFGFKVLYIDTDGLYATIPGGKSEEIKKKALEFVDYINAKLPGLLELEYEGFYKRGFFVTKKKYALIDEEGKII
TRGLEIVRRDWSEIAKETQARVLEAILKHGNVEEAVRIVKEVTQKLSKYEIPPEKLAIYEQITRPLHEYKAIGPHVA
VAKRLAAKGVKIKPGMVIGYIVLRGDGPISNRAILAEEYDPRKHKYDAEYYIENQVLPAVLRILEGFGYRKEDLRWQ
KTKQTGLTSWLNIKKSGTGGGGATVKFKYKGEEKEVDISKIKKVWRVGPMISFTYDEGGGKTGRGAVSEKDAPKELL
QMLEKQKAAALEHHHHHH SEQ ID NO: 5
Codon-optimized (for bacterial expression system) nucleotide sequence of
fusion protein #1
ATGGGCGTGCCGATCGGTGAAATCATCCCACGTAAAGAAATCGAGCTGGAGAACCTGTACGGTAAAAAAATTGCTAT
CGACGCTCTCAACGCCATTTACCAGTTCCTGTCAACTATCCGTCAGAAAGACGGCACTCCGCTCATGGATAGCAAGG
GTCGTATTACCTCTCACCTGTCCGGCCTGTTCTACCGTACGATCAATCTGATGGAAGCAGGGATTAAACCGGTCTAT
GTGTTCGATGGCGAACCGCCAGAgTTCAAAAAgAAaGAGTTGGAAAAACGCCGTGAAGCACGTGAAGAAGCGGAAGA
AAAATGGCGTGAAGCTCTGGAAAAAGGCGAAATCGAAGAAGCGCGTAAATACGCCCAGCGTGCGACCCGTGTCAATG
AAATGCTGATCGAAGACGCCAAAAAACTGCTGGAATTGATGGGTATCCCTATCGTGCAGGCTCCATCTGAAGGCGAA
GCTCAAGCGGCGTATATGGCCGCAAAAGGCTCTGTTTATGCGCTGCTTCCCAAGATTACGACTCCCTGCTGTTTGG
TGCACCGCGCCTGGTCGTAACCTGACCATCACGGGTAAGCGTAAGTTGCCGGGTAAGAACGTTTATGTGGAAATTA
AACCTGAACTGATTATTCTGGAAGAGGTCCTGAAAGAGCTGAAACTGACACGCGAAAAACTGATTGAACTGGCTATC
CTGGTTGGCACAGACTACAACCCAGGCGGTATCAAAGGCATCGGTCTGAAAAAAGCGCTTGAAATCGTGCGTCAcAG
TAAAGATCCGCTGGCTAAGTTTCAGAAACAGAGCGACTGGAACCTGTATGCAATTAAAGAGTTCTTCCTGAACCCTC
CGGTTACTGATAACTACAACCTGGTTTGGCGCGATCCAGACGAGGAGGGTATCCTGAAATTTCTGTGTGATGAACAc
GATTTCTCCGAGGAACGTGTTAAAAACGGTCTGGAGCGTCTGAAGAAGGCGATCAAAtctGGCGGTGGTAGCGGTGG
CGGCGGTTCTGGCGGTGGTGGCAGCATCCTGGATGCTGACTACATCACTGAAGAAGGCAAACCGGTTATCCGTCTGT
TCAAAAAAGAGAACGGCGAATTTAAGATTGAGCATGATCGCATCCTTTCGTCATACATTTACGCTCTGCTGAAAGAT
GATTCTAAGATTGAGGAAGTTAAAAAAATCACTGCTGAGCGCCATGCAAGATTGTTCGTATCGTTGATGCGGAAAA
GGTAGAAAAGAAATTTCTGGGCAGACCAATCACCGTGTGGAGACTGTATTTGAACATCCACAAGATGTTCCGACTA
TTCGCGAGAAATTCGCGAACATTCTGCAGTTGTTGACATCTTGAATACGATATTCCATTTGCAAAGCGTTACCTC
ATCGACAAAGGCCTGATACCAATGGAGGGCGATGAAGAACTCAAGCTCCTGGCGTTCACGATTAGCAACCCTCTATCA
CGAAGGCGAAGAGTTTGGTAAAGGCCCAATTATAATGATCAGCTATGCAGATGAAGAAGAAGCAAAGGTGATTACTT
GGAAAAAAATAGATCTCCCATACGTTGAGGTTGTATCTTCCGAGCGCGAGATGATTAAGCGCTTTCTCAAAATTATC
CGCGAGAAGGATCCGGACATTATCATTACTTATAACGGCGACTCTTTTGACCTCCCATATCTGGCGAAACGCGCAGA
AAAACTCGGTATTAAACTGACTATCGGCCGTGATGGTTCCGAGCCGAAGATGCAGCGTATCGGCGATATGACCGCTG
TAGAAGTTAAGGGTCGTATCCATTTCGACCTGTATCATGTAATTCGTCGTACTATTAACCTCCCGACTTACACTCTC
GAGGCTGTATATGAAGCAATTTTTGGTAAGCCGAAGGAGAAGGTATACGCCGATGAGATTGCAAAGGCGTGGGAAAC
CGGTGAGGGCCTCGAGCGTGTTGCAAAATACTCCATGGAAGATGCAAAGGCGACTTATGAACTCGGCAAAGAATTCT
TCCCAATGGAAGCTCAGCTCTCTCGCCTGGTTGGCCAACCACTGTGGGATGTTTCTCGTTCTTCCACCGGTAACCTC
GTAGAGTGGTTTCTCCTGCGCAAAGCGTACGAACGCAACGAACTGGCTCCGAACAAGCCAGATGAACGTGAGTATGA
ACGCCGTCTCCGCGAGTCTTACGCTGGTGGCTTTGTTAAAGAGCCAGAAAAGGGCCTCTGGGAAAACATCGTGTCCC
TCGATTTTCGCGCTCTGTATCCGTCTATTATCATTACCCACAACGTGTCTCCGGATACTCTCAACCGCGAGGGCTGC
AGAAACTATGATGTTGCTCCGGAAGTAGGCCACAAGTTCTGCAAGGACTTCCCGGGCTTTATTCCGTCTCTCCTGAA
ACGTCTGCTCGATGAACGCCAAAAGATTAAGACTAAAATGAAGGCGTCCCAGGATCCGATTGAAAAAATAATGCTCG
ACTATCGCCAAAGAGCGATTAAAATCCTCGCAAACTCTTATTACGGCTATTATGGCTATGCAAAAGCACGCTGGTAC
TGTAAGGAGTGTGCTGAGTCCGTTACTGCTTGGGGTCGCGAATACATCGAGTTCGTGTGGAAGGAGCTCGAAGAAA
GTTTGGCTTTAAAGTTCTCTACATTGACACTGATGGTCTCTATGCGACTATTCCGGGTGGTAAGTCTGAGGAAATTA
AGAAAAAGGCTCTAGAATTTGTGGATTACATTAACGCGAAGCTCCCGGGTCTCCTGGAGCTCGAATATGAAGGCTTT
TATAAACGCGGCTTCTTCGTTACCAAGAAGAAATATGCGCTGATTGATGAAGAAGGCAAAATTATTACTCGTGGTCT
CGAGATTGTGCGCCGTGATTGGAGCGAAATTGCGAAAGAAACTCAAGCTAGAGTTCTCGAGGCTATTCTCAAACACG
GCAACGTTGAAGAAGCTGTGAGAATTGTAAAAGAAGTAACCCAAAAGCTCTCTAAATATGAAATTCCGCCAGAGAAG
CTCGCGATTTATGAGCAGATTACTCGCCCGCTGCATGAGTATAAGGCGATTGGTCCGCACGTGGCTGTTGCAAAGAG
ACTGGCTGCTAAAGGCGTGAAATTAAACCGGGTATGGTAATTGGCTACATTGTACTCCGCGGCGATGGTCCGATTA
GCAACCGTGCAATTCTAGCTGAGGAATACGATCCGAGAAAGCACAAGTATGACGCAGAATATTACATTGAGAACCAG
GTGCTCCCGGCGGTACTCCGTATTCTGGAGGGTTTTGGCTACCGTAAGGAAGACCTCCGCTGGCAAAAGACTAAACA
GACTGGCCTCACTTCTTGGCTCAACATTAAAAAATCCGGTACCGGCGGTGGCGGTGCAACCGTAAAGTTCAAGTACA
AAGGCGAAGAAAAGGAGGTAGACATCTCCAAGATCAAGAAAGTATGCGTGTGGGcccaATGATCTCCTTCACCTAC
GACGAGGGCGGTGGCAAGACCGGCCGTGGTGCGGTAAGCGAAAAGGACGCGCCAAGGAGCTGCTGCAGATGCTGGA
GAAGCAGAAAgcggccgcACTCGAGCACCACCACCACCACCACTGAGATCCGGCTGCTAA SEQ ID NO: 6
Codon-optimized (for bacterial expression system) nucleotide sequence of
fusion protein #2

SEQUENCE LISTING

```
ATGGGCGTGCCGATCGGTGAAATCATCCCACGTAAAGAAATCGAGCTGGAGAACCTGTACGGTAAAAAAATTGCTAT
CGACGCTCTCAACGCCATTTACCAGTTCCTGTCAACTATCCGTCAGAAAGACGGCACTCCGCTCATGGATAGCAAGG
GTCGTATTACCTCTCACCTGTCCGGCCTGTTCTACCGTACGATCAATCTGATGGAAGCAGGGATTAAACCGGTCTAT
GTGTTCGATGGCGAACCGCCAGAgTTCAAAAAgAAaGAGTTGGAAAAACGCCGTGAAGCACGTGAAGAAGCGGAAGA
AAAATGGCGTGAAGCTCTGGAAAAAGGCGAAATCGAAGAAGCGCGTAAATACGCCCAGCGTGCGACCCGTGTCAATG
AAATGCTGATCGAAGACGCCAAAAAACTGCTGGAATTGATGGGTATCCCTATCGTGCAGGCTCCATCTGAAGGCGAA
GCTCAAGCGGCGTATATGGCCGCAAAAGGCTCTGTTTATGCGTCTGCTTCCCAAGATTACGACTCCCTGCTGTTTGG
TGCACCGCGCCTGGTGCGTAACCTGACCATCACGGGTAAGCGTAAGTTGCCGGGTAAGAACGTTTATGTGGAAATTA
AACCTGAACTGATTATTCTGGAAGAGGTCCTGAAAGAGCTGAAACTGACACGCGAAAACTGATTGAACTGGCTATC
CTGGTTGGCACAGACTACAACCCAGGCGGTATCAAAGGCATCGGTCTGAAAAAAGCGCTTGAAATCGTGCGTCAcAG
TAAAGATCCGCTGGCTAAGTTTCAGAAACAGAGCGACGTGGACCTGTATGCAATTAAAGAGTTCTTCCTGAACCCTC
CGGTTACTGATAACTACAACCTGGTTTGGCGCGATCCAGACGAGGAGGGTATCCTGAAATTTCTGTGTGATGAACAc
GATTTCTCCGAGGAACGTGTTAAAAACGGTCTGGAGCGTCTGAAGAAGGCGATCAAAtctGGCGGTGGTAGCGGTGG
CGGCGGTTCTGGCGGTGGTGGCAGCATACCAATGGAGGGCGATGAAGAACTCAAGCTCCTGGCGTTCGCTATAGCAA
CCCTCTATCACGAAGGCGAAGAGTTTGGTAAAGGCCCAATTATAATGATCAGCTATGCAGATGAAGAAGAAGCAAAG
GTGATTACTTGGAAAAAAATAGATCTCCCATACGTTGAGGTTGTATCTTCCGAGCGCGAGATGATTAAGCGCTTTCT
CAAAATTATCCGCGAGAAGGATCCGGACATTATCATTACTTATAACGGCGACTCTTTTGACCTCCCATATCTGGCGA
AACGCGCAGAAAAACTCGGTATTAAACTGACTATCGGCCGTGATGGTTCCGAGCCGAAGATGCAGCGTATCGGCGAT
ATGACCGCTGTAGAAGTTAAGGGTCGTATCCATTTCGACCTGTATCATGTAATTCGTCGTACTATTAACCTCCCGAC
TTACACTCTCGAGGCTGTATATGAAGCAATTTTTGGTAAGCCGAAGGAGAAGGTATACGCCGATGAGATTGCAAAGG
CGTGGGAAACCGGTGAGGGCCTCGAGCGTGTTGCAAAATACTCCATGGAAGATGCAAAGGCGACTTATGAACTCGGC
AAAGAATTCTTCCCAATGGAAGCTCAGCTCTCTCGCCTGGTTGGCCAACCACTGTGGGATGTTTCTCGTTCTTCCAC
CGGTAACCTCGTAGAGTGGTTTCTCCTGCGCAAAGCGTACGAACGCAACGAACTGGCTCCGAACAAGCCAGATGAAC
GTGAGTATGAACGCCGTCTCCGCGAGTCTTACGCTGGTGGCTTTGTTAAAGAGCCAGAAAAGGGCCTCTGGGAAAAC
ATCGTGTCCCTCGATTTTCGCGCTCTGTATCCGTCTATTATCATTACCCACAACGTGTCTCCGGATACTCTCAACCG
CGAGGGCTGCAGAAACTATGATGTTGCTCCGGAAGTAGGCCACAAGTTCTGCAAGGACTTCCCGGGCTTATTCCGT
CTCTCCTGAAACGTCTGCTCGATGAACGCCAAAAGATTAAGACTAAAATGAAGGCGTCCCAGGATCCGATTGAAAAA
ATAATGCTCGACTATCGCCAAAGAGCGATTAAAATCCTCGCAAACTCTTATTACGGCTATTATGGCTATCCGCGGCAT
ACGCTGGTACTGTAAGGAGTGTGCTGAGTCCGTTACTGCTTGGGGTCGCGAATACATCGAGTTCGTGTGGAAGGAGC
TCGAAGAAAGTTTGGCTTTAAAGTTCTCTACATTGACACTGATGGTCTCTATGCGACTATTCCGGGTGGTAAGTCT
GAGGAAATTAAGAAAAAGGCTCTAGAATTTGTGGATTACATTAACGCGAAGCTCCCGGGTCTCCTGGAGCTCGAATA
TGAAGGCTTTTATAAACGCGGCTTCTTCGTTACCAAGAAGAAATATGCGCTGATTGATGAAGAAGGCAAAATTATTA
CTCGTGGTCTCGAGATTGTGCGCCGTGATTGGAGCGAAATTGCGAAAGAAACTCAAGCTAGAGTTCTCGAGGCTATT
CTCAAACACGGCAACGTTGAAGAAGCTGTGAGAATTGTAAAAGAAGTAACCCAAAAGCTCTCTAAATATGAAATTCC
GCCAGAGAAGCTCGCGATTTATGAGCAGATTACTCGCCCGCTGCATGAGTATAAGGCGATTGGTCCGCACGTGGCTG
TTGCAAAGAGACTGGCTGCTAAAGGCGTGAAAATTAAACCGGGTATGGTAATTGGCTACATTGTACTCCGCGGCGAT
GGTCCGATTAGCAACCGTGCAATTCTAGCTGAGGAATACGATCCGAGAAAGCACAAGTATGACGCAGAATATTACAT
TGAGAACCAGGTGCTCCCGGCGGTACTCCGTATTCTGGAGGGTTTTGGCTACCGTAAGGAAGACCTCCGCTGGCAAA
AGACTAAACAGACTGGCCTCACTTCTTGGCTCAACATTAAAAAATCCGGTACCGGCGGTGGCGGTGCAACCGTAAAG
TTCAAGTACAAAGGCGAAGAAAAGAGGTAGACATCTCCAAGATCAAGAAAGTATGCGTGTGGGCccaATGATCTC
CTTCACCTACGACGAGGGCGGTGGCAAGACCGGCCGTGGTGCGGTAAGCGAAAAGGACGCGCCGAAGGAGCTGCTGC
AGATGCTGGAGAAGCAGAAAgcggccgcACTCGAGCACCACCACCACCACCACTGAGATCCGGCTGCTAA SEQ ID NO: 7
Codon-optimized (for bacterial expression system) nucleotide sequence of
fusion protein #3
ATGGGTGTAGAcCTGAAAGACATTATCCCGGGTGAGGCGAAGACTGTGATCGAAGACCTGCGTATCCTGCACGGTAA
GATCATTGTCATTGACGGTTATAACGCGCTGTATCAGTTCCTGGCTGCTATCCGCCAACCGGACGGTACTCCGCTGA
TGGATAACAACGGTCGTATTACCAGCCATCTGTCTGGTCTCTTTTATCGTACGATCAACATCGGTGAAGCGGTCTAT
AAACCAGTATATGTATTTGATGGTAAACCGCCGGAACTGAAAGCGCGAAATTGAGCGTCGTAAAGCCGTTAAGA
AGAAGCCGCGAAAAAGTATGAAGAAGCAGTTCAGTCGGGTGATCTTGAACTGGCGCGCCGTTACGCCATGATGAGCG
CGAAACTGACAGAGGAAATGGTTCGTGACGCGAAATCTCTGCTGGATGCGATGGGCATCCCGTGGGTACAGGCCCCG
GCTGAAGGCGAGGCGCAGGCTGCGTATATCGTTAAAAAAGGTAGCGCCTTACGCTTCCGCTTCCCAGGACTATGATTC
TCTGCTGTTCGGTTCGCCGAAACTGGTGCGTAACCTTACCATCTCTGGCCGTCGTAAGCTGCCACGTAAGAACGAAT
ACGTGGAAGTAAAGCCGGAACTGATTGAACTGGATAAACTGCTAGTCCAGCTGGGCATCACCCTGGAAAACCTGATC
GACATCGGTATTCTGCTGGGGACGGATTACAAACCCGGATGGCTTCGAAGGTATCGGTCCAAAAAAAGCACTGCAGCT
GGTGAAAGCCTATGGTGGCATTGAAAAAATCCCGAAACCGATCCTGAAATCCCCGATCGAAGTTGACGTTATTGCTA
TCAAAAAATATTTTCTGCAGCCGCAGGTTACCGACAACTATCGCATCGAATGGCACACCCCGGACCCGGATGCCGTC
AAACGTATCCTGGTCGACGAACATGACTTTTCCATCGACCGTGTATCGACGGCGCTGGAACGCTACGTAAAAGCgTT
CAAAGAAAACATTCGTGGTGAACAGAAAGGCCTGTCAAGTGGTTCTCCAAGCCGAAAtctggcGGTGGTAGCGGTG
GCGGCGGTTCTGGCGGTGGTGGCAGCATCCTGGATGCTGACTACATCACTGAAGAAGGCAAACCGGTTATCCGCTG
TTCAAAAAAGAGAACGGCGAATTTAAGATTGAGCATGATCGCACCTTTCGTCCATACATTTACGCTCTGCTGAAAGA
TGATTCTAAGATTGAGGAAGTTAAAAAAATCACTGCTGAGCGCCATGGCAAGATTGTTCGTATCGTTGATGCGGAAA
AGGTAGAAAAGAAATTTCTGGGCAGACCAATCACCGTGTGGAGACTGTATTTCGAACATCCACAAGATGTTCCGACT
ATTCGCGAGAAATTCGCGAACATTCTGCAGTTGTTGACATCTTCGAATACGATATTCCATTTGCAAAGCGTTACCT
CATCGACAAAGGCCTGATACCAATGGAGGGCGATGAAGAACTCAAGCCTCCTGGCGTTCGCTATAGCAACCCTCTATC
ACGAAGGCGAAGAGTTTGGTAAAGGCCCAATTATAATGATCAGCTATGCAGATGAAGAAGAAGCAAAGGTGATTACT
TGGAAAAAAATAGATCTCCCATACGTTGAGGTTGTATCTTCCGAGCGCGAGATGATTAAGCGCTTTCTCAAAATTAT
CCGCGAGAAGGATCCGGACATTATCATTACTTATAACGGCGACTCTTTTGACCTCCCATATCTGGCGAAACGCGCAG
AAAAACTCGGTATTAAACTGACTATCGGCCGTGATGGTTCCGAGCCGAAGATGCAGCGTATCGGCGATATGACCGCT
GTAGAAGTTAAGGGTCGTATCCATTTCGACCTGTATCATGTAATTCGTCGTACTATTAACCTCCCGACTTACACTCT
CGAGGCTGTATATGAAGCAATTTTTGGTAAGCCGAAGGAGAAGGTATACGCCGATGAGATTGCAAAGGCGTGGGAAA
CCGGTGAGGGCCTCGAGCGTGTTGCAAAATACTCCATGGAAGATGCAAAGGCGACTTATGAACTCGGCAAAGAATTC
TTCCCAATGGAAGCTCAGCTCTCTCGCCTGGTTGGCCAACCACTGTGGGATGTTTCTCGTTCTTCCACCGGTAACCT
CGTAGAGTGGTTTCTCCTGCGCAAAGCGTACGAACGCAACGAACTGGCTCCGAACAAGCCAGATGAACGTGAGTATG
AACGCCGTCTCCGCGAGTCTTACGCTGGTGGCTTTGTTAAAGAGCCAGAAAAGGGCCTCTGGGAAAACATCGTGTCC
CTCGATTTTCGCGCTCTGTATCCGTCTATTATCATTACCCACAACGTGTCTCCGGATACTCTCAACCGCGAGGGCTG
```

```
CAGAAACTATGATGTTGCTCCGGAAGTAGGCCACAAGTTCTGCAAGGACTTCCCGGGCTTTATTCCGTCTCTCCTGA
AACGTCTGCTCGATGAACGCCAAAAGATTAAGACTAAAATGAAGGCGTCCCAGGATCCGATTGAAAAAATAATGCTC
GACTATCGCCAAAGAGCGATTAAAATCCTCGCAAACTCTTATTACGGCTATTATGGCTATGCAAAAGCACGCTGGTA
CTGTAAGGAGTGTGCTGAGTCCGTTACTGCTTGGGGTCGCGAATACATCGAGTTCGTGTGGAAGGAGCTCGAAGAAA
AGTTTGGCTTTAAAGTTCTCTACATTGACACTGATGGTCTCTATGCGACTATTCCGGGTGGTAAGTCTGAGGAAATT
AAGAAAAAGGCTCTAGAATTTGTGGATTACATTAACGCGAAGCTCCCGGGTCTCCTGGAGCTCGAATATGAAGGCTT
TTATAAACGCGGCTTCTTCGTTACCAAGAAGAAATATGCGCTGATTGATGAAGAAGGCAAAATTATTACTCGTGGTC
TCGAGATTGTGCGCCGTGATTGGAGCGAAATTGCGAAAGAAACTCAAGCTAGAGTTCTCGAGGCTATTCTCAAACAC
GGCAACGTTGAAGAAGCTGTGAGAATTGTAAAAGAAGTAACCCAAAAGCTCTCTAAATATGAATTCCGCCAGAGAA
GCTCGCGATTTATGAGCAGATTACTCGCCCGCTGCATGAGTATAAGGCGATTGGTCCGCACGTGGCTGTTGCAAAGA
GACTGGCTGCTAAAGGCGTGAAAATTAAACCGGGTATGGTAATTGGCTACATTGTACTCCGCGGCGATGGTCCGATT
AGCAACCGTGCAATTCTAGCTGAGGAATACGATCCGAGAAAGCACAAGTATGACGCAGAATATTACATTGAGAACCA
GGTGCTCCCGGCGGTACTCCGTATTCTGGAGGGTTTTGGCTACCGTAAGGAAGACCTCCGCTGGCAAAAGACTAAAC
AGACTGGCCTCACTTCTTGGCTCAACATTAAAAAATCCGGTACCGGCGGTGGCGGTGCAACCGTAAAGTTCAAGTAC
AAAGGCGAAGAAAAGAGGTAGACATCTCCAAGATCAAGAAAGTATGGCGTGTGGGCccaATGATCTCCTTCACCTA
CGACGAGGGCGGTGGCAAGACCGGCCGTGGTGCGGTAAGCGAAAAGGACGCGCCGAAGGAGCTGCTGCAGATGCTGG
AGAAGCAGAAAgcggccgcACTCGAGCACCACCACCACCACCACTGAGATCCGGCTGCTAA SEQ ID NO: 8
Codon-optimized (for bacterial expression system) nucleotide sequence of
fusion protein #4
ATGGGTGTAGAcCTGAAAGACATTATCCCGGGTGAGGCGAAGACTGTGATCGAAGACCTGCTATCCTGCACGGTAA
GATCATTGTCATTGACGGTTATAACGCGCTGTATCAGTTCCTGGCTGCTATCCGCCAACCGGACGGTACTCCGCTGA
TGGATAACAACGGTCGTATTACCAGCCATCTGTCTGGTCTCTTTTATCGTACCATCAACATCGTTGAAGCGGGTATC
AAACCAGTATATGTATTTGATGGTAAACCGCCGGAACTGAAAGCGCGCGAAATTGAGCGTCGTAAAGCCGTTAAAGA
AGAAGCCGCGAAAAAGTATGAAGAAGCAGTTCAGTCGGGTGATCTTGAACTGGCGCGCCGTTACGCCATGATGAGCG
CGAAACTGACAGAGGAAATGGTTCGTGACGCGAAATCTCTGCTGGATGCGATGGGCATCCCGTGGGTACAGGCCCCG
GCTGAAGGCGAGGCGCAGGCTGCGTATATCGTTAAAAAAGGTGACGCTTACGCTTCCGCTTCCCAGGACTATGATTC
TCTGCTGTTCGGTTCGCCGAAACTGGTGCGTAACCTTACCATCTCTGGCCGTCGTAAGCTGCCACGTAAGAACGAAT
ACGTGGAAGTAAAGCCGGAACTGATTGAACTGGATAAACTGCTAGTCCAGCTGGGCATCACCCTGGAAAACCTGATC
GACATCGGTATTCTGCTGGGGACGGATTACAACCCGGATGGCTTCGAAGGTATCGGTCCAAAAAAGCACTGCAGCT
GGTGAAAGCCTATGGTGGCATTGAAAAAATCCCGAAACCGATCCTGAAATCCCCGATCGAAGTTGACGTTATTGCTA
TCAAAAATATTTTCTGCAGCCGCAGGTTACCGACAACTATCGCATCGAATGGCACACCCCGGACCCGGATGCCGTC
AAACGTATCCTGGTCGACGAACATGACTTTTCCATCGACCGTGTATCGACGGCGCTGGAACGCTACGTAAAAGCgTT
CAAAGAAAACATTCGTGGTGAACAGAAAGGCCTGTCAAGTGGTTCTCCAAGCCGAAAtctggcGGTGGTAGCGGTG
GCGGCGGTTCTGGCGGTGGTGGCAGCATACCAATGGAGGGCGATGAAGAACTCAAGCTCCTGGCGTTCGCTATAGCA
ACCCTCTATCACGAAGGCGAAGAGTTTGGTAAAGGCCCAATTATAATGATCAGCTATGCAGATGAAGAAGAAGCAAA
GGTGATTACTTGGAAAAAATAGATCTCCCATACGTTGAGGTTGTATCTTCCGAGCGCGAGATGATTAAGCGCTTTC
TCAAAATTATCCGCGAGAAGGATCCGGACATTATCATTACTTATAACGGCGACTCTTTTGACCTCCCATATCTGGCG
AAACGCGCAGAAAAACTCGGTATTAAACTGACTATCGGCCGTGATGGTTCCGAGCCGAAGATGCAGCGTATCGGCGA
TATGACCGCTGTAGAAGTTAAGGGTCGTATCCATTTCGACCTGTATCATGTAATTCGTCGTACTATTAACCTCCCGA
CTTACACTCTCGAGGCTGTATATGAAGCAATTTTTGGTAAGCCGAAGGAGAAGGTATACGCCGATGAGATTGCAAAG
GCGTGGGAAACCGGTGAGGGCCTCGAGCGTGTTGCAAAATACTCCATGGAAGATGCAAAGGCGACTTATGAACTCGG
CAAAGAATTCTTCCCAATGGAAGCTCAGCTCTCTCGCCTGGTTGGCCAACCACTGTGGGATGTTTCTCGTTCTTCCA
CCGGTAACCTCGTAGAGTGGTTTCCTGCGCAAAGCGTACGAACGCAACAGCTGGCTCCGAACAAGCCAGATGAA
CGTGAGTATGAACGCCGTCTCCGCGAGTCTTACGCTGGTGGCTTTGTTAAAGAGCCAGAAAAGGGCCTCTGGGAAAA
CATCGTGTCCCTCGATTTTCGCGCTCTGTATCCGTCTATTATCATTACCCACAACGTGTCTCCGGATACTCTCAACC
GCGAGGGCTGCAGAAACTATGATGTTGCTCCGGAAGTAGGCCACAAGTTCTGCAAGGACTTCCCGGGCTTTATTCCG
TCTCTCCTGAAACGTCTGCTCGATGAACGCCAAAAGATTAAGACTAAAATGAAGGCGTCCCAGGATCCGATTGAAAA
AATAATGCTCGACTATCGCCAAAGAGCGATTAAAATCCTCGCAAACTCTTATTACGGCTATTATGGCTATGCAAAAG
CACGCTGGTACTGTAAGGAGTGTGCTGAGTCCGTTACTGCTTGGGGTCGCGAATACATCGAGTTCGTGTGGAAGGAG
CTCGAAGAAAAGTTTGGCTTTAAAGTTCTCTACATTGACACTGATGGTCTCTATGCGACTATTCCGGGTGGTAAGTC
TGAGGAAATTAAGAAAAAGGCTCTAGAATTTGTGGATTACATTAACGCGAAGCTCCCGGGTCTCCTGGAGCTCGAAT
ATGAAGGCTTTTATAAACGCGGCTTCTTCGTTACCAAGAAGAAATATGCGCTGATTGATGAAGAAGGCAAAATTATT
ACTCGTGGTCTCGAGATTGTGCGCCGTGATTGGAGCGAAATTGCGAAAGAAACTCAAGCTAGAGTTCTCGAGGCTAT
TCTCAAACACGGCAACGTTGAAGAAGCTGTGAGAATTGTAAAAGAAGTAACCCAAAAGCTCTCTAAATATGAATTC
CGCCAGAGAAGCTCGCGATTTATGAGCAGATTACTCGCCCGCTGCATGAGTATAAGGCGATTGGTCCGCACGTGGCT
GTTGCAAAGAGACTGGCTGCTAAAGGCGTGAAAATTAAACCGGGTATGGTAATTGGCTACATTGTACTCCGCGGCGA
TGGTCCGATTAGCAACCGTGCAATTCTAGCTGAGGAATACGATCCGAGAAAGCACAAGTATGACGCAGAATATTACA
TTGAGAACCAGGTGCTCCCGGCGGTACTCCGTATTCTGGAGGGTTTTGGCTACCGTAAGGAAGACCTCCGCTGGCAA
AAGACTAAACAGACTGGCCTCACTTCTTGGCTCAACATTAAAAAATCCGGTACCGGCGGTGGCGGTGCAACCGTAAA
GTTCAAGTACAAAGGCGAAGAAAAGAGGTAGACATCTCCAAGATCAAGAAAGTATGGCGTGTGGGCccaATGATCT
CCTTCACCTACGACGAGGGCGGTGGCAAGACCGGCCGTGGTGCGGTAAGCGAAAAGGACGCGCCGAAGGAGCTGCTG
CAGATGCTGGAGAAGCAGAAAgcggccgcACTCGAGCACCACCACCACCACCACTGAGATCCGGCTGCTAA SEQ ID NO: 9
Codon-optimized nucleotide sequence of Da FEN1
ATGGGTGTAGAcCTGAAAGACATTATCCCGGGTGAGGCGAAGACTGTGATCGAAGACCTGCTATCCTGC
ACGGTAAGATCATTGTCATTGACGGTTATAACGCGCTGTATCAGTTCCTGGCTGCTATCCGCCAACCGGA
CGGTACTCCGCTGATGGATAACAACGGTCGTATTACCAGCCATCTGTCTGGTCTCTTTTATCGTACCATC
AACATCGTTGAAGCGGGTATCAAACCAGTATATGTATTTGATGGTAAACCGCCGGAACTGAAAGCGCGCG
AAATTGAGCGTCGTAAAGCCGTTAAAGAAGAAGCCGCGAAAAAGTATGAAGAAGCAGTTCAGTCGGGTGA
TCTTGAACTGGCGCGCCGTTACGCCATGATGAGCGCGAAACTGACAGAGGAAATGGTTCGTGACGCGAAA
TCTCTGCTGGATGCGATGGGCATCCCGTGGGTACAGGCCCCGGCTGAAGGCGAGGCGCAGGCTGCGTATA
TCGTTAAAAAAGGTGACGCTTACGCTTCCGCTTCCCAGGACTATGAITCTCTGCTGTTCGGTTCGCCGAA
ACTGGTGCGTAACCTTACCATCTCTGGCCGTCGTAAGCTGCCACGTAAGAACGAATACGTGGAAGTAAAG
CCGGAACTGATTGAACTGGATAAACTGCTAGTCCAGCTGGGCATCACCCTGGAAAACCTGATCGACATCG
```

SEQUENCE LISTING

```
GTATTCTGCTGGGGACGGATTACAACCCGGATGGCTTCGAAGGTATCGGTCCAAAAAAGCACTGCAGCT
GGTGAAAGCCTATGGTGGCATTGAAAAAATCCCGAAACCGATCCTGAAATCCCCGATCGAAGTTGACGTT
ATTGCTATCAAAAAATATTTTCTGCAGCCGCAGGTTACCGACAACTATCGCATCGAATGGCACACCCCGG
ACCCGGATGCCGTCAAACGTATCCTGGTCGACGAACATGACTTTTCCATCGACCGTGTATCGACGGCGCT
GGAACGCTACGTAAAAGCgTTCAAAGAAACATTCGTGGTGAACAGAAAGGCCTGTCTAAGTGGTTCTCC
AAGCCGAAA

SEQ ID NO: 10
Translated amino acid sequence of Codon-optimized Da FEN1:
MGVDLKDIIPGEAKTVIEDLRILHGKIIVIDGYNALYQFLAAIRQPDGTPLMDNNGRITSHLSGLFYRTI
NIVEAGIKPVYVFDGKPPELKAREIERRKAVKEEAAKKYEEAVQSGDLELARRYAMMSAKLTEEMVRDAK
SLLDAMGIPWVQAPAEGEAQAAYIVKKGDAYASASQDYDSLLFGSPKLVRNLTISGRRKLPRKNEYVEVK
PELIELDKLLVQLGITLENLIDIGILLGTDYNPDGFEGIGPKKALQLVKAYGGIEKIPKPILKSPIEVDV
IAIKKYFLQPQVTDNYRIEWHTPDPDAVKRILVDEHDFSIDRVSTALERYVKAFKENIRGEQKGLSKWFS
KPK SEQ ID NO: 11
>>Linker sequence between Da FEN1 and Pfu/DeepVent hybrid DNA
polymerase:
tctGGCGGTGGTAGCGGTGGCGGCGGTTCTGGCGGTGGTGGCAGC SEQ ID NO: 12
Translated amino acid sequence of linker between Da FEN1 and
Pfu/DeepVent hybrid DNA polymerase:
SGGGSGGGGSGGGS SEQ ID NO: 13
Pfu/DeepVent hybrid DNA polymerase uracil-sensing domain coding
sequence
ATCCTGGATGCTGACTACATCACTGAAGAAGGCAAACCGGTTATCCGTCTGTTCAAAAAAGAGAACGGCG
AATTTAAGATTGAGCATGATCGCACCTTTCGTCCATACATTTACGCTCTGCTGAAAGATGATTCTAAGAT
TGAGGAAGTTAAAAAAATCACTGCTGAGCGCCATGGCAAGATTGTTCGTATCGTTGATGCGGAAAAGGTA
GAAAAGAAATTTCTGGGCAGACCAATCACCGTGTGGAGACTGTATTTCGAACATCCACAAGATGTTCCGA
CTATTCGCGAGAAAATTCGCGAACATTCTGCAGTTGTTGACATCTTCGAATACGATATTCCATTTGCAAA
GCGTTAC SEQ ID NO: 14
Uracil-sensing domain coding sequence (underlined) plus additional
nucleotides removed in USD minus construct
ATCCTGGATGCTGACTACATCACTGAAGAAGGCAAACCGGTTATCCGTCTGTTCAAAAAAGAGAACGGCG
AATTTAAGATTGAGCATGATCGCACCTTTCGTCCATACATTTACGCTCTGCTGAAAGATGATTCTAAGAT
TGAGGAAGTTAAAAAAATCACTGCTGAGCGCCATGGCAAGATTGTTCGTATCGTTGATGCGGAAAAGGTA
GAAAAGAAATTTCTGGGCAGACCAATCACCGTGTGGAGACTGTATTTCGAACATCCACAAGATGTTCCGA
CTATTCGCGAGAAAATTCGCGAACATTCTGCAGTTGTTGACATCTTCGAATACGATATTCCATTTGCAAA
GCGTTACCTCATCGACAAAGGCCTG SEQ ID NO: 15
Nucleotide sequence of Pfu/DeepVent hybrid DNA polymerase polymerase
without uracil-sensing domain:
ATACCAATGGAGGGCGATGAAGAACTCAAGCTCCTGGCGTTCGCTATAGCAACCCTCTATCACGAAGGCG
AAGAGTTTGGTAAAGGCCCAATTATAATGATCAGCTATGCAGATGAAGAAGAAGCAAGGTGATTACTTG
GAAAAAAATAGATCTCCCATACGTTGAGGTTGTATCTTCCGAGCGCGAGATGATTAAGCGCTTTCTCAAA
ATTATCCGCGAGGAAGGATCCGGACATTATCATTACTTATAACGACGACTCTTTTGACCTCCCATATCTGG
CGAAACGCGCAGAAAAACTCGGTATTAAACTGACTATCGGCCGTGATGGTTCCGAGCCGAAGATGCAGCG
TATCGGCGATATGACCGCTGTAGAAGTTAAGGGTCGTATCCATTTCGACCTGTATCATGTAATTCGTCGT
ACTATTAACCTCCCGACTTACACTCTCGAGGCTGTATATGAAGCAATTTTTGGTAAGCCGAAGGAGAAGG
TATACGCCGATGAGATTGCAAAGGCGTGGGAAACCGGTGAGGGCCTCGAGCGTGTTGCAAAATACTCCAT
GGAAGATGCAAAGGCGACTTATGAACTCGGCAAAGAATTCTTCCCAATGGAAGCTCAGCTCTCTCGCCTG
GTTGGCCAACCACTGTGGGATGTTTCTCGTTCTTCCACCGGTAACCTCGTAGAGTGGTTTCTCCTGCGCA
AAGCGTACGAACGCAACGAACTGGCTCCGAACAAGCCAGATGAACGTGAGTATGAACGCCGTCTCCGCGA
GTCTTACGCTGGTGGCTTTGTTAAAGAGCCAGAAAAGGGCCTCTGGGAAAACATCGTGTCCCTCGATTTT
CGCGCTCTGTATCCGTCTATTATCATTACCCACAACGTGTCTCCGGATACTCTCAACCGCGAGGGCTGCA
GAAACTATGATGTTGCTCCGGAAGTAGGCCACAAGTTCTGCAAGGACTTCCCGGGCTTTATTCCGTCTCT
CCTGAAACGTCTGCTCGATGAACGCCAAAAGATTAAGACTAAATGAAGGCGTCCCAGGATCCGATTGAA
AAAATAATGCTCGACTATCGCCAAAGAGCGATTAAATCCTCGCAAACTCTTATTACGGCTATTATGGCT
ATGCAAAAGCACGCTGGTACTGTAAGGAGTGTGCTGAGTCCGTTACTGCTTGGGGTCGCGAATACATCGA
GTTCGTGTGGAAGGAGCTCGAAGAAAAGTTTGGCTTTAAAGTTCTCTACATTGACACTGATGGTCTCTAT
GCGACTATTCCGGGTGGTAAGTCTGAGGAAATTAAGAAAAGGCTCTAGAATTTGTGGATTACATTAACG
CGAAGCTCCCGGGTCTCCTGGAGCTCGAATATGAAGGCTTTTATAAACGCGGCTTCTTCGTTACCAAGAA
GAAATATGCGCTGATTGATGAAGAGGCAAATTATTACTCGTGGTCTCGAGATTGTGCGCCGTGATTGG
AGCGAAATTGCGAAAGAAACTCAAGCTAGAGTTCTCGAGGCTATTCTCAAACACGGCAACGTTGAAGAAG
CTGTGAGAATTGTAAAAGAAGTAACCCAAAAGCTCTCTAAATATGAAATTCGCCAGAGAAGCTCGCGAT
TTATGAGCAGATTACTCGCCCGCTGCATGAGTATAAGGCGATTGGTCCGCACGTGGCTGTTGCAAAGAGA
CTGGCTGCTAAAGGCGTGAAAATTAAACCGGGTATGGTAATTGGCTACATTGTACTCCGCGGCGATGGTC
CGATTAGCAACCGTGCAATTCTAGCTGAGGAATACGATCCGAGAAAGCACAAGTATGACGCAGAATATTA
CATTGAGAACCAGGTGCTCCCGGCGGTACTCCGTATTCTGGAGGGTTTTGGCTACCGTAAGGAAGACCTC
CGCTGGCAAAAGACTAAACAGACTGGCCTCACTTCTTGGCTCAACATTAAAAAAA
```

SEQ ID NO: 16
Nucleotide sequence of Pfu/DeepVent hybrid DNA polymerase with uracil-
sensing domain:
ATCCTGGATGCTGACTACATCACTGAAGAAGGCAAACCGGTTATCCGTCTGTTCAAAAAAGAGAACGGCG
AATTTAAGATTGAGCATGATCGCACCTTTCGTCCATACATTTACGCTCTGCTGAAAGATGATTCTAAGAT
TGAGGAAGTTAAAAAAATCACTGCTGAGCGCCATGGCAAGATTGTTCGTATCGTTGATGCGGAAAAGGTA
GAAAAGAAATTTCTGGGCAGACCAATCACCGTGTGGAGACTGTATTTCGAACATCCACAAGATGTTCCGA
CTATTCGCGAGAAATTCGCGAACATTCTGCAGTTGTTGACATCTTCGAATACGATATTCCATTTGCAAA
GCGTTACCTCATCGACAAAGGCCTGATACCAATGGAGGGCGATGAAGAACTCAAGCTCCTGGCGTTCGCT
ATAGCAACCCTCTATCACGAAGGCGAAGAGTTTGGTAAAGGCCCAATTATAATGATCAGCTATGCAGATG
AAGAAGAAGCAAAGGTGATTACTTGGAAAAAAATAGATCTCCCATACGTTGAGGTTGTATCTTCCGAGCG
CGAGATGATTAAGCGCTTTCTCAAAATTATCCGCGAGAAGGATCCGGACATTATCATTACTTATAACGGC
GACTCTTTTGACCTCCCATATCTGGCGAAACGCGCAGAAAAACTCGGTATTAAACTGACTATCGGCCGTG
ATGGTTCCGAGCCGAAGATGCAGCGTATCGGCGATATGACCGCTGTAGAAGTTAAGGGTCGTATCCATTT
CGACCTGTATCATGTAATTCGTCGTACTATTAACCTCCCGACTTACACTCTCGAGGCTGTATATGAAGCA
ATTTTTGGTAAGCCGAAGGAGAAGGTATACGCCGATGAGATTGCAAAGGCGTGGGAAACCGGTGAGGGCC
TCGAGCGTGTTGCAAAATACTCCATGGAAGATGCAAAGGCGACTTATGAACTCGGCAAAGAATTCTTCCC
AATGGAAGCTCAGCTCTCTCGCCTGGTTGGCCAACCACTGTGGGATGTTTCTCGTTCTTCCACCGGTAAC
CTCGTAGAGTGGTTTCTCCTGCGCAAAGCGTACGAACGCAACGAACTGGCTCCGAACAAGCCAGATGAAC
GTGAGTATGAACGCCGTCTCCGCGAGTCTTACGCTGGTGGCTTTGTTAAAGAGCCAGAAAAGGGCCTCTG
GGAAAACATCGTGTCCCTCGATTTTCGCGCTCTGTATCCGTCTATTATCATTACCCACAACGTGTCTCCG
GATACTCTCAACCGCGAGGGCTGCAGAAACTATGATGTTGCTCCGGAAGTAGGCCACAAGTTCTGCAAGG
ACTTCCCGGGCTTTATTCCGTCTCTCCTGAAACGTCTGCTCGATGAACGCCAAAAGATTAAGACTAAAAT
GAAGGCGTCCCAGGATCCGATTGAAAAAATAATGCTCGACTATCGCAAAGAGCGATTAAAATCCTCGCA
AACTCTTATTCGGCTATTATGGCTATGCAAAAGCACGCTGGTACTGTAAGGAGTGTGCTGAGTCCGTTA
CTGCTTGGGGTCGCGAATACATCGAGTTCGTGTGGAAGGAGCTCGAAGAAAGTTTGGCTTTAAAGTTCT
CTACATTGACACTGATGGTCTCTATGCGACTATTCCGGGTGGTAAGTCTGAGGAAATTAAGAAAAGGCT
CTAGAATTTGTGGATTACATTAACGCGAAGCTCCCGGGTCTCCTGGAGCTCGAATATGAAGGCTTTTATA
AACGCGGCTTCTTCGTTACCAAGAAGAAATATGCGCTGATTGATGAAGAAGGCAAAATTATTACTCGTGG
TCTCGAGATTGTGCGCCGTGATTGGAGCGAAATTGCGAAAGAAACTCAAGCTAGAGTTCTCGAGGCTATT
CTCAAACACGGCCAACGTTGAAGAAGCTGTGAGAATTGTAAAAGAAGTAACCCAAAAGCTCTCTAAATATG
AAATTCCGCCAGAGAAGCTCGCGATTTATGAGCAGATTACTCGCCCGCTGCATGAGTATAAGGCGATTGG
TCCGCACGTGGCTGTTGCAAAGAGACTGGCTGCTAAAGGCGTGAAATTAAACCGGGTATGGTAATTGGC
TACATTGTACTCCGCGGCGATGGTCCGATTAGCAACCGTGCAATTCTAGCTGAGGAATACGATCCGAGAA
AGCACAAGTATGACGCAGAATATTACATTGAGAACCAGGTGCTCCCGGCGGTACTCCGTATTCTGGAGGG
TTTTGGCTACCGTAAGGAAGACCTCCGCTGGCAAAAGACTAAACAGACTGGCCTCACTTCTTGGCTCAAC
ATTAAAAAA SEQ ID NO: 17
Nucleotide sequence encoding linker between polymerase and SSo7d
domain
TCCGGTACCGGCGGTGGCGGT SEQ ID NO: 18
Nucleotide sequence encoding linker between polymerase and SSo7d
domain
GCAACCGTAAAGTTCAAGTACAAAGGCGAAGAAAAAGAGGTAGACATCTCCAAGATCAAGAAAGTATGGC
GTGTGGGCcCaATGATCTCCTTCACCTACGACGAGGGCGGTGGCAAGACCGGCCGTGGTGCGGTAAGCGA
AAAGGACGCGCCGAAGGAGCTGCTGCAGATGCTGGAGAAGCAGAAAgcggccgcACTCGAG SEQ ID NO: 19
Translated amino acid sequence of Uracil-sensing domain (till cleavage
point):
ILDADYITEEGKPVIRLFKKENGEFKIEHDRTFRPYIYALLKDDSKIEEVKKITAERHGKIVRIVDAEKV
EKKFLGRPITVWRLYFEHPQDVPTIREKIREHSAVVDIFEYDIPFAKRYLIDKGL SEQ ID NO: 20
Translated amino acid sequence of Pfu/DeepVent hybrid DNA polymerase
(polymerase portion only):
IPMEGDEELKLLAFAIATLYHEGEEFGKGPIIMISYADEEEAKVITWKKIDLPYVEVVSSEREMIKRFLK
IIREKDPDIIITYNGDSFDLPYLAKRAEKLGIKLTIGRDGSEPKMQRIGDMTAVEVKGRIHFDLYHVIRR
TINLPTYTLEAVYEAIFGKPKEKVYADEIAKAWETGEGLERVAKYSMEDAKATYELGKEFFPMEAQLSRL
VGQPLWDVSRSSIGNLVEWELLRKAYERNELAPNKPDEREYERRLRESYAGGFVKEPEKGLWENIVSLDF
RALYPSIIITHNVSPDTLNREGCRNYDVAPEVGHKFCKDFPGFIPSLLKRLLDERQKIKTKMKASQDPIE
KIMLDYRQRAIKILANSYYGYYGYAKARWYCKECAESVTAWGREYIEFVWKELEEKFGEKVLYIDIDGLY
ATIPGGKSEEIKKKALEFVDYINAKLPGLLELEYEGFYKRGFEVIKKKYALIDEEGKIITRGLEIVRRDW
SEIAKETQARVLEAILKHGNVEEAVRIVKEVTQKLSKYEIPPEKLAIYEQITRPLHEYKAIGPHVAVAKR
LAAKGVKIKPGMVIGYIVLRGDGPISNRAILAEEYDPRKHKYDAEYYIENQVLPAVLRILEGFGYRKEDL
RWQKTKQTGLTSWLNIKK SEQ ID NO: 21
Translated amino acid sequence of linker between polymerase portion
and Sso7d:
SGTGGGG

SEQ ID NO: 22

SEQUENCE LISTING

Translated amino acid sequence of Sso7d K28P mutant (amino acid sequence before His-tag):
ATVKFKYKGEEKEVDISKIKKVTA7RVGPMISFTYDEGGGKTGRGAVSEKDAPKELLQMLEKQKAAALE SEQ ID NO: 23
Codon-optimized nucleotide sequence of Pfu FEN1 (The original C-terminal signal sequence, PIP-box motif, of Pfu FEN1 is deleted based on predicted structure):
ATGGGCGTGCCGATCGGTGAAATCATCCCACGTAAAGAAATCGAGCTGGAGAACCTGTACGGTAAAAAA
TTGCTATCGACGCTCTCAACGCCATTTACCAGTTCCTGTCAACTATCCGTCAGAAAGACGGCACTCCGCT
CATGGATAGCAAGGGTCGTATTACCTCTCACCTGTCCGGCCTGTTCTACCGTACGATCAATCTGATGGAA
GCAGGGATTAAACCGGTCTATGTGTTCGATGGCGAACCGCCAGAgTTCAAAAAgAAaGAGTTGGAAAAAC
GCCGTGAAGCACGTGAAGAAGCGGAAGAAAAATGGCGTGAAGCTCTGGAAAAAGGCGAAATCGAAGAAGC
GCGTAAATACGCCCAGCGTGCCGACCCCGTGTCAATGAAATGCTGATCGAAGACGCCAAAAAACTGCTGGAA
TTGATGGGTATCCCTATCGTGCAGGCTCCATCTGAAGGCGAAGCTCAAGCGGCGTATATGGCCGCAAAAG
GCTCTGTTTATGCGTCTGCTTCCCAAGATTACGACTCCCTGCTGTTTGGTGCACCGCGCCTGGTGCGTAA
CCTGACCATCACGGGTAAGCGTAAGTTGCCGGGTAAGAACGTTTATGTGGAAATTAAACCTGAACTGATT
ATTCTGGAAGAGGTCCTGAAAGAGCTGAAACTGACACGCGAAAAACTGATTGAACTGGCTATCCTGGTTG
GCACAGACTACAACCCAGGCGGTATCAAAGGCATCGGTCTGAAAAAAGCGCTTGAAATCGTGCGTCAcAG
TAAAGATCCGCTGGCTAAGTTTCAGAAACAGAGCGACGTGGACCTGTATGCAATTAAAGAGTTCTTCCTG
AACCCTCCGGTTACTGATAACTACAACCTGGTTTGGCGCGATCCAGACGAGGAGGGTATCCTGAAATTTC
TGTGTGATGAACAcGATTTCTCCGAGGAACGTGTTAAAAACGGTCTGGAGCGTCTGAAGAAGGCGATCAA
A SEQ ID NO: 24
Translated amino acid sequence of Codon-optimized Pfu FEN1:
MGVPIGEIIPRKEIELENLYGKKIAIDALNAIYQFLSTIRQKDGTPLMDSKGRITSHLSGLFYRTINLME
AGIKPVYVFDGEPPEFKKKELEKRREAREEAEEKWREALEKGEIEEARKYAQRATRVNEMLIEDAKKLLE
LMGIPIVQAPSEGEAQAAYMAAKGSVYASASQDYDSLLFGAPRLVRNLTITGKRLPGKNVYVEIKPELI
ILEEVLKELKLTREKLIELAILVGTDYNPGGIKGIGLKKALEIVRHSKDPLAKFQKQSDVDLYAIKEFEL
NPPVTDNYNLVWRDPDEEGILKFLCDEHDFSEERVKNGLERLKKAIK SEQ ID NO: 25
USD of Pfu/DeepVent hybrid DNA polymerase (SEQ ID NO: 20)
ILDADYITEEGKPVIRLFKKENGEFKIEHDRTFRPYIYALLKDDSKIEEVKKITAERHGKIVRIV
DAEKVEKKFLGRPITVWRLYFEHPQDVPTIREKIREHSAVVDIFEYDIPFAKRY SEQ ID NO: 26
Additional amino acids deleted from polymerase in addition to USD
LIDKGL SEQ ID NO: 27
Sso7d/Ssh7A/SsoP2
>gi |3891427|pdb|1BNZIA Chain A, Hyperthermophile Protein DNA COMPLEX
MATVKFKYKGEEKEVDISKIKKVWRVGKMISFTYDEGGGKTGRGAVSEKDAPKELLQMLEKQKK

SEQ ID NO: 28
Ssh7b
>gi |3138797|dbj|BAA28275.1| [*Sulfolobus shibatae*]
MVTVKFKYKGEEKEVDTSKIKKVWRVGKMISFTYDEGGGKTGRGAVSEKDAPKELLQMLEKQKK

SEQ ID NO: 29
Sac7d
>gi |152933|gb|AAA80315.1| DNA-binding protein [*Sulfolobus sp.*]
**MVKVKFKYKGEEKEVDTSKIKKVWRVGKMVSFTYDDNGKTGRGAVSEKDAPKELLDMLARAERE
KK**

SEQ ID NO: 30
Sac7e
>gi |70606201|ref|YP_255071.1| DNA-binding protein 7e
[*Sulfolobus acidocaldarius* DSM 639]
**MAKVRFKYKGEEKEVDTSKIKKVWRVGKMVSFTYDDNGKTGRGAVSEKDAPKELMDMLARAEKK
K**

SEQ ID NO: 31
Sto7e
>gi |15920860|ref|NP_376529.1| DNA-binding protein 7e
[*Sulfolobus tokodaii* str. 7]
MVTVKFKYKGEEKEVDISKIKKVWRVGKMISFTYDDNGKTGRGAVSEKDAPKELLQMLEKSGKK

SEQ ID NO: 32
>pET29b-Taq 5'Exo-Linker-Pfu/DeepVent hybrid DNA polymerase-HisTag
(nucleotide sequence of full construct)
ATGTTACCCTTGTTTGAACCAAAAGGTCGCGTTTTATTAGTAGATGGCCATCACTTAGCCTACCGTACAT
TTCACGCATTAAAAGGACTGACTACCTCTCGTGGCGAACCCGTCCAAGCTGTTTATGGATTTGCTAAATC
ATTATTAAAAGCCTTAAAAGAAGATGGTGATGCCGTTATTGTAGTTTTCGATGCAAAAGCCCCCTCATTT

SEQUENCE LISTING

```
CGGCACGAGGCTTATGGTGGTTACAAAGCTGGTCGTGCACCGACGCCCGAAGATTTTCCGCGCCAGTTAG
CCCTTATCAAAGAACTCGTAGATTTATTAGGTCTCGCACGCTTAGAAGTCCCCGGCTACGAAGCAGATGA
CGTTCTCGCCAGCCTTGCCAAGAAAGCAGAAAAAGAAGGATATGAAGTACGCATCCTGACAGCCGACAAA
GACTTATACCAACTCCTTTCAGATCGCATCCACGTTTTACATCCCGAAGGCTACTTAATTACCCCTGCAT
GGCTGTGGGAAAAATATGGATTACGTCCGGATCAATGGGCCGATTACCGTGCTTTAACCGGTGATGAATC
AGATAACCTGCCAGGTGTTAAAGGGATTGGAGAAAAAACTGCCCGTAAATTGTTAGAAGAATGGGGCTCT
TTGGAAGCACTGTTAAAAAACCTTGATCGTCTCAAACCTGCCATCCGCGAAAAAATTCTGGCCGACATGG
ATGACTTAAAACTGAGCTGGGATCTCGCTAAAGTTCGTACCGACTTACCTCTTGAAGTTGATTTTGCAAA
ACGCCGTGAACCTGATCGTGAACGCCTTCGTGCATTTCTTGAACGTCTGGAATTTGGCTCCTTGTTACAT
GAATTT*GGCCTCTTAGAATCAGGCGGTGGTAGCGGTGGCGGCGGTTCTGGCGG***TGGTGGCAGCATC***CTGG*
*ATGCTGACTACATCACTGAAGAAGGCAAACCGGTTATCCGTCTGTTCAAAAAAGAGAACGGCGAATTTAA*
*GATTGAGCATGATCGCACCTTTCGTCCATACATTTACGCTCTGCTGAAAGATGATTCTAAGATTGAGGAA*
*GTTAAAAAAATCACTGCTGAGCGCCATGGCAAGATTGTTCGTATCGTTGATGCGGAAAAGGTAGAAAAGA*
*AATTTCTGGGCAGACCAATCACCGTGTGGAGACTGTATTTCGAACATCCACAAGATGTTCCGACTATTCG*
*CGAGAAAATTCGCGAACATTCTGCAGTTGTTGACATCTTCGAATACGATATTCCATTTGCAAAGCGTTAC*
*CTCATCGACAAAGGCCTGATACCAATGGAGGGCGATGAAGAACTCAAGCTCCTGGCGTTCGCTATAGCAA*
*CCCTCTATCACGAAGGCGAAGAGTTTGGTAAAGGCCCAATTATAATGATCAGCTATGCAGATGAAGAAGA*
*AGCAAAGGTGATTACTTGGAAAAAAATAGATCTCCCATACGTTGAGGTTGTATCTTCCGAGCGCGAGATG*
*ATTAAGCGCTTTCTCAAAATTATCCGCGAGAAGGATCCGGACATTATCATTACTTATAACGGCGACTCTT*
*TTGACCTCCCATATCTGGCGAAACGCGCAGAAAAACTCGGTATTAAACTGACTATCGGCCGTGATGGTTC*
*CGAGCCGAAGATGCAGCGTATCGGCGATATGACCGCTGTAGAAGTTAAGGGTCGTATCCATTTCGACCTG*
*TATCATGTAATTCGTCGTACTATTAACCTCCCGACTTACACTCTCGAGGCTGTATATGAAGCAATTTTTG*
*GTAAGCCGAAGGAGAAGGTATACGCCGATGAGATTGCAAAGGCGTGGGAAACCGGTGAGGGCCTCGAGCG*
*TGTTGCAAAATACTCCATGGAAGATGCAAAGGCGACTTATGAACTCGGCAAAGAATTCTTCCCAATGGAA*
*GCTCAGCTCTCTCGCCTGGTTGGCCAACCACTGTGGGATGTTTCTCGTTCTTCCACCGGTAACCTCGTAG*
*AGTGGTTTCTCCTGCGCAAAGCGTACGAACGCAACGAACTGGCTCCGAACAAGCCAGATGAACGTGAGTA*
*TGAACGCCGTCTCCGCGAGTCTTACGCTGGTGGCTTTGTTAAAGAGCCAGAAAAGGGCCTCTGGGAAAAC*
*ATCGTGTCCCTCGATTTTCGCGCTCTGTATCCGTCTATTATTACCCACAACGTGTCTCCGGATACTC*
*TCAACCGCGAGGGCTGCAGAAACTATGATGTTGCTCCGGAAGTAGGCCACAAGTTCTGCAAGGACTTCCC*
*GGGCTTTATTCCGTCTCTCCTGAAACGTCTGCTCGATGAACGCCAAAAGATTAAGACTAAAATGAAGGCG*
*TCCCAGGATCCGATTGAAAAAATAATGCTCGACTATCGCCAAAGAGCGATTAAAATCCTCGCAAACTCTT*
*ATTACGGCTATTATGGCTATGCAAAAGCACGCTGGTACTGTAAGGAGTGTGCTGAGTCCGTTACTGCTTG*
*GGGTCGCGAATACATCGAGTTCGTGTGGAAGGAGCTCGAAGAAAAGTTTGGCTTTAAAGTTCTCTACATT*
*GACACTGATGGTCTCTATGCGACTATTCCGGGTGGTAAGTCTGAGGAAATTAAGAAAAAGGCTCTAGAAT*
*TTGTGGATTACATTAACGCGAAGCTCCCGGGTCTCCTGGAGCTCGAAATATGAAGGCTTTTATAAACGCGG*
*CTTCTTCGTTACCAAGAAGAAATATGCGCTGATTGATGAAGGCAAAATTATTACTCGTGGTCTCGAG*
*ATTGTGCGCCGTGATTGGAGCGAAATTGCGAAAGAAACTCAAGCTAGAGTTCTCGAGGCTATTCTCAAAC*
*ACGGCAACGTTGAAGAAGCTGTGAGAATTGTAAAGAAGTAACCCAAAAGCTCTCTAAATATGAAATTCC*
*GCCAGAGAAGCTCGCGATTTATGAGCAGATTACTCGCCCGCTGCATGAGTATAAGGCGATTGGTCCGCAC*
*GTGGCTGTTGCAAAGAGACTGGCTGCTAAAGGCGTGAAAATTAAACCGGGTATGGTAATTGGCTACATTG*
*TACTCCGCGGCGATGGTCCGATTAGCAACCGTGCAATTCTAGCTGAGGAATACGATCCGAGAAAGCACAA*
*GTATGACGCAGAATATTACATTGAGAACCAGGTGCTCCCGGCGGTACTCCGTATTCTGGAGGGTTTTGGC*
*TACCGTAAGGAAGACCTCCGCTGGCAAAAGACTAAACAGACTGGCCTCACTTCTTGGCTCAACATTAAAA*
AATCCGGTACCGGCGGTGGCGGT**GCAACCGTAAAGTTCAAGTACAAAGGCGAAGAAAAAGAGGTAGACAT
CTCCAAGATCAAGAAAGTATGGCGTGTGGGCccaATGATCTCCTTCACCTACGACGAGGGCGGTGGCAAG
ACCGGCCGTGGTGCGGTAAGCGAAAAGGACGCGCCGAAGGAGCTGCTGCAGATGCTGGAGAAGCAGAAAg
cggccgcACTCGAGCACCACCACCACCACCACTGA
```

SEQ ID NO: 33
>pET29b-Taq 5'Exo-Linker-Pfu/DeepVent hybrid DNA polymerase-HisTag
(amino acid sequence of full construct)
MLPLFEPKGRVLLVDGHHLAYRTFHALKGLITSRGEPVQAVYGFAKSLLKALKEDGDAVIVVEDAKAPSF
RHEAYGGYKAGRAPTPEDFPRQLALIKELVDLLGLARLEVPGYEADDVLASLAKKAEKEGYEVRILTADK
DLYQLLSDRIHVLHPEGYLITPAWLWEKYGLRPDQWADYRALTGDESDNLPGVKGIGEKTARKLLEEWGS
LEALLKNLDRLKPAIREKILAHMDDLKLSWDLAKVRIDLPLEVDFAKRREPDRERLRAFLERLEFGSLLH
EFGLLESGGGSGGGGSGGGGSILDADYITEEGKPVIRLFKKENGEFKIEHDRTFRPYIYALLKDDSKIEE
VKKITAERHGKIVRIVDAEKVEKKFLGRPITVWRLYFEHPQDVPTIREKIREHSAVVDIFEYDIPFAKRY
LIDKGLIPMEGDEELKLLAFAIATLYHEGEEFGKGPIIMISYADEEEAKVITWKKIDLPYVEVVSSEREM
IKRFLKIIREKDPDIIITYNGDSFDLPYLAKRAEKLGIKLTIGRDGSEPKMQRIGDMTAVEVKGRIHFDL
YHVIRRTINLPTYTLEAVYEAIFGKPKEKVYADEIAKAWETGEGLERVAKYSMEDAKATYELGKEFFPME
AQLSRLVGQPLWDVSRSSIGNLVEWELLRKAYERNELAPNKPDEREYERRLRESYAGGFVKEPEKGLWEN
IVSLDFRALYPSIIITHNVSPDTLNREGCRNYDVAPEVGHKECKDFPGFIPSLLKRLLDERQKIKTKMKA
SQDPIEKIMLDYRQRAIKILANSYYGYYGYAKARWYCKECAESVTAWGREYIEFVWKELEEKFGEKVLYI
DIDGLYATIPGGKSEEIKKKALEFVDYINAKLPGLLELEYEGFYKRGFEVIKKKYALIDEEGKIITRGLE
IVRRDWSEIAKETQARVLEAILKHGNVEEAVRIVKEVTQKLSKYEIPPEKLAIYEQITRPLHEYKAIGPH
VAVAKRLAAKGVKIKPGMVIGYIVLRGDGPISNRAILAEEYDPRKHKYDAEYYIENQVLPAVLRILEGFG
YRKEDLRWQKTKQTGLTSWLNIKKSGTGGGGATVKFKYKGEEKEVDISKIKKVWRVGPMISFTYDEGGGK
TGRGAVSEKDAPKELLQMLEKQKAAALEHHHHHH- SEQ ID NO: 34
>pET29b-Taq 5'Exo-Linker-Pfu/DeepVent hybrid DNA polymerase-HisTag
(Structure breakdown)
>>Codon-optimized nucleotide sequence of Taq 5'Exo domain:
ATGTTACCCTTGTTTGAACCAAAAGGTCGCGTTTTATTAGTAGATGGCCATCACTTAGCCTACCGTACAT
TTCACGCATTAAAAGGACTGACTAGCTCTCGTGGCGAACCCGTCCAAGCTGTTTATGGATTTGCTAAATC
ATTATTAAAAGCCTTAAAAGAAGATGGTGATGCCGTTATTGTAGTTTTCGATGCAAAAGCCCCCTCATTT
CGGCACGAGGCTTATGGTGGTTACAAAGCTGGTCGTGCACCGACGCCCGAAGATTTTCCGCGCCAGTTAG

```
CCCTTATCAAAGAACTCGTAGATTTATTAGGTCTCGCACGCTTAGAAGTCCCCGGCTACGAAGCAGATGA
CGTTCTCGCCAGCCTTGCCAAGAAAGCAGAAAAAGAAGGATATGAAGTACGCATCCTGACAGCCGACAAA
GACTTATACCAACTCCTTTCAGATCGCATCCACGTTTTACATCCCGAAGGCTACTTAATTACCCCTGCAT
GGCTGTGGGAAAAATATGGATTACGTCCGGATCAATGGGCCGATTACCGTGCTTTAACCGGTGATGAATC
AGATAACCTGCCAGGTGTTAAAGGGATTGGAGAAAAAACTGCCCGTAAATTGTTAGAAGAATGGGGCTCT
TTGGAAGCACTGTTAAAAAACCTTGATCGTCTCAAACCTGCCATCCGCGAAAAAATTCTGGCCCACATGG
ATGACTTAAAACTGAGCTGGGATCTCGCTAAAGTTCGTACCGACTTACCTCTTGAAGTTGATTTTGCAAA
ACGCCGTGAACCTGATCGTGAACGCCTTCGTGCATTTCTTGAACGTCTGGAATTTGGCTCCTTGTTACAT
GAATTTGGCCTCTTAGAATCA

SEQ ID NO: 35
Translated amino acid sequence of Codon-optimized Taq 5'Exo domain:
MLPLFEPKGRVLLVDGHHLAYRTFHALKGLITSRGEPVQAVYGFAKSLLKALKEDGDAVIVVEDAKAPSF
RHEAYGGYKAGRAPTPEDFPRQLALIKELVDLLGLARLEVPGYEADDVLASLAKKAEKEGYEVRILTADK
DLYQLLSDRIHVLHPEGYLITPAWLWEKYGLRPDQWADYRALTGDESDNLPGVKGIGEKTARKLLEEWGS
LEALLKNLDRLKPAIREKILAHMDDLKLSWDLAKVRIDLPLEVDFAKRREPDRERLRAFLERLEFGSLLH
EFGLLES SEQ ID NO: 36
>>Linker sequence between Taq 5'Exo domain and Pfu/DeepVent hybrid
DNA polymerase
GGCGGTGGTAGCGGTGGCGGCGGTTCTGGCGGTGGTGGCAGC SEQ ID NO: 37
Translated amino acid sequence of linker between Taq 5'Exo domain and
Pfu/DeepVent hybrid DNA polymerase
GGGSGGGSGGGGS
```

What is claimed is:

1. A polypeptide having polymerase activity and 5'-3' exonuclease activity, the polypeptide comprising a flap endonuclease linked to a family B polymerase catalytic domain.

2. The polypeptide of claim 1, further comprising a heterologous sequence non-specific double-stranded DNA binding domain or sequence non-specific single-stranded DNA binding domain.

3. The polypeptide of claim 2, wherein the heterologous sequence non-specific double stranded DNA binding domain comprises a Sso7 DNA binding domain or a Sso7-like DNA binding domain.

4. The polypeptide of claim 3, wherein the heterologous sequence non-specific double stranded DNA binding domain is at least 60% identical to any of SEQ ID NOs: 27, 28, 29, 30, or 31.

5. The polypeptide of claim 3, wherein the heterologous sequence non-specific double stranded DNA binding domain is at least 95% identical to any of SEQ ID NOs: 27, 28, 29, 30, or 31.

6. The polypeptide of claim 1, wherein the 5'-3' exonuclease domain and the family B polymerase catalytic domain are linked by a linker.

7. The polypeptide of claim 6, wherein the linker is an amino acid linker.

8. The polypeptide of claim 7, wherein the amino acid linker is between 1-50 amino acids in length.

9. The polypeptide of claim 1, wherein the carboxyl terminus of the flap endonuclease is linked via a linker to the amino terminus of the family B polymerase catalytic domain.

10. The polypeptide of claim 1, wherein the flap endonuclease is at least 95% identical to SEQ ID NO:10.

11. The polypeptide of claim 1, wherein the flap endonuclease comprises SEQ ID NO:10.

12. The polypeptide of claim 1, wherein the polypeptide has 3'-5' exonuclease activity.

13. A reaction mixture comprising the polypeptide of claim 1.

14. The reaction mixture of claim 13, further comprising a polynucleotide primer.

15. The reaction mixture of claim 13, wherein the reaction mixture comprises a sample nucleic acid.

16. A method of performing polymerase chain reaction (PCR), the method comprising:
    contacting in an amplification reaction mixture the polypeptide of claim 1 to a sample comprising nucleic acids under conditions to allow for amplification of a target sequence in the nucleic acids, if present; and
    detecting the presence or absence of amplified target sequence.

17. The polypeptide of claim 1, wherein the flap endonuclease is at least 95% identical to SEQ ID NO:24.

18. The polypeptide of claim 1, wherein the flap endonuclease comprises SEQ ID NO:24.

* * * * *